(12) United States Patent
Zhou et al.

(10) Patent No.: US 10,941,214 B2
(45) Date of Patent: *Mar. 9, 2021

(54) COMPOSITIONS AND METHODS COMPRISING HISTIDYL-TRNA SYNTHETASE SPLICE VARIANTS HAVING NON-CANONICAL BIOLOGICAL ACTIVITIES

(71) Applicants: aTyr Pharma, Inc., San Diego, CA (US); Pangu BioPharma Limited, Hong Kong (CN)

(72) Inventors: Jie Zhou, Hong Kong (CN); Ching-Fun Lau, Hong Kong (CN); Zhiwen Xu, Hong Kong (CN); Wing-Sze Lo, Hong Kong (CN); Kristi Helen Piehl, San Diego, CA (US); Leslie Ann Greene, San Diego, CA (US)

(73) Assignees: aTyr Pharma, Inc., San Diego, CA (US); Paneu BioPharma Limited, Hong Kong (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/688,374

(22) Filed: Nov. 19, 2019

(65) Prior Publication Data

US 2020/0216564 A1 Jul. 9, 2020

Related U.S. Application Data

(63) Continuation of application No. 16/005,045, filed on Jun. 11, 2018, now Pat. No. 10,526,419, which is a continuation of application No. 15/257,353, filed on Sep. 6, 2016, now Pat. No. 10,017,582, which is a continuation of application No. 14/262,272, filed on Apr. 25, 2014, now Pat. No. 9,605,265, which is a continuation of application No. 13/766,659, filed on Feb. 13, 2013, now Pat. No. 8,753,638, which is a continuation of application No. 12/725,272, filed on Mar. 16, 2010, now Pat. No. 8,404,242.

(60) Provisional application No. 61/239,747, filed on Sep. 3, 2009, provisional application No. 61/160,630, filed on Mar. 16, 2009.

(51) Int. Cl.
| | |
|---|---|
| C07K 16/40 | (2006.01) |
| C12Q 1/6886 | (2018.01) |
| G01N 33/573 | (2006.01) |
| C12N 9/00 | (2006.01) |
| C12N 15/113 | (2010.01) |
| C12Q 1/6876 | (2018.01) |
| A61K 38/00 | (2006.01) |

(52) U.S. Cl.
CPC ............... *C07K 16/40* (2013.01); *C12N 9/93* (2013.01); *C12N 15/1137* (2013.01); *C12Q 1/6876* (2013.01); *C12Q 1/6886* (2013.01); *C12Y 601/01021* (2013.01); *G01N 33/573* (2013.01); *A61K 38/00* (2013.01); *C07K 2317/24* (2013.01); *C07K 2317/56* (2013.01); *C07K 2317/622* (2013.01); *C07K 2317/76* (2013.01); *C12N 2310/11* (2013.01); *C12N 2310/14* (2013.01); *C12Q 2600/136* (2013.01); *C12Q 2600/156* (2013.01); *G01N 2333/9015* (2013.01); *G01N 2500/04* (2013.01); *G01N 2500/10* (2013.01)

(58) Field of Classification Search
None
See application file for complete search history.

(56) References Cited

U.S. PATENT DOCUMENTS

| | | |
|---|---|---|
| 5,155,214 A | 10/1992 | Baird et al. |
| 5,484,703 A | 1/1996 | Raben et al. |
| 5,556,645 A | 9/1996 | Bockman et al. |
| 5,641,867 A | 6/1997 | Stern et al. |
| 5,663,066 A | 9/1997 | Raben et al. |
| 5,665,066 A | 9/1997 | Fisher |
| 5,981,606 A | 11/1999 | Martin |
| 6,013,483 A | 1/2000 | Coleman et al. |
| 6,225,060 B1 | 5/2001 | Clark et al. |
| 6,228,837 B1 | 5/2001 | Stern et al. |
| 6,428,960 B1 | 8/2002 | Clark et al. |
| 6,548,060 B1 | 4/2003 | Kim |
| 6,800,286 B1 | 10/2004 | Olwin et al. |
| 6,812,339 B1 | 11/2004 | Venter et al. |
| 6,864,226 B1 | 3/2005 | Coleman et al. |
| 6,875,749 B2 | 4/2005 | Schwarz et al. |
| 6,903,189 B2 | 6/2005 | Schimmel et al. |
| 6,916,648 B2 | 7/2005 | Goddard et al. |
| 7,037,505 B2 | 5/2006 | Kim et al. |
| 7,045,301 B2 | 5/2006 | Coleman et al. |
| 7,067,126 B2 | 6/2006 | Schimmel et al. |

(Continued)

FOREIGN PATENT DOCUMENTS

| | | |
|---|---|---|
| CN | 1341725 | 3/2002 |
| CN | 1341727 | 3/2002 |

(Continued)

OTHER PUBLICATIONS

International Preliminary Report on Patentability for International Application No. PCT/US2009/048915, dated Jan. 5, 2011.

(Continued)

*Primary Examiner* — Kagnew H Gebreyesus
(74) *Attorney, Agent, or Firm* — Cooley LLP

(57) ABSTRACT

Isolated histidyl-tRNA synthetase splice variant polynucleotides and polypeptides having non-canonical biological activities are provided, as well as compositions and methods related thereto.

4 Claims, 30 Drawing Sheets

Specification includes a Sequence Listing.

(56) References Cited

U.S. PATENT DOCUMENTS

| | | |
|---|---|---|
| 7,144,984 B2 | 12/2006 | Schimmel et al. |
| 7,196,068 B2 | 3/2007 | Kim et al. |
| 7,273,844 B2 | 9/2007 | Schimmel et al. |
| 7,282,208 B2 | 10/2007 | Kim |
| 7,413,885 B2 | 8/2008 | Schimmel et al. |
| 7,459,529 B2 | 12/2008 | Kim |
| 7,476,651 B2 | 1/2009 | Schimmel et al. |
| 7,482,326 B2 | 1/2009 | Coleman et al. |
| 7,521,215 B2 | 4/2009 | Schimmel et al. |
| 7,528,106 B2 | 5/2009 | Friedlander et al. |
| 7,572,452 B2 | 8/2009 | Kim |
| 7,842,467 B1 | 11/2010 | Heidbrink et al. |
| 7,901,917 B2 | 3/2011 | Schimmel et al. |
| 7,902,165 B2 | 3/2011 | Kim |
| 7,981,426 B2 | 7/2011 | Kim |
| 8,003,780 B2 | 8/2011 | Kim et al. |
| 8,014,957 B2 | 9/2011 | Radich et al. |
| 8,017,593 B2 | 9/2011 | Schimmel et al. |
| 8,026,088 B2 | 9/2011 | Yang |
| 8,101,566 B2 | 1/2012 | Schimmel et al. |
| 8,148,125 B2 | 4/2012 | Schimmel et al. |
| 8,404,242 B2 | 3/2013 | Zhou et al. |
| 8,753,638 B2 | 6/2014 | Zhou et al. |
| 9,605,265 B2 | 3/2017 | Zhou et al. |
| 10,017,582 B2 | 7/2018 | Zhou et al. |
| 10,093,915 B2 | 10/2018 | Wu et al. |
| 10,526,419 B2 | 1/2020 | Zhou et al. |
| 2002/0128187 A1 | 9/2002 | Tang et al. |
| 2002/0160957 A1 | 10/2002 | Stern et al. |
| 2002/0182666 A1 | 12/2002 | Schimmel et al. |
| 2003/0004309 A1 | 1/2003 | Kim et al. |
| 2003/0017564 A1 | 1/2003 | Schimmel et al. |
| 2003/0158400 A1 | 8/2003 | Tang et al. |
| 2003/0165921 A1 | 9/2003 | Tang et al. |
| 2003/0215827 A1 | 11/2003 | Yue et al. |
| 2004/0018505 A1 | 1/2004 | Lee et al. |
| 2004/0048290 A1 | 3/2004 | Lee et al. |
| 2004/0101879 A1 | 5/2004 | Seidel-Dugan et al. |
| 2004/0152079 A1 | 8/2004 | Schimmel et al. |
| 2005/0119175 A1 | 6/2005 | Kim |
| 2005/0181375 A1 | 8/2005 | Aziz et al. |
| 2005/0196754 A1 | 9/2005 | Drmanac et al. |
| 2006/0024288 A1 | 2/2006 | Glidden |
| 2006/0046250 A1 | 3/2006 | Kim |
| 2006/0078553 A1 | 4/2006 | Glidden |
| 2006/0134663 A1 | 6/2006 | Harkin et al. |
| 2006/0204508 A1 | 9/2006 | Champion et al. |
| 2006/0228715 A1 | 10/2006 | Shiffman et al. |
| 2006/0275794 A1 | 12/2006 | Carrino et al. |
| 2007/0037165 A1 | 2/2007 | Venter et al. |
| 2007/0042392 A1 | 2/2007 | Tang et al. |
| 2007/0048322 A1 | 3/2007 | Schimmel et al. |
| 2007/0054278 A1 | 3/2007 | Cargill |
| 2007/0061916 A1 | 3/2007 | Kovalic et al. |
| 2007/0072175 A1 | 3/2007 | Cooper et al. |
| 2007/0083334 A1 | 4/2007 | Mintz et al. |
| 2007/0093440 A1 | 4/2007 | Champion et al. |
| 2007/0111238 A1 | 5/2007 | Jamieson et al. |
| 2007/0154931 A1 | 7/2007 | Radich et al. |
| 2009/0221437 A1 | 9/2009 | Harkin et al. |
| 2009/0221794 A1 | 9/2009 | Kim et al. |
| 2009/0227662 A1 | 9/2009 | Schimmel et al. |
| 2009/0264453 A1 | 10/2009 | Shiffman et al. |
| 2009/0285792 A1 | 11/2009 | Friedlander et al. |
| 2009/0305973 A1 | 12/2009 | Kim et al. |
| 2010/0003230 A1 | 1/2010 | Glidden |
| 2010/0028352 A1 | 2/2010 | Greene et al. |
| 2010/0041608 A1 | 2/2010 | Kim |
| 2010/0048413 A1 | 2/2010 | Arcus et al. |
| 2010/0092434 A1 | 4/2010 | Belani et al. |
| 2010/0138941 A1 | 6/2010 | Kim et al. |
| 2010/0167997 A1 | 7/2010 | Kim |
| 2010/0297149 A1 | 11/2010 | Zhou et al. |
| 2010/0310576 A1 | 12/2010 | Adams et al. |
| 2011/0104139 A1 | 5/2011 | Faber |
| 2011/0110917 A1 | 5/2011 | Schimmel et al. |
| 2011/0117572 A1 | 5/2011 | Kim et al. |
| 2011/0124582 A1 | 5/2011 | Kim et al. |
| 2011/0136119 A1 | 6/2011 | Kim et al. |
| 2011/0150885 A1 | 6/2011 | Watkins et al. |
| 2011/0183924 A1 | 7/2011 | Beck et al. |
| 2011/0189195 A1 | 8/2011 | Kim et al. |
| 2011/0250701 A1 | 10/2011 | Kim et al. |
| 2011/0256119 A1 | 10/2011 | Kim et al. |
| 2012/0004185 A1 | 1/2012 | Greene |
| 2012/0015383 A1 | 1/2012 | Park et al. |
| 2012/0058133 A1 | 3/2012 | Whitman et al. |
| 2012/0064082 A1 | 3/2012 | Watkins et al. |
| 2013/0243766 A1 | 9/2013 | Zhou et al. |
| 2014/0371294 A1 | 12/2014 | Zhou et al. |
| 2017/0114148 A1 | 4/2017 | Zhou et al. |
| 2019/0031775 A1 | 1/2019 | Zhou et al. |

FOREIGN PATENT DOCUMENTS

| | | |
|---|---|---|
| CN | 1352242 | 6/2002 |
| CN | 1352252 | 6/2002 |
| EP | 0893494 | 1/1999 |
| EP | 0893496 | 1/1999 |
| EP | 0897004 | 2/1999 |
| EP | 1275720 | 1/2003 |
| EP | 1300468 | 4/2003 |
| EP | 1377305 | 1/2009 |
| EP | 1776138 | 10/2009 |
| EP | 1274834 | 7/2010 |
| JP | 2003-514510 A | 4/2003 |
| WO | WO 1997/026351 | 7/1997 |
| WO | WO 1997/039017 | 10/1997 |
| WO | WO 1999/045130 | 9/1999 |
| WO | WO 2000/055320 | 9/2000 |
| WO | WO 2001/057190 | 8/2001 |
| WO | WO 2001/074841 | 10/2001 |
| WO | WO 2001/075067 | 10/2001 |
| WO | WO 2001/075078 | 10/2001 |
| WO | WO 2001/088188 | 11/2001 |
| WO | WO 2001/090330 | 11/2001 |
| WO | WO 2001/094568 | 12/2001 |
| WO | WO 2002/055663 | 7/2002 |
| WO | WO 2002/059323 | 8/2002 |
| WO | WO 2002/067970 | 9/2002 |
| WO | WO 2002/068579 | 9/2002 |
| WO | WO 2003/009813 | 2/2003 |
| WO | WO 2003/080648 | 10/2003 |
| WO | WO 2003/094848 | 11/2003 |
| WO | WO 2003/094862 | 11/2003 |
| WO | WO 2004/023973 | 3/2004 |
| WO | WO 2004/060262 | 7/2004 |
| WO | WO 2004/063355 | 7/2004 |
| WO | WO 2004/064863 | 8/2004 |
| WO | WO 2005/073250 | 8/2005 |
| WO | WO 2005/087953 | 9/2005 |
| WO | WO 2005/102395 | 11/2005 |
| WO | WO 2005/113812 | 12/2005 |
| WO | WO 2005/117954 | 12/2005 |
| WO | WO 2006/016217 | 2/2006 |
| WO | WO 2006/048219 | 5/2006 |
| WO | WO 2006/057500 | 6/2006 |
| WO | WO 2006/083087 | 8/2006 |
| WO | WO 2007/064941 | 6/2007 |
| WO | WO 2008/007818 | 1/2008 |
| WO | WO 2008/016356 | 2/2008 |
| WO | WO 2008/021290 | 2/2008 |
| WO | WO 2008/133359 | 11/2008 |
| WO | WO 2009/114623 | 9/2009 |
| WO | WO 2009/152247 | 12/2009 |
| WO | WO 2009/158649 | 12/2009 |
| WO | WO 2010/021415 | 2/2010 |
| WO | WO 2010/041892 | 4/2010 |
| WO | WO 2010/041913 | 4/2010 |
| WO | WO 2010/090471 | 8/2010 |
| WO | WO 2010/096170 | 8/2010 |
| WO | WO 2010/099477 | 9/2010 |
| WO | WO 2010/107825 | 9/2010 |
| WO | WO 2010/120509 | 10/2010 |

(56) References Cited

FOREIGN PATENT DOCUMENTS

| WO | WO 2011/072265 | 6/2011 |
|---|---|---|
| WO | WO 2011/072266 | 6/2011 |
| WO | WO 2011/097031 | 8/2011 |
| WO | WO 2012/021249 | 2/2012 |

OTHER PUBLICATIONS

International Search Report and Written Opinion for International Application No. PCT/US2009/048915, dated Nov. 2, 2009.
Office Action for U.S. Appl. No. 12/482,151, dated Oct. 11, 2011, 43 pages.
Office Action for U.S. Appl. No. 12/482,151, dated Mar. 18, 2011, 11 pages.
International Preliminary Report on Patentability for International Application No. PCT/US2009/046910, dated Dec. 13, 2010.
International Search Report and Written Opinion for International Application No. PCT/US2009/046910, dated Mar. 4, 2010.
Supplementary European Search Report for European Application No. 06838844.6, dated Apr. 9, 2009, 10 pages.
Office Action for U.S. Appl. No. 12/085,884, dated Jan. 20, 2011.
International Preliminary Report on Patentability for International Application No. PCT/US2006/046106, dated Jun. 4, 2008.
International Search Report and Written Opinion for International Application No. PCT/US2006/046106, dated Aug. 9, 2007.
International Preliminary Report on Patentability for International Application No. PCT/US2010/025642, dated Aug. 30, 2011.
International Search Report and Written Opinion for International Application No. PCT/US2010/025642, dated Oct. 29, 2010.
Office Action for U.S. Appl. No. 12/751,358, dated Oct. 3, 2011.
Office Action for U.S. Appl. No. 12/751,358, dated Mar. 3, 2011.
International Preliminary Report on Patentability for International Application No. PCT/US2010/029377, dated Oct. 4, 2011.
International Search Report and Written Opinion for International Application No. PCT/US2010/029377, dated Jan. 26, 2011.
Supplementary European Search Report for European Application No. 10753998.3, dated Nov. 21, 2012.
Office Action for U.S. Appl. No. 12/725,272, dated Jul. 13, 2012, 9 pages.
Restriction Requirement for U.S. Appl. No. 12/725,272, dated Apr. 27, 2012.
International Preliminary Report on Patentability for International Application No. PCT/US2010/027525, dated Sep. 20, 2011.
International Search Report and Written Opinion for International Application No. PCT/US2010/027525, dated Jan. 10, 2011.
Extended European Search Report for European Application No. 17169885.5, dated Oct. 6, 2017, 6 pages.
Office Action for U.S. Appl. No. 13/766,659, dated Nov. 19, 2013.
Office Action for U.S. Appl. No. 13/766,659, dated Sep. 16, 2013.
International Search Report and Written Opinion for International Application No. PCT/US2010/059964, dated Aug. 25, 2011.
International Search Report and Written Opinion for International Application No. PCT/US2010/059963, dated May 12, 2011.
International Search Report and Written Opinion for International Application No. PCT/US2011/000210, dated Aug. 12, 2011.
Adams, M. D. et al., "The genome sequence of *Drosophila melanogaster*," Science, 287(5961):2185-2195 (2000).
Aderem, A. et al., "Toll-like receptors in the induction of the innate immune response," Nature, 406:782-787 (2000).
Amaar, Y. G. et al., "Cloning and characterization of the C.elegans histidyl-tRNA synthetase gene," Nucleic Acids Research, 21(18):4344-4347 (1993).
Ascherman, D. P. et al., "Critical Requirement for Professional APCs in Eliciting T Cell Responses to Novel Fragments of Histidyl-tRNA Synthetase (Jo-1) in Jo-1 Antibody-Positive Polymyositis," J. Immunol., 169:7127-7134 (2002).
Ascherman, D. P., "The Role of Jo-1 in the Immunopathogenesis of Polymyositis: Current Hypotheses," Current Rheumatology Reports, 5:425-430 (2003).

Barbasso, S. et al., "Sera From Anti-Jo-1-Positive Patients with Polymyositis and Interstitial Lung Disease Induce Expression of Intercellular Adhesion Molecule 1 in Human Lung Endothelial Cells," Arthritis & Rheumatism, 60(8):2524-2530 (2009).
Bernstein, R. M. et al., "Anti-Jo-1 antibody: a marker for myositis with interstitial lung disease," British Medical Journal, 289:151-152 (1984).
Blechynden, L.M. et al., "Sequence and polymorphism analysis of the murine gene encoding histidyl-tRNA synthetase," Gene, 178:151-156 (1996).
Blechynden, L.M. et al., "Myositis Induced by Naked DNA Immunization with the Gene for Histidyl-tRNA Synthetase," Human Gene Therapy, 8:1469-1480 (Aug. 10, 1997).
Blum, D. et al., "Extracellular toxicity of 6-hydroxydopamine on PC12 cells," Neuroscience Letters, 283(3):193-196 (2000).
Brightbill, H. D. et al., "Toll-like receptors: molecular mechanisms of the mammalian immune response," Immunology, 101:1-10 (2000).
Broun, P. et al., "Catalytic plasticity of fatty acid modification enzymes underlying chemical diversity of plant lipids," Science, 282:1315-1317 (1998).
Brown, M. V. et al., "Mammalian aminoacyl-tRNA synthetases: Cell signaling functions of the protein translation machinery," Vascular Pharmacology, 52(1-2):21-26 (2010).
Casciola-Rosen, L. et al., "Cleavage by Granzyme B Is Strongly Predictive of Autoantigen Status: Implications for Initiation of Autoimmunity," J. Exp. Med., 190(6):815-825 (1999).
Casciola-Rosen, L., "Histidyl-Transfer RNA Synthetase: A Key Participant in Idiopathic Inflammatory Myopathies," Arthritis and Rheumatism, 63(2):331-333 (2011).
Chica, R. A. et al., "Semi-rational approaches to engineering enzyme activity: combining the benefits of directed evolution and rational design," Curr. Opin. Biotechnol., 16:378-384 (2005).
Choi, W. S. et al., "Two Distinct Mechanisms Are Involved in 6-Hydroxydopamine-and MPP+-Induced Dopaminergic Neuronal Cell Death: Role of Caspases, ROS, and JNK," Journal of Neuroscience Research, 57(1):86-94 (1999).
Delgado, C. et al., "The uses and properties of PEG-linked proteins," Critical Reviews in Therapeutic Drug Carrier Systems, 9(3,4):249-304 (1992).
Devos, D. et al., "Practical limits of function prediction," Proteins: Structure, Function, and Genetics, 41:98-107 (2000).
Ewalt, K. L. et al., "Activation of Angiogenic Signaling Pathways by Two Human tRNA Synthetases," Biochemistry, 41(45):13344-13349 (2002).
Frommhold, D. et al., "Sialyltransferase ST3Gal-IV controls CXCR2-mediated firm leukocyte arrest during inflammation," Journal of Experimental Medicine, 205(6):1435-1446 (2008).
GenBank Accession No. AA984229, published May 27, 1998.
GenBank Accession No. AK055917, published Jan. 19, 2008.
GenBank Accession No. AK124831, published Jul. 3, 2008.
GenBank Accession No. AK225776, published Jul. 22, 2006.
GenBank Accession No. AK293154, published Jul. 24, 2008.
GenBank Accession No. AK293531, published Jul. 24, 2008.
GenBank Accession No. AK295219, published Jul. 24, 2008.
GenBank Accession No. AK302295, published Jul. 24, 2008.
GenBank Accession No. AK303778, published Jul. 24, 2008.
GenBank Accession No. AU129836, published Feb. 18, 2011.
GenBank Accession No. BE872272, published Jan. 13, 2011.
GenBank Accession No. BF791754, published Jan. 13, 2011.
GenBank Accession No. BG108830, published Jun. 1, 2001.
GenBank Accession No. BP268250, published Feb. 10, 2011.
GenBank Accession No. DA083923, published Feb. 17, 2011.
GenBank Accession No. DB146646, published Feb. 16, 2011.
GenBank Accession No. Q7QD89, Anopheles gambiae Sequence Committee, submitted Apr. 2002, [Retrieved from the Internet Apr. 24, 2007], <URL: http://www.ncbi.nlm.nih.gov/entrez/viewer.fcgi?db=protein&val=74803944>.
GenBank Accession No. Q9VV60, published May 1, 2000.
GenBank Accession No. Z11518, published Oct. 7, 2008.
Goldgur, Y. et al., "The crystal structure of phenylalanyl-tRNA synthetase from Thermus thermophilus complexed with cognate tRNA," Structure, 5(1):59-68 (1997).

(56) References Cited

OTHER PUBLICATIONS

Greenberg, Y. et al., "The novel fragment of tyrosyl tRNA synthetase, mini-TyrRS, is secreted to induce an angiogenic response in endothelial cells," FASEB Journal, 22(5):1597-1605 (2008).
Guijarro, J. I. et al., "Structure and Dynamics of the Anticodon Arm Binding Domain of Bacillus stearothermophilus Tyrosyl-tRNA Synthetase," Structure, 10(3):311-317 (2002).
Guo, R-T. et al., "Crystal structures and biochemical analyses suggest a unique mechanism and role for human glycyl-tRNA synthetase in Ap4A homeostasis," Journal of Biological Chemistry, 284(42):28968-28976 (2009).
Guo, M. et al., "Functional expansion of human tRNA synthetases achieved by structural inventions," FEBS Letters, 584(2):434-442 (2010).
Guo, H. H., "Protein tolerance to random amino acid change," PNAS, 101(25):9205-9210 (Jun. 22, 2004).
Hanrott, K. et al., "6-Hydroxydopamine-induced Apoptosis Is Mediated via Extracellular Auto-oxidation and Caspase 3-dependent Activation of Protein Kinase C8," The Journal of Biological Chemistry, 281(9):5373-5382 (2006).
Hausmann, C. D. et al., "Aminoacyl-tRNA synthetase complexes: molecular multitasking revealed," FEMS Microbiol. Rev., 32(4):705-721 (2008).
Hengstman, G. J. D. et al., "Anti-Jo-1 positive inclusion body myositis with a marked and sustained clinical improvement after oral prednisone," J. Neurol. Neurosurg. Psychiatry, 70(5):706 (2001).
Hou, Y-M. et al., "Sequence determination and modeling of structural motifs for the smallest monomeric aminoacyl-tRNA synthetase," Proc. Nat. Acad. Sci., 88(3):976-980 (1991).
Howard, O. M. Z. et al., "Histidyl-tRNA Synthetase and Asparaginyl-tRNA Synthetase, Autoantigens in Myositis, Activate Chemokine Receptors on T Lymphocytes and Immature Dendritic Cells," The Journal of Experimental Medicine, 196(6):781-791 (2002).
Howard, O. M. Z. et al., "Autoantigens signal through cheokine receptors: uveitis antigens induce CXCR3- and CRCR5-expressing lymphocytes and immature dendritic cells to migrate", Blood, 105(11) 4207-4214 (2005).
Ivakhno, S. S. et al., "Cytokine-Like Activities of Some Aminoacyl-tRNA Synthetases and Auxiliary p43 Cofactor of Aminoacylation Reaction and Their Role in Oncogenesis," Exp. Oncol., 26(4):250-255 (2004).
Izumi, Y. et al., "p-Quinone Mediates 6-Hydroxydopamine-Induced Dopaminergic Neuronal Death and Ferrous Iron Accelerates the conversion of p-Quinone Into Melanin Extracellularly," Journal of Neuroscience Research, 79(6):849-860 (2005).
Jacobo-Molina, A. et al., "cDNA Sequence, Predicted Primary Structure, and Evolving Amphiphilic Helix of Human Aspartyl-tRNA Synthetase," Journal of Biological Chemistry, 264(28):16608-16612 (1989).
Jia, J. et al., "WHEP Domains Direct Noncanonical Function of Glutamyl-Prolyl tRNA Synthetase in Translational Control of Gene Expression," Molecular Cell, 29(6):679-690 (2008).
Jura, M. et al., "Comprehensive Insight into human aminoacyl-tRNA synthetases as autoantigens in idiopathic inflammatory myopathies," Critical Reviews in Immunology, 27(6):559-572 (2007).
Kapoor, M. et al., "Mutational separation of aminoacylation and cytokine activities of human tyrosyl-tRNA synthetase," Chemistry & Biology, 16(5):531-539 (2009).
Katsumata, Y. et al., "Species-specific immune responses generated by histidyl-tRNA synthetase immunization are associated with muscle and lung inflammation," Journal of Autoimmunity, 29(2-3):174-186 (2007).
Katsumata, Y. et al., "Animal models in myositis," Current Opinion in Rheumatology, 20:681-685 (2008).
Kimchi-Sarfaty, C. et al., "A 'Silent' polymorphism in the MDR1 gene changes substrate specificty," Science, 315:525-528 (2007).
Kise, Y. et al., "A short peptide insertion crucial for angiostatic activity of human tryptophanyl-tRNA synthetase," Nature Structural & Molecular Biology, 11(2):149-156 (2004).
Kochendoerfer, G. G., "Site-specific polymer modification of therapeutic proteins," Current Opinion in Chemical Biology, 9:555-560 (2005).
Kovaleski, B. J. et al.,"In vitro characterization of the interaction between HIV-1 Gag and human lysyl-tRNA synthetase," J. Bio. Chem., 281(28):19449-19456 (2006).
Levine, S. M. et al., "Anti-aminoacyl tRNA synthetase immune responses: insights into the pathogenesis of the idiopathic inflammatory myopathies," Current Opinion in Rheumatology, 15(6):708-713 (2003).
Levine, S. M., et al., "Novel Conformation of Histidyl-Transfer RNA Synthetase in the Lung", Arthritis & Rheumatism, 56(8): 2729-2739 (2007).
Link, A. J. et al., "Discovery of aminoacyl-tRNA synthetase activity through cell-surface display of noncanonical amino acids," Proc. Nat. Acad. Sci., 103(27):10180-10185 (2006).
Martin, A. et al., "Epitope studies indicate that histidyl-tRNA synthetase is a stimulating antigen in idiopathic myositis," The FASEB Journal, 9:1226-1233 (1995).
Matthews, B. W., "Structural and genetic analysis of protein stability," Annu. Rev. Biochem., 62:139-160 (1993).
Miller, F. W., et al., "Origin and Regulation of a Disease-specific Autoantibody Response, Antigenic Epitopes, Spectrotype Stability, and Isotype Restriction of Anti-Jo-1 Autoantibodies," J. Clin. Invest., 85:468-475 (1990).
Molecular Modeling Database (MMDB), "Solution Structures of the Whep-trs domain of human histidyl-trna synthetase," MMDB ID No. 35920, available for www.ncbi.nlm.nih.gov/Structure/mmdb, accessed Aug. 24, 2012.
Nackley, A. G. et al., "Human Caechol-O-Methyltransferase haplotypes modulate protein expression by altering mRNA secondary structure," Science, 314:1930-1933 (2006).
Nameki, N. et al., Accession 1X59, Solution Structures of the WHEP-TRS Domain of Human Histidyl-TRNA Synthetase, May 15, 2015, 2 pages.
Ng, P. C. et al., "Predicting the effects of amino acid substitutions on protein function," Annu. Rev. Genomics Hum. Genet., 7:61-80 (2006).
Ngo, J. T. et al., "Computational complexity, protein structure prediction, and the Levinthal paradox," In the Protein Folding Problem and Tertiary Structure Prediction, Merz et al. (ed.), Birkhauser, Boston, MA, pp. 433 and 492-495 (1994).
Nichols, R. C. et al., "Human isoleucyl-tRNA synthetase: sequence of the cDNA, alternative mRNA splicing, and the characteristics of an unusually long C-terminal extension," Gene, 155(2):299-304 (1995).
Nishikai, M. et al., "Heterogeneity of Precipitating Antibodies in Polymyositis and Dermatomyositis," Arthritis and Rheumatism, 23(8):881-888 (1980).
O'Hanlon, T. P. et al., "Genomic organization, transcriptional mapping, and evolutionary implications of the human bi-directional histidyl-tRNA synthetase locus (HARS/HARSL)," Biochemical and Biophysical Research Communications, 294:609-614 (2002).
Oppenheim, J. J. et al., "Autoantigens act as tissue-specific chemoattractants," Journal of Leukocyte Biology, 77:854-861 (2005).
Park, S. G., et al., "Aminoacyl tRNA synthetases and their connections to disease," PNAS, 105(32):11043-11049 (2008).
Park, S. G. et al., "Dose-dependent biphasic activity of tRNA synthetase-associating factor, p. 43, in angiogenesis," The Journal of Biological Chemistry, 277(47):45243-45248 (2002).
Park, S. G. et al., "Is there an answer? Do aminoacyl-tRNA synthetases have biological functions other than in protein biosynthesis?" IUBMB Life, 58(9):556-558 (2006).
Parker, L. C. et al., "Toll-Like Receptor (TLR)2 and TLR4 Agonists Regulate CCR Expression in Human Monocytic Cells," The Journal of Immunology, 172:4977-4986 (2004).
Pierce, S. B. et al., "Mutations in mitochondrial histidyl tRNA synthetase HARS2 cause ovarian dysgenesis and sensorineural hearing loss of Perrault syndrome," PNAS, 108(16):6543-6548 (2011).
Quesniaux, V. F.J. et al., "Hematopoiesis, including lymphocyte developmet and maturation," Principles of Immunopharmacology, pp. 3-17 (2005).

(56) References Cited

OTHER PUBLICATIONS

Reed, V. S. et al., "Characterization of a Novel N-terminal Peptide in Human Aspartyl-tRNA Synthetase," Journal of Biological Chemistry, 269(52):32937-32941 (1994).
Richardson, R. M. et al., "Role of the cytoplasmic tails of CXCR1 and CXCR2 in mediating leukocyte migration, activation, and regulation," Journal of Immunology, 170(6):2904-2911 (2003).
Sauna, Z. E. et al., "Silent polymorhisms speak: How they affect pharmacogenomics and the treatment of cancer," Cancer Res., 67(20):9609-9612 (2007).
Seburn, K. L. et al., "An active dominant mutation of glycyl-tRNA synthetase causes neuropathy in a Charcot-Marie-Tooth 2D mouse model," Neuron, 51(6):715-726 (2006).
Sen, S. et al., "Developments in directed evolution for improving enzyme functions," Appl. Biochem. Biotechnol., 143:212-223 (2007).
Smith, D. F. et al., "Leukocyte phosphoinositide-3 kinase γ is required for chemokine-induced, sustained adhesion under flow in vivo," Journal of Leukocyte Biology, 80(6):1491-1499 (2006).
Soejima, M. et al., "Role of Innate Immunity in a Murine Model of Histidyl-Transfer RNA Snythetase (Jo-1)-Mediated Myositis," Arthritis and Rheumatism, 63(2):479-487 (2011).
Sultan, S. M. et al., "Re-classifiyng myositis," Rheumatology, 49:831-833 (2010).
Tarabishy, A. B. et al., "Retinal Vasculitis Associated with the Anti-Synthetase Syndrome," Ocular Immunology & Inflamation, 18(1):16-18 (2010).
Targoff, I. N., "Update on myositis-specific and myositis-associated autoantibodies," Current Opinion in Rheumatology, 12:475-481 (2000).
Traves, S. L. et al., "Specific CXC but not CC chemokines cause elevated monocyte migration in COPD: a role for $CXCR_1$," Journal of Leukocyte Biology, 76(2):441-450 (2004).
Tsui, H. W. et al., "Transcriptional analyses of the gene region that encodes human histidyl-tRNA sysnthetase: identification of a novel bidirectional regulatory element," Gene, 131:201-208 (1993).
Tzioufas, A. G. et al., "Antisynthetase syndrome," Orphanet Encyclopedia, http://www.orpha.net/data/patho/GB/uk-antisynthetase.pdf, pp. 1-5 Nov. 2001.
Veronese, F. M. et al., "Preface: Introduction and overview of peptide and protein pegylation," Advanced Drug Delivery Reviews, 54:453-456 (2002).
Wakasugi, K. et al., "Two distinct cytokines released from a human aminoacyl-tRNA synthetase," Science, 284:147-151 (1999).
Wakasugi, K. et al., "A human aminoacyl-tRNA synthetase as a regulator of angiogenesis," PNAS USA, 99(1):173-177 (2002).
Wakasugi, K. et al., "Induction of angiogenesis by a fragment of human tyrosyl-tRNA synthetase," The Journal of Biological Chemistry, 277(23):20124-20126 (2002).
Wallace, E. A. et al., "Diagnosis and management of inflammatory muscle disease," The Journal of Musculoskeletal Medicine, 27(12):1-7 (2010).

Whisstock, J. C. et al., "Prediction of protein function from protein sequence," Q. Rev. Biophysics., 36(3):307-340 (2003).
Wishart, M. J. et al., "A single mutation converts a novel phosphotyrosine binding domain into a dual-specificity phosphatase," J. Biol. Chem., 270(45):26782-26785 (1995).
Witkowski, A. et al., "Conversion of β-ketoacyl synthase to a Malonyl Decarboxylase by replacement of the active cysteine with glutamine," Biochemistry, 38:11643-11650 (1999).
Xie, W. et al., "Long-range structural effects of a Charcot-Marie-Tooth disease-causing mutation in human glycyl-tRNA synthetase," PNAS, 104(24):9976-9981 (2007).
Yang, X-L et al., "Crystal structure of a human aminoacyl-tRNA synthetase cytokine," PNAS, 99(24):15369-15374 (2002).
Yang, X.-L et al., "Relationship of two human tRNA synthetases used in cell signaling," Trends in Biochemical Sciences, 29(5):250-256 (2004).
Yang, X-L et al., "Gain-of-Function Mutational Activation of Human tRNA Synthetase Procytokine," Chemistry & Biology, 14(12):1323-1333 (2007).
Yousem, S. A. et al., "The pulmonary histopathologic manifestations of the anti-Jo-1 tRNA synthetase syndrome," Modern Pathology, 23:874-880 (2010).
Yu, Y. et al., "Crystal structure of human tryptophanyl-tRNA synthetase catalytic fragment," The Journal of Biological Chemistry, 279(9):8378-8388 (2004).
Zalipsky, S. et al., "Use of functionalized poly(ethylene glycol)s for modification of polypeptides," Chapter 21 In: Poly(Ethylene Glycol) Chemistry: Biotechnical and Biomedical Applications, Harris, J. M. (ed.), pp. 347-370, Plenum Press, New York (1992).
Zhou, Q. et al., "Orthogonal use of a human tRNA synthetase active site to achieve multifunctionality," Nature Structural & Molecular Biology, 17(1):57-62 (2010).
Zwijnenburg, P. J. G. et al., B-1426, "Tyrosyl tRNA synthetase is a chemotactic factor in cerebrospinal fluid from patients with bacterial meningitis," Abstracts of the 42nd Interscience Conference on Antimicrobial Agents and Chemotherapy, San Diego, California, Sep. 27-30, 2002, Session 156(B), p. 55.
Raben, N. et al., "A Motif in Human Histidyl-tRNA Synthetase Which Is Shared among Several Aminoacyl-tRNA Synthetases Is a Coiled-coil That is Essential for Enzymatic Activity and Contains the Major Autoantigenic Epitope," The Journal of Biological Chemistry, 269(39):24277-24283 (1994).
Von Luettichau, I. et al., "Rantes chemokine expression in diseased and normal human tissues," Cytokine, vol. 8, No. 1, pp. 89-98 (Jan. 1996).
Han, J-H et al., "Macrophage inflammatory protein-1α is an osteoclastogenic factor in myeloma that is independent of receptor activator of nuclear factor κb ligand," Blood, vol. 97, No. 11 pp. 3349-3353 (Jun. 2001).
Hashimoto, T. et al., "Ability of myeloma cells to secrete macrophage inflammatory protein (MIP)-1α and MIP-1β correlates with lytic bone lesions in patients with multiple myeloma," British Journal of Haematology, vol. 125, No. 1, pp. 38-41 (Apr. 2004).
Doan, H. Q. et al., "Toll-like Receptor 4 Activation Increases Akt Phosphorylation in Colon Cancer Cells," Anticancer Research, vol. 29, No. 7, pp. 2473-2478 (Jul. 2009).

HRS-SV9:
¹ATGGCAGAGCGTGCGGCCCTGGAGGAGCTGGTGAAACTTCAGGGAGAGCGCGTGCGAGGCCTCAAGCAGCAGA
AGGCCAGCGCCGAGCTGATCGAGGAGGAGGTGGCGAAACTCCTGAAACTGAAGGCACAGCTGGGTCCTGATGA
AAGCAAACAGAAATTTGTGCTCAAAACCCCCAAGTAG¹⁹⁸

HRS-SV11:
¹ATGGCAGAGCGTGCGGCCCTGGAGGAGCTGGTGAAACTTCAGGGAGAGCGCGTGCGAGGCCTC
AAGCAGCAGAAGGCCAGCGCCGAGCTGATCGAGGAGGAGGTGGCGAAACTCCTGAAACTGAAG
GCACAGCTGGGTCCTGATGAAAGCAAACAGAAATTTGTGCTCAAAACCCCCAAGGCTTTGGAGG
AGAAGATACGGACCACGGAGACACAGGTGCTTGTGGCATCTGCACAGAAGAAGCTGCTAGAGG
AAAGACTAAAGCTTGTCTCAGAACTGTGGGATGCTGGGATCAAGGCTGAGCTGCTGTACAAGAA
GAACCCAAAGCTACTGAACCAGTTACAGTACTGTGAGGAGGCAGGCATCCCACTGGTGGCTATC
ATCGGCGAGCAGGAACTCAAGGATGGGGTCATCAAGCTCCCTTCAGTGACGAGCAGGGAAGAG
GTGGATGTCCGAAGAGAAGACCTTGTGGAGGAAATCAAAAGGAGAACAGGCCAGCCCCTCTGC
ATCTGCTGA⁵⁴⁸

HRS-SV14:
¹ATGGCAGAGCGTGCGGCCCTGGAGGAGCTGGTGAAACTTCAGGGAGAGCGCCGTGCCGAGGCCTCAAGCAGCAGA
AGGCCAGCGCCGAGCTGATCGAGGAGGAGGTGGCGAAACTCCTGAAACTGAAGGCACAGCTGGGTCCTGATGA
AAGCAAACAGAAATTTGTGCTCAAAACCCCCAAGGGCACAAGAGACTATAGTCCCCGGCAGATGGCAGTTCGCG
AGAAGGTGTTTGACGTAATCATCCGTTGCTTCAAGCGCCACGGTGCAGAAGTCATTGATACACCTGTATTTGAA
CTAAAGGCTTTGGAGGAGAAGATACGGACCACGGAGACACAGGTGCTTGTGGCATCTGCACAGAAGAAGCTGC
TAGAGGAAAGACTAAAGCTTGTCTCAGAACTGTGGGATGCTGGGATCAAGGCTGAGCTGCTGTACAAGAAGAA
CCCAAAGCTACTGAACCAGTTACAGTACTGTGAGGAGGCAGGCATCCCACTGGTGGCTATCATCGGCGAGCAGG
AACTCAAGGATGGGGTCATCAAGCTCCGTTCAGTGACGAGCAGGGAAGAGGTGGATGTCCGAAGAGAAGACCT
TGTGGAGGAAATCAAAAGGAGAACAGGCCAGCCCCTCTGCATCTGCTGA⁸⁹⁸

*FIG. 3C*

HRS-SV9:
¹MAERAALEELVKLQGERVRGLKQQKASAEIEEEVAKLLKLKAQLGPDESKQKFVLKTPK⁶⁵
HRS-SV11:
¹MAERAALEELVKLQGERVRGLKQQKASAEIEEEVAKLLKLKAQLGPDESKQKFVLKTPKALEEKIRTTETQVLVAS
AQKKLLEERLKLVSELWDAGIKAELLYKKNPKLLNQLQYCEEAGIPLVAIIGEQELKDGVIKLRSVTSREEVDVRREDL
VEEIKRRTGQPLCIC¹⁷³
HRS-SV14:
¹MAERAALEELVKLQGERVRGLKQQKASAEIEEEVAKLLKLKAQLGPDESKQKFVLKTPKGTRDYSPRQMAVREKV
FDVIIRCFKRHGAEVIDTPVFELKALEEKIRTTETQVLVASAQKKLLEERLKLVSELWDAGIKAELLYKKNPKLLNQLQ
YCEEAGIPLVAIIGEQELKDGVIKLRSVTSREEVDVRREDLVEEIKRRTGQPLCIC²⁹⁸

*FIG. 3D*

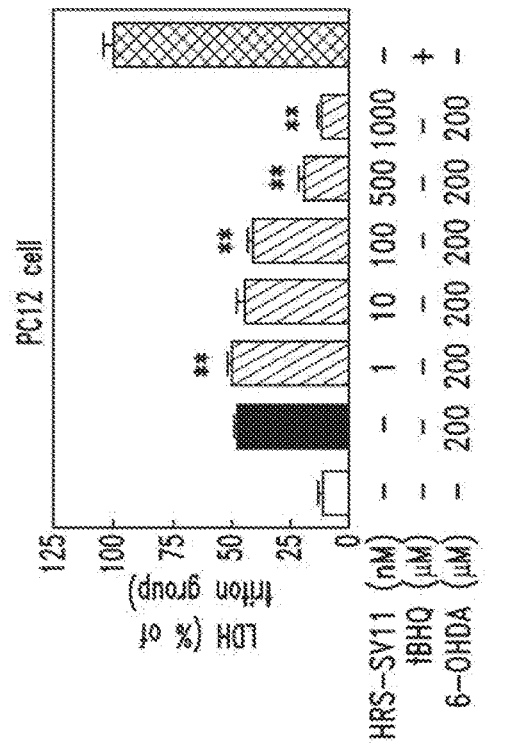
FIG. 9A
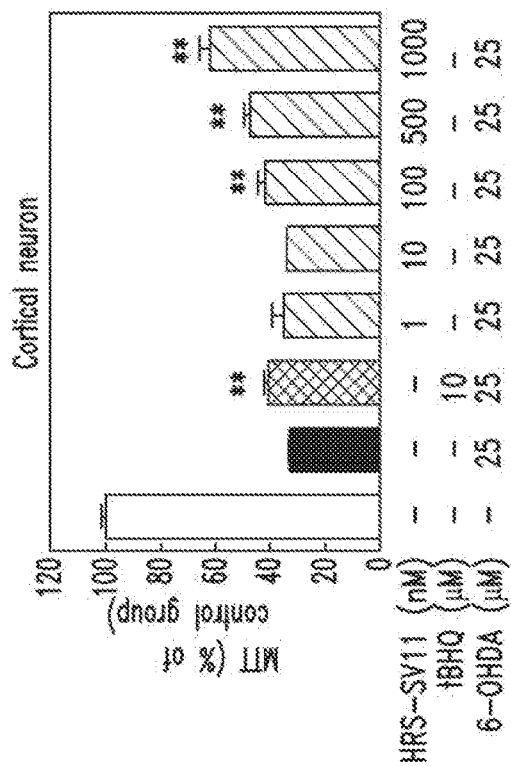
FIG. 9C
FIG. 9B
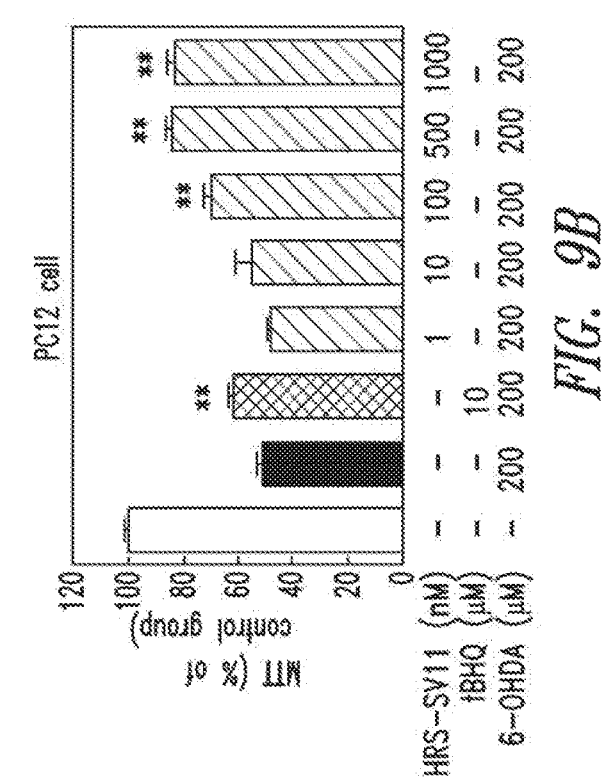
FIG. 9D

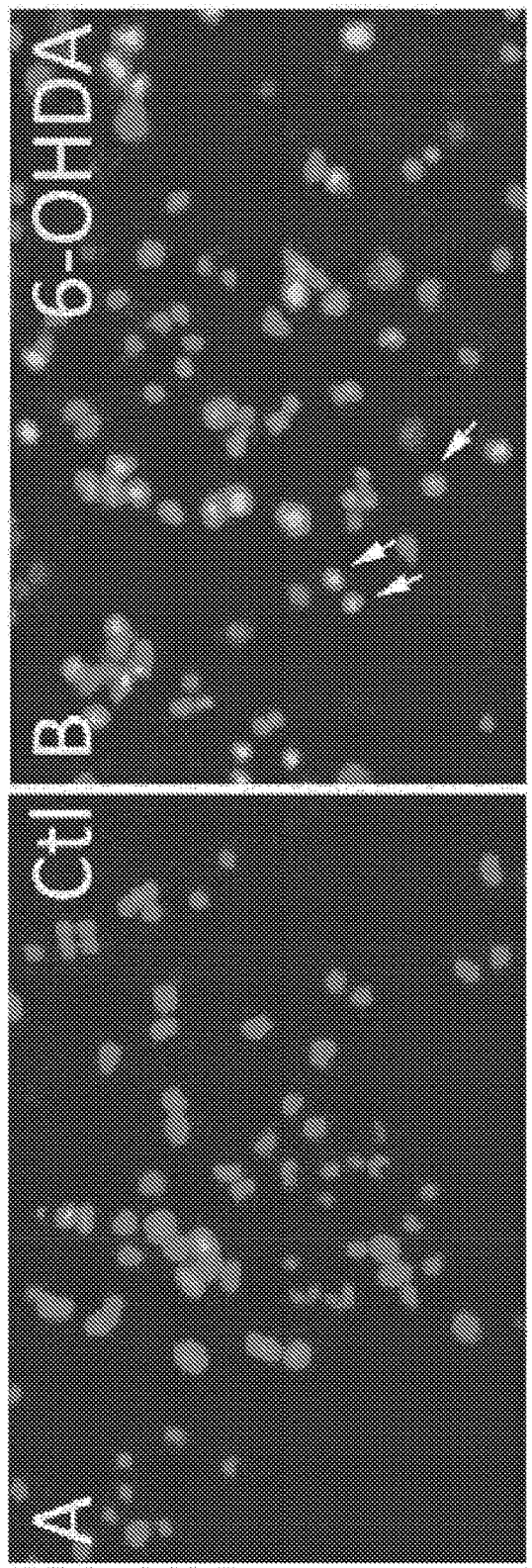
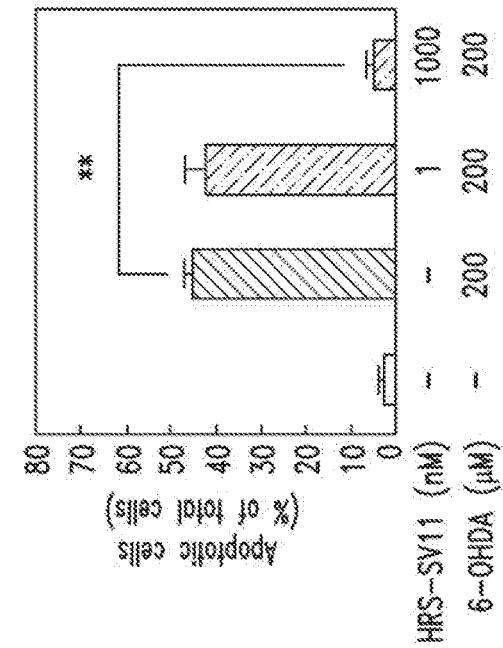
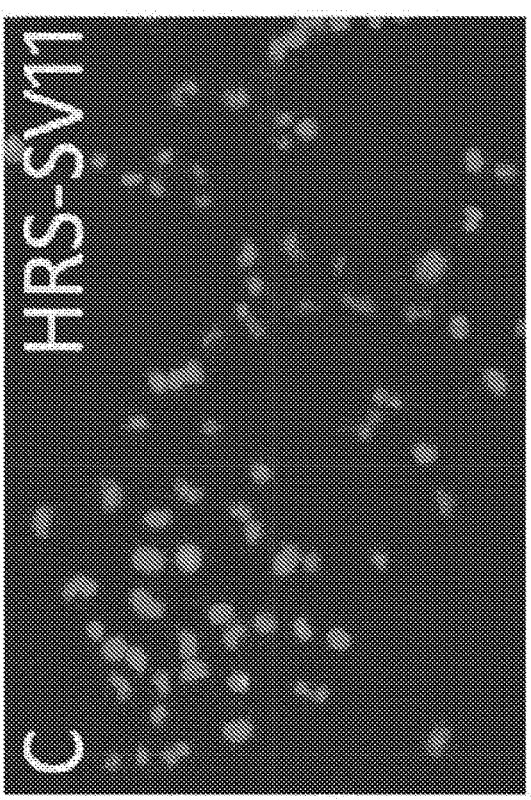
FIG. 12A
FIG. 12B
FIG. 12C
FIG. 12D

FIG. 13A

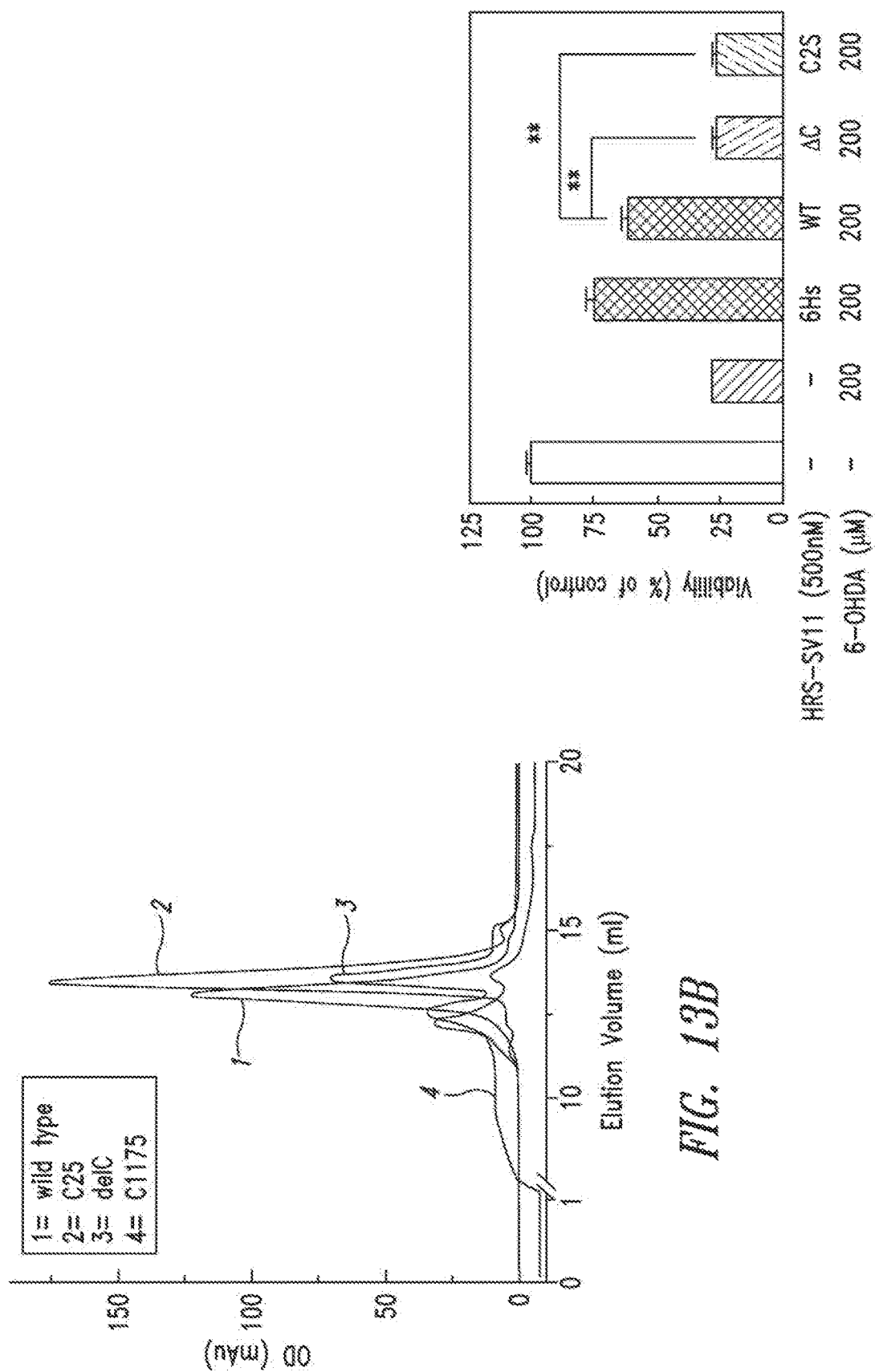

SEQUENCE LISTING

<160> NUMBER OF SEQ ID NOS: 29

<210> SEQ ID NO 1
<211> LENGTH: 24
<212> TYPE: DNA
<213> ORGANISM: Artificial Sequence
<220> FEATURE:
<223> OTHER INFORMATION: Primer

<400> SEQUENCE: 1
agtggacagc cgggatggca gagc                                          24

<210> SEQ ID NO 2
<211> LENGTH: 21
<212> TYPE: DNA
<213> ORGANISM: Artificial Sequence
<220> FEATURE:
<223> OTHER INFORMATION: Primer

<400> SEQUENCE: 2
caggaagtcg cctatctgaa g                                             21

<210> SEQ ID NO 3
<211> LENGTH: 1981
<212> TYPE: DNA
<213> ORGANISM: Homo sapiens

<400> SEQUENCE: 3
tcgatagccg gaagtcatcc ttgctgaggc tggggcaacc accgcaggtc gagacagcag     60
gcggctcaag tggacagccg ggatggcaga gcgtgcggcg ctggaggagc tggtgaaact    120
tcagggagag cgcgtgcgag gcctcaagca gcagaaggcc agcgccgagc tgatcgagga    180
ggaggtggcg aaactcctga aactgaaggc acagctgggt cctgatgaaa gcaaacagaa    240
atttgtgctc aaaaccccca agggcacaag agactatagt ccccggcaga tggcagttcg    300
cgagaaggtg tttgacgtaa tcatccgttg cttcaagcgc cacggtgcag aagtcattga    360
tacacctgta tttgaactaa aggaaacact gatgggaaag tatggggaag actccaagct    420
tatctatgac ctgaaggacc agggcgggga gctcctgtcc cttcgctatg acctcactgt    480 tcctttttgct cggtatttgg caatgaataa actgaccaac attaaacgct accacatagc    540
aaaggtatat cggcgggata cccagccat gacccgtggc cgataccggg aattctacca    600
gtgtgatttt gacattgctg gaacttttga tcccatgatc cctgatgcag agtgcctgaa    660
gatcatgtgc gagatcctga gttcacttca gataggcgac ttcctggtca aggtaaacga    720
tcgacgcatt ctagatggga tgtttgctat ctgtggtgtt tctgcacagca agttccgtac    780 catctgctcc tcagtagaca agctggacaa ggtgtcctgg aagaggtga agaatgagat    840 ggtgggagag aagggccttg cacctgaggt ggctgaccgc attggggact atgtccagca    900
acatggtggg gtatccctgg tggaacagct gctccaggat cctaaactat cccaaaacaa    960
gcaggccttg gagggcctgg agacctgaa gttgctcttt gagtacctga ccctatttgg   1020
cattgatgac aaaatctcct ttgacctgag ccttgctcga gggctggatt actacactgg   1080
ggtgatctat gaggcagtgc tgctacagac cccagcccag gcagggggag agcccctggg   1140
tgtgggcagt gtggctgctg gaggacgcta tgatgggcta gtgggcatgt cgacccccaa   1200
agggcgcaag gtgccatgtg tgggctcag cattggggtg gagcggattt tctccatcgt   1260
ggaacagaga ctagaggctt tggaggagaa gatacgggacc acggagacac aggtgctttgt   1320 ggcatctgca cagaagaagc tgctagagga aagactaaag cttgtctcag aactgtggga   1380

```
tgctgggatc aaggctgagc tgctgtacaa gaagaaccca aagctactga accagttaca    1440
gtactgtgag gaggcaggca tcccactggt ggctatcatc ggcgagcagg aactcaagga    1500
tggggtcatc aagctccgtt cagtgacgag cagggaagag gtggatgtcc gaagagaaga    1560
ccttgtggag gaaatcaaaa ggagaacagg ccagcccctc tgcatctgct gaactgaaca    1620
aactatcaga ggaaaggaag tgggactggc actatttgag gttaagacaa actgcatatg    1680
tacttcaatt gctttgcact tttccgtttc agcggaagac ctgaagagtg gtcagaacag    1740
agcctttgat ttttattatg gttatttat tgattattac tggcaaaaac ggccaggtac    1800 aacaccttt tcatacaagg cccaggaggc ttagtccagt ctgtgctcct gggctacaag    1860
gacccagcct gagatggtcc catctgcagg gccccgcacc agttggagca gatgcctccc    1920
caccaccaat tgccaaaggt ccaataaaat gcctcaacca cggaaaaaaa aaaaaaaaa    1980 a                                                                    1981
```

<210> SEQ ID NO 4
<211> LENGTH: 509
<212> TYPE: PRT
<213> ORGANISM: Homo sapiens

<400> SEQUENCE: 4

```
Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
                20                  25                  30

Glu Glu Val Ala Lys Leu Leu Lys Leu Lys Ala Gln Leu Gly Pro Asp
            35                  40                  45

Glu Ser Lys Gln Lys Phe Val Leu Lys Thr Pro Lys Gly Thr Arg Asp
        50                  55                  60

Tyr Ser Pro Arg Gln Met Ala Val Arg Glu Lys Val Phe Asp Val Ile
65                  70                  75                  80

Ile Arg Cys Phe Lys Arg His Gly Ala Glu Val Ile Asp Thr Pro Val
                85                  90                  95

Phe Glu Leu Lys Glu Thr Leu Met Gly Lys Tyr Gly Glu Asp Ser Lys
            100                 105                 110

Leu Ile Tyr Asp Leu Lys Asp Gln Gly Gly Glu Leu Leu Ser Leu Arg
        115                 120                 125

Tyr Asp Leu Thr Val Pro Phe Ala Arg Tyr Leu Ala Met Asn Lys Leu
    130                 135                 140

Thr Asn Ile Lys Arg Tyr His Ile Ala Lys Val Tyr Arg Arg Asp Asn
145                 150                 155                 160

Pro Ala Met Thr Arg Gly Arg Tyr Arg Glu Phe Tyr Gln Cys Asp Phe
                165                 170                 175

Asp Ile Ala Gly Asn Phe Asp Pro Met Ile Pro Asp Ala Glu Cys Leu
            180                 185                 190

Lys Ile Met Cys Glu Ile Leu Ser Ser Leu Gln Ile Gly Asp Phe Leu
        195                 200                 205

Val Lys Val Asn Asp Arg Arg Ile Leu Asp Gly Met Phe Ala Ile Cys
    210                 215                 220

Gly Val Ser Asp Ser Lys Phe Arg Thr Ile Cys Ser Ser Val Asp Lys
225                 230                 235                 240

Leu Asp Lys Val Ser Trp Glu Glu Val Lys Asn Glu Met Val Gly Glu
                245                 250                 255
```

```
Lys Gly Leu Ala Pro Glu Val Ala Asp Arg Ile Gly Asp Tyr Val Gln
            260                 265                 270

Gln His Gly Gly Val Ser Leu Val Glu Gln Leu Leu Gln Asp Pro Lys
        275                 280                 285

Leu Ser Gln Asn Lys Gln Ala Leu Glu Gly Leu Gly Asp Leu Lys Leu
    290                 295                 300

Leu Phe Glu Tyr Leu Thr Leu Phe Gly Ile Asp Asp Lys Ile Ser Phe
305                 310                 315                 320

Asp Leu Ser Leu Ala Arg Gly Leu Asp Tyr Tyr Thr Gly Val Ile Tyr
                325                 330                 335

Glu Ala Val Leu Leu Gln Thr Pro Ala Gln Ala Gly Glu Glu Pro Leu
            340                 345                 350

Gly Val Gly Ser Val Ala Ala Gly Gly Arg Tyr Asp Gly Leu Val Gly
        355                 360                 365

Met Phe Asp Pro Lys Gly Arg Lys Val Pro Cys Val Gly Leu Ser Ile
    370                 375                 380

Gly Val Glu Arg Ile Phe Ser Ile Val Glu Gln Arg Leu Glu Ala Leu
385                 390                 395                 400

Glu Glu Lys Ile Arg Thr Thr Glu Thr Gln Val Leu Val Ala Ser Ala
                405                 410                 415

Gln Lys Lys Leu Leu Glu Glu Arg Leu Lys Leu Val Ser Glu Leu Trp
            420                 425                 430

Asp Ala Gly Ile Lys Ala Glu Leu Leu Tyr Lys Lys Asn Pro Lys Leu
        435                 440                 445

Leu Asn Gln Leu Gln Tyr Cys Glu Glu Ala Gly Ile Pro Leu Val Ala
    450                 455                 460

Ile Ile Gly Glu Gln Glu Leu Lys Asp Gly Val Ile Lys Leu Arg Ser
465                 470                 475                 480

Val Thr Ser Arg Glu Glu Val Asp Val Arg Arg Glu Asp Leu Val Glu
                485                 490                 495

Glu Ile Lys Arg Arg Thr Gly Gln Pro Leu Cys Ile Cys
            500                 505

<210> SEQ ID NO 5
<211> LENGTH: 183
<212> TYPE: DNA
<213> ORGANISM: Homo sapiens

<400> SEQUENCE: 5
atggcagagc gtgcggcgct ggaggagctg gtgaaacttc agggagagcg cgtgcgaggc    60
ctcaagcagc agaaggccag cgccgagctg atcgaggagg aggtggcgaa actcctgaaa   120
ctgaaggcac agctgggtcc tgatgaaagc aaacagaaat tgtgctcaa aaccccaag    180 tag                                                                 183

<210> SEQ ID NO 6
<211> LENGTH: 60
<212> TYPE: PRT
<213> ORGANISM: Homo sapiens

<400> SEQUENCE: 6

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
```

```
                    35                  40                  45
Glu Ser Lys Gln Lys Phe Val Leu Lys Thr Pro Lys
    50                  55                  60

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
atagtgccag tcccacttcc                                                     20

<210> SEQ ID NO 8
<211> LENGTH: 516
<212> TYPE: DNA
<213> ORGANISM: Homo sapiens

<400> SEQUENCE: 8
atggcagagc gtgcggcgct ggaggagctg gtgaaacttc agggagagcg cgtgcgaggc         60
ctcaagcagc agaaggccag cgccgagctg atcgaggagg aggtggcgaa actcctgaaa       120
ctgaaggcac agctgggtcc tgatgaaagc aaacagaaat ttgtgctcaa acccccaag        180 gctttggagg agaagatacg gaccacggag acacaggtgc ttgtggcatc tgcacagaag       240
aagctgctag aggaaagact aaagcttgtc tcagaactgt gggatgctgg gatcaaggct       300
gagctgctgt acaagaagaa cccaaagcta ctgaaccagt tacagtactg tgaggaggca       360
ggcatcccac tggtggctat catcggcgag caggaactca aggatggggt catcaagctc       420
cgttcagtga cgagcaggga gaggtggat gtccgaagag aagaccttgt ggaggaaatc        480
aaaaggagaa caggccagcc cctctgcatc tgctga                                 516

<210> SEQ ID NO 9
<211> LENGTH: 171
<212> TYPE: PRT
<213> ORGANISM: Homo sapiens

<400> SEQUENCE: 9

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
                20                  25                  30

Glu Glu Val Ala Lys Leu Leu Lys Leu Lys Ala Gln Leu Gly Pro Asp
            35                  40                  45

Glu Ser Lys Gln Lys Phe Val Leu Lys Thr Pro Lys Ala Leu Glu Glu
    50                  55                  60

Lys Ile Arg Thr Thr Glu Thr Gln Val Leu Val Ala Ser Ala Gln Lys
65                  70                  75                  80

Lys Leu Leu Glu Glu Arg Leu Lys Leu Val Ser Glu Leu Trp Asp Ala
                85                  90                  95

Gly Ile Lys Ala Glu Leu Leu Tyr Lys Lys Asn Pro Lys Leu Leu Asn
            100                 105                 110

Gln Leu Gln Tyr Cys Glu Glu Ala Gly Ile Pro Leu Val Ala Ile Ile
        115                 120                 125

Gly Glu Gln Glu Leu Lys Asp Gly Val Ile Lys Leu Arg Ser Val Thr
    130                 135                 140

Ser Arg Glu Glu Val Asp Val Arg Arg Glu Asp Leu Val Glu Glu Ile
```

```
                    145                 150                 155                 160
Lys Arg Arg Thr Gly Gln Pro Leu Cys Ile Cys
            165                 170

<210> SEQ ID NO 10
<211> LENGTH: 636
<212> TYPE: DNA
<213> ORGANISM: Homo sapiens

<400> SEQUENCE: 10
atggcagagc gtgcggcgct ggaggagctg gtgaaacttc agggagagcg cgtgcgaggc      60
ctcaagcagc agaaggccag cgccgagctg atcgaggagg aggtggcgaa actcctgaaa     120
ctgaaggcac agctgggtcc tgatgaaagc aaacagaaat ttgtgctcaa accccccaag     180
ggcacaagag actatagtcc ccggcagatg gcagttcgcg agaaggtgtt tgacgtaatc     240
atccgttgct tcaagcgcca cggtgcagaa gtcattgata cacctgtatt tgaactaaag     300
gctttggagg agaagatacg gaccacggag acacaggtgc ttgtggcatc tgcacagaag     360
aagctgctag aggaaagact aaagcttgtc tcagaactgt gggatgctgg gatcaaggct     420
gagctgctgt acaagaagaa cccaaagcta ctgaaccagt tacagtactg tgaggaggca     480
ggcatcccac tggtggctat catcggcgag caggaactca aggatggggt catcaagctc     540
cgttcagtga cgagcaggga gaggtggat gtccgaagag aagaccttgt ggaggaaatc     600
aaaaggagaa caggccagcc cctctgcatc tgctga                              636

<210> SEQ ID NO 11
<211> LENGTH: 211
<212> TYPE: PRT
<213> ORGANISM: Homo sapiens

<400> SEQUENCE: 11

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr Arg Asp
    50                  55                  60

Tyr Ser Pro Arg Gln Met Ala Val Arg Glu Lys Val Phe Asp Val Ile
65                  70                  75                  80

Ile Arg Cys Phe Lys Arg His Gly Ala Glu Val Ile Asp Thr Pro Val
                85                  90                  95

Phe Glu Leu Lys Ala Leu Glu Glu Lys Ile Arg Thr Thr Glu Thr Gln
            100                 105                 110

Val Leu Val Ala Ser Ala Gln Lys Lys Leu Leu Glu Glu Arg Leu Lys
        115                 120                 125

Leu Val Ser Glu Leu Trp Asp Ala Gly Ile Lys Ala Glu Leu Leu Tyr
    130                 135                 140

Lys Lys Asn Pro Lys Leu Leu Asn Gln Leu Gln Tyr Cys Glu Glu Ala
145                 150                 155                 160

Gly Ile Pro Leu Val Ala Ile Ile Gly Glu Gln Glu Leu Lys Asp Gly
                165                 170                 175

Val Ile Lys Leu Arg Ser Val Thr Ser Arg Glu Glu Val Asp Val Arg
            180                 185                 190
```

-continued

```
Arg Glu Asp Leu Val Glu Glu Ile Lys Arg Arg Thr Gly Gln Pro Leu
        195                 200                 205
Cys Ile Cys
    210

<210> SEQ ID NO 12
<211> LENGTH: 20
<212> TYPE: DNA
<213> ORGANISM: Artificial Sequence
<220> FEATURE:
<223> OTHER INFORMATION: Primer sequence hsH1-E2F1

<400> SEQUENCE: 12
tgaaactgaa ggcacagctg                                              20

<210> SEQ ID NO 13
<211> LENGTH: 20
<212> TYPE: DNA
<213> ORGANISM: Artificial Sequence
<220> FEATURE:
<223> OTHER INFORMATION: Primer sequence hsH1-E13R1

<400> SEQUENCE: 13
tcttctcttc ggacatccac                                              20

<210> SEQ ID NO 14
<211> LENGTH: 22
<212> TYPE: DNA
<213> ORGANISM: Artificial Sequence
<220> FEATURE:
<223> OTHER INFORMATION: Primer sequence rnH1-E02F1

<400> SEQUENCE: 14
aacagaagtt cgtcctcaaa ac                                           22

<210> SEQ ID NO 15
<211> LENGTH: 22
<212> TYPE: DNA
<213> ORGANISM: Artificial Sequence
<220> FEATURE:
<223> OTHER INFORMATION: Primer sequence rnH1-E12J13R2

<400> SEQUENCE: 15
tccacctctt ctctgctcgt ca                                           22

<210> SEQ ID NO 16
<211> LENGTH: 60
<212> TYPE: PRT
<213> ORGANISM: Pongo abelii

<400> SEQUENCE: 16

Asn Gln Leu Gln Tyr Cys Glu Glu Ala Gly Ile Pro Leu Val Ala Ile
1               5                   10                  15

Ile Gly Glu Gln Glu Leu Glu Asp Gly Val Ile Lys Leu Arg Ser Val
            20                  25                  30

Thr Ser Arg Glu Glu Val Asp Val Arg Arg Glu Asp Leu Val Glu Glu
        35                  40                  45

Ile Lys Arg Arg Thr Gly Gln Pro Leu Cys Ile Cys
    50                  55                  60

<210> SEQ ID NO 17
<211> LENGTH: 60
<212> TYPE: PRT
<213> ORGANISM: Bos taurus
```

<400> SEQUENCE: 17

Asn Gln Leu Gln Tyr Cys Glu Glu Thr Gly Ile Pro Leu Val Ala Ile
1               5                   10                  15

Ile Gly Glu Gln Glu Leu Lys Asp Gly Val Ile Lys Leu Arg Ser Val
            20                  25                  30

Ala Ser Arg Glu Glu Val Asp Val Arg Arg Glu Asp Leu Val Glu Glu
        35                  40                  45

Ile Lys Arg Arg Thr Ser Gln Pro Leu Cys Ile Cys
    50                  55                  60

<210> SEQ ID NO 18
<211> LENGTH: 60
<212> TYPE: PRT
<213> ORGANISM: Mus musculus

<400> SEQUENCE: 18

Asn Gln Leu Gln Tyr Cys Glu Glu Ala Gly Ile Pro Leu Val Ala Ile
1               5                   10                  15

Ile Gly Glu Gln Glu Leu Lys Asp Gly Val Ile Lys Leu Arg Ser Val
            20                  25                  30

Ala Ser Arg Glu Glu Val Asp Val Gln Arg Glu Asp Leu Val Glu Glu
        35                  40                  45

Ile Arg Arg Arg Thr Asn Gln Pro Leu Ser Ile Cys
    50                  55                  60

<210> SEQ ID NO 19
<211> LENGTH: 60
<212> TYPE: PRT
<213> ORGANISM: Mesocricetus auratus

<400> SEQUENCE: 19

Asn Gln Leu Gln Tyr Cys Glu Glu Thr Gly Ile Pro Leu Val Ala Ile
1               5                   10                  15

Ile Gly Glu Gln Glu Leu Lys Asp Gly Val Ile Lys Leu Arg Ser Val
            20                  25                  30

Ala Ser Arg Glu Glu Val Asp Val Arg Arg Glu Asp Leu Val Glu Glu
        35                  40                  45

Ile Arg Arg Arg Thr Asn Gln Pro Leu Tyr Val Cys
    50                  55                  60

<210> SEQ ID NO 20
<211> LENGTH: 55
<212> TYPE: PRT
<213> ORGANISM: Fugu rubripes

<400> SEQUENCE: 20

Ser Gln Leu Gln His Cys Glu Glu Ser Gly Ile Pro Leu Val Ala Ile
1               5                   10                  15

Leu Gly Glu Gln Glu Leu Lys Asn Gly Val Val Lys Leu Arg Asn Val
            20                  25                  30

Ala Thr Arg Asp Glu Val Asp Ile Ser Arg Ala Asp Leu Ile Ala Glu
        35                  40                  45

Ile Lys Lys Arg Thr Ser Ala
    50                  55

<210> SEQ ID NO 21
<211> LENGTH: 56
<212> TYPE: PRT

<213> ORGANISM: Caenorhabditis elegans

<400> SEQUENCE: 21

Thr Gln Phe Gln Tyr Ala Glu Glu Arg Arg Ile Pro Leu Ala Ile Val
1               5                   10                  15
Ile Gly Glu Gln Glu Leu Lys Asp Gly Val Val Lys Leu Arg Asn Val
            20                  25                  30
Val Thr Arg Asp Glu Gln Thr Ile Lys Leu Asp Gln Leu Ile Thr Ala
        35                  40                  45
Val Arg Asp Thr Leu Ala Ala Leu
    50                  55

<210> SEQ ID NO 22
<211> LENGTH: 58
<212> TYPE: PRT
<213> ORGANISM: Dictyostelium discoideum

<400> SEQUENCE: 22

Ala Gln Leu Asn Thr Ala Asp Glu Ser Asn Ile Pro Leu Ile Ile Ile
1               5                   10                  15
Ile Gly Lys Ser Glu Val Glu Thr Asn Ser Leu Ser Val Lys Thr Met
            20                  25                  30
His Asp Arg Lys Gln Val Ser Ile Glu Arg Ser Asn Phe Thr Val Lys
        35                  40                  45
Ile Lys Glu Ile Leu Ser Thr Ile Pro Lys
    50                  55

<210> SEQ ID NO 23
<211> LENGTH: 56
<212> TYPE: PRT
<213> ORGANISM: Oryza sativa subsp. japonica

<400> SEQUENCE: 23

Asn His Leu Lys Tyr Ala Thr Gln Ser Gly Ile Pro Trp Met Val Leu
1               5                   10                  15
Val Gly Glu Ser Glu Ile Ser Ser Gly Lys Val Lys Leu Lys Asn Leu
            20                  25                  30
Ala Ala Ser Gln Glu Glu Glu Val Asp Arg Thr Glu Phe Ala Gln Val
        35                  40                  45
Leu Lys Gln Lys Leu Arg Asn Pro
    50                  55

<210> SEQ ID NO 24
<211> LENGTH: 53
<212> TYPE: DNA
<213> ORGANISM: Homo sapiens

<400> SEQUENCE: 24
aagtcattga tacacctgta tttgaactaa aggaaacact gatgggaaag tat        53

<210> SEQ ID NO 25
<211> LENGTH: 18
<212> TYPE: PRT
<213> ORGANISM: Homo sapiens

<400> SEQUENCE: 25

Glu Val Ile Asp Thr Pro Val Phe Glu Leu Lys Glu Thr Leu Met Gly
1               5                   10                  15
Lys Tyr

```
<210> SEQ ID NO 26
<211> LENGTH: 62
<212> TYPE: DNA
<213> ORGANISM: Homo sapiens

<400> SEQUENCE: 26
gtcattgata cacctgtatt tgaactaaag gctttggagg agaagatacg gaccacggag      60
ac                                                                    62

<210> SEQ ID NO 27
<211> LENGTH: 49
<212> TYPE: DNA
<213> ORGANISM: Homo sapiens

<400> SEQUENCE: 27
ggaacagaga ctagaggctt tggaggagaa gatacggacc acggagaca                 49

<210> SEQ ID NO 28
<211> LENGTH: 16
<212> TYPE: PRT
<213> ORGANISM: Homo sapiens

<400> SEQUENCE: 28

Glu Gln Arg Leu Glu Ala Leu Glu Glu Lys Ile Arg Thr Thr Glu Thr
1               5                   10                  15

<210> SEQ ID NO 29
<211> LENGTH: 60
<212> TYPE: PRT
<213> ORGANISM: Homo sapiens

<400> SEQUENCE: 29

Asn Gln Leu Gln Tyr Cys Glu Glu Ala Gly Ile Pro Leu Val Ala Ile
1               5                   10                  15

Ile Gly Glu Gln Glu Leu Lys Asp Gly Val Ile Lys Leu Arg Ser Val
            20                  25                  30

Thr Ser Arg Glu Glu Val Asp Val Arg Arg Glu Asp Leu Val Glu Glu
        35                  40                  45

Ile Lys Arg Arg Thr Gly Gln Pro Leu Cys Ile Cys
    50                  55                  60
```

COMPOSITIONS AND METHODS COMPRISING HISTIDYL-TRNA SYNTHETASE SPLICE VARIANTS HAVING NON-CANONICAL BIOLOGICAL ACTIVITIES

CROSS REFERENCE TO RELATED APPLICATIONS

This application is a Continuation of U.S. application Ser. No. 16/005,045, filed Jun. 11, 2018; which is a Continuation of U.S. application Ser. No. 15/257,353, filed Sep. 6, 2016, now U.S. Pat. No. 10,017,582, issued Jul. 10, 2018; which is a Continuation of U.S. application Ser. No. 14/262,272, filed Apr. 25, 2014, now U.S. Pat. No. 9,605,265, issued Mar. 28, 2017; which is a Continuation of U.S. application Ser. No. 13/766,659, filed Feb. 13, 2013, now U.S. Pat. No. 8,753,638, issued Jun. 17, 2014; which is a Continuation of U.S. application Ser. No. 12/725,272, filed Mar. 16, 2010, now U.S. Pat. No. 8,404,242, issued Mar. 26, 2013; which claims the benefit under 35 U.S.C. § 119(e) of U.S. Provisional Patent Application 61/160,630, filed Mar. 16, 2009, and U.S. Provisional Patent Application 61/239,747, filed Sep. 3, 2009, each of which is incorporated by reference in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is ATYR-015_07US_ST25.txt. The text file is about 20 KB, was created on Nov. 18, 2019, and is being submitted electronically via EFS-Web.

BACKGROUND OF THE INVENTION

Field of the Invention

The present invention relates generally to histidyl-tRNA synthetase (HRS) splice variant polynucleotides and polypeptides, compositions comprising such polynucleotides and polypeptides, and methods of using same.

Description of the Related Art

Aminoacyl-tRNA synthetase (AARS) proteins, which catalyze the aminoacylation of tRNA molecules, are essential for decoding genetic information during the process of translation. Each of the eukaryotic tRNA synthetases consists of a core enzyme, which is closely related to the prokaryotic tRNA synthetase, as well as additional domains that are appended to the amino-terminal end, carboxyl-terminal end or inserted into a region internal to the core enzyme. Human tyrosyl-tRNA synthetase (TyrRS), for example, has a carboxyl-terminal domain that is not part of prokaryotic and lower eukaryotic TyrRS molecules.

Several aminoacyl-tRNA synthetases have been demonstrated to have non-canonical functions distinct from their involvement in translation. For example, Mini-tyrosyl tRNA synthetase (mini-TyrRS), the N-terminal domain of TyrRS which corresponds to amino acid residues 1-364 and is cleaved by polymorphonuclear cell elastase and plasmin, is a member of the aminoacyl tRNA synthetase "AARS" multifunction cytokine-like proteins and peptides. In vitro, Mini-TyrRS has been shown to stimulate neutrophil activation and chemotaxis, endothelial cell proliferation and migration, and is pro-angiogenic in chick chorioallantoic membrane (CAM) and mouse matrigel assays. Mini-TyrRS has an ELR motif that, like CXC-chemokines such as IL-8, confers its chemokine and angiogenic activities. Like other ELR-containing cytokines, mutation of this motif inhibits mini-TyrRS binding and stimulation of leukocytes and angiogenesis.

In addition, truncated forms of TrpRS have been demonstrated to have angiogenic properties. In normal human cells, there are two forms of TrpRS that can be detected: a major form consisting of the full-length molecule (amino acid residues 1-471) and a minor truncated form. The minor form is generated by the deletion of an amino-terminal domain through alternative splicing of the pre-mRNA. The amino-terminus of mini-TrpRS has been determined to be the methionine residue at position 48 of the full-length TrpRS molecule. Alternatively, truncated TrpRS can be generated by proteolysis. For example, bovine TrpRS is highly expressed in the pancreas and is secreted into the pancreatic juice, thus resulting in the production of a truncated TrpRS molecule. Additional studies indicate that mini-TrpRS inhibits VEGF-induced cell proliferation and migration (Wakasugi et al., Proc. Natl. Acad. Sci. 99: 173-177 (2002)). In particular, a chick CAM assay shows that mini-TrpRS blocks angiogenic activity of VEGF. In contrast, the full-length TrpRS does not inhibit angiogenesis. Thus, removal of the first 48 amino acid residues exposes the anti-angiogenic activity of TrpRS. Therefore, as with TyrRS, certain forms of TrpRS possess activities other than the aminoacylation of tRNA.

Given these observations of non-canonical and therapeutically relevant activities associated with alternative forms of TyrRS and TrpRS, there is a need to identify biologically relevant forms and/or activities of other aminoacyl-tRNA synthetase proteins in order to exploit the full therapeutic potential of this family of proteins. Accordingly, the present invention addresses these needs and offers other related advantages.

SUMMARY OF THE INVENTION

The present invention relates generally to isolated HRS splice variant polypeptides having non-canonical activities; HRS splice variant polynucleotides encoding HRS splice variant polypeptides; binding agents that bind HRS polypeptides; analogs, variants and fragments of HRS polypeptides and polynucleotides, as well as compositions and methods of making and using any of the foregoing.

Therefore, according to one aspect, the present invention provides isolated HRS splice variant polypeptides having at least one non-canonical biological activity, as well active fragments and variants thereof. "Non-canonical" activity," as used herein, refers generally to an activity possessed by a HRS polypeptide of the invention that is other than aminoacylation and, more specifically, other than the addition of histidine onto a tRNA$^{His}$ molecule. As described herein, in certain embodiments, a non-canonical biological activity exhibited by a HRS polypeptide of the invention may include, but is not limited to, modulation of cytokine production, modulation of cell proliferation, modulation of apoptosis, modulation of cell signaling, modulation of angiogenesis, modulation of cell migration, modulation of cell binding, modulation of cellular metabolism, and the like.

In one illustrative embodiment, the HRS splice variant polypeptide of the invention is a HRS fragment comprising at least the WHEP domain of HRS, e.g., amino acid residues 3-43 of the human full length HRS protein. In another embodiment, the HRS splice variant polypeptide of the invention is a HRS fragment comprising at least the anticodon binding domain of HRS, e.g., amino acid residues 406-501 of the full length human HRS protein. In yet another embodiment, the HRS splice variant polypeptide is a HRS fragment that lacks a functional aminoacylation domain, e.g., amino acid residues 54-398 of the human full length HRS protein. In a more particular embodiment, the HRS splice variant polypeptide comprises at least the WHEP domain and the anticodon binding domain but lacks a functional aminoacylation domain.

In a more specific embodiment, the HRS polypeptide of the invention comprises a sequence set forth in SEQ ID NOs: 6, 9 or 11, or is a contiguous fragment of a polypeptide set forth in SEQ ID NOs: 6, 9 or 11. Illustratively, the fragments may be of essentially any length, provided they retain at least one non-canonical biological activity of interest. For example, as further described herein, such a fragment may comprise at least about 5, 10, 15, 20, 25, 50, 75 or 80, or more, contiguous amino acid residues of SEQ ID NOs: 6, 9 or 11.

In further embodiments of the invention, a HRS polypeptide comprises an active variant (i.e., retains at least one non-canonical biological activity of interest) of a sequence set forth in SEQ ID NOs: 6, 9 or 11. In a more specific embodiment, the active variant is a polypeptide having at least 70%, 80%, 90%, 95% or 99% identity along its length to a sequence set forth in SEQ ID NOs: 6, 9 or 11.

In another particular embodiment, the HRS polypeptide of the invention is not a polypeptide consisting of residues 1-48 of the full length human HRS protein.

According to another aspect of the invention, there are provided fusion proteins comprising at least one HRS polypeptide as described herein and a heterologous fusion partner.

According to another aspect of the invention, there are provided isolated polynucleotides encoding the polypeptides and fusion proteins as described herein, as well as expression vectors comprising such polynucleotides, and host cell comprising such expression vectors. Also included are oligonucleotides that specifically hybridize to an HRS polynucleotide, such as the polynucleotides of SEQ ID NOS:5, 8, or 10. In certain embodiments, the oligonucleotide is a primer, a probe, or an antisense oligonucleotide. Other embodiments relate to RNAi agents that target an HRS polynucleotide. In certain embodiments, the oligonucleotides or RNAi agents specifically hybridize to or otherwise target a splice junction that is unique to the HRS splice variant.

According to another aspect of the invention, there are provided binding agents (e.g., antibodies and antigen-binding fragments thereof) that have binding specificity for a HRS splice variant polypeptide of the invention (e.g., SEQ ID NOs: 6, 9, or 11), or one of its cellular binding partners. In certain embodiments, the binding agent is an antibody, an antigen-binding fragment thereof, a peptide, a peptide mimetic, a small molecule, or an aptamer. In some embodiments, the binding agent antagonizes a non-canonical activity of the HRS polypeptide. In other embodiments, the binding agent agonizes a non-canonical activity of the HRS polypeptide.

According to yet another aspect of the invention, there are provided compositions, e.g., pharmaceutical compositions, comprising physiologically acceptable carriers and at least one of the isolated polypeptides, fusion proteins, antibodies, isolated polynucleotides, expression vectors, host cells, etc., of the invention, as described herein.

Also included are methods of determining presence or levels of a polynucleotide sequence of a HRS splice variant in a sample, comprising contacting the sample with one or more oligonucleotides that specifically hybridize to an HRS splice variant as set forth SEQ ID NOS:5, 8, or 10, detecting the presence or absence of the oligonucleotides in the sample, and thereby determining the presence or levels of the polynucleotide sequence of the HRS splice variant.

Also provided are methods of determining presence or levels of a polynucleotide sequence of a HRS splice variant in a sample, comprising contacting the sample with at least two oligonucleotides that specifically amplify an HRS splice variant as set forth in SEQ ID NOS:5, 8, or 10, performing an amplification reaction, detecting the presence or absence of an amplified product, and thereby determining presence or levels of the polynucleotide sequence of the HRS splice variant. In some embodiments, the oligonucleotide(s) specifically hybridize to or specifically amplify a splice junction that is unique to the HRS splice variant. Certain embodiments include comparing the presence or levels of the HRS splice variant to a control sample or a predetermined value. Specific embodiments include characterizing the state of the sample to distinguish it from the control. In particular embodiments, the sample and control comprise a cell or tissue, and the method comprises distinguishing between cells or tissues of different species, cells of different tissues or organs, cells at different cellular developmental states, cells at different cellular differentiation states, or healthy and diseased cells.

Also included are methods of identifying a compound that specifically binds to a HRS splice variant polypeptide as set forth in SEQ ID NOS:6, 9, or 11, or one or more of its cellular binding partners, comprising a) combining the HRS polypeptide or its cellular binding partner or both with at least one test compound under suitable conditions, and b) detecting binding of the HRS polypeptide or its cellular binding partner or both to the test compound, thereby identifying a compound that specifically binds to the HRS polypeptide or its cellular binding partner or both. In certain embodiments, the test compound is a polypeptide or peptide, an antibody or antigen-binding fragment thereof, a peptide mimetic, or a small molecule. In some embodiments, the test compound agonizes a non-canonical biological activity of the HRS polypeptide or its cellular binding partner. In other embodiments, the test compound antagonizes a non-canonical biological activity of the HRS polypeptide or its cellular binding partner. Also included are compounds identified by any of the methods provided herein.

Also provided by the present invention, in other aspects, are methods for modulating a cellular activity by contacting a cell or tissue with a composition of the invention, as described herein. For example, in certain embodiments, the cellular activity to be modulated is selected from the group consisting of cytokine production, cell proliferation, apoptosis, cell signaling, cellular metabolism, angiogenesis, cell migration, cell binding, and the like. In a specific embodiment, the method is a method for modulating cytokine production. In a more specific embodiment, the method is a method for modulating IL-2 production and/or secretion. In some embodiments, the method is a method for modulating TNF-α production and/or secretion. In other embodiments, the method is a method for modulating MIP1-α production and/or secretion.

In certain embodiments, the cellular activity is cytokine receptor activity. In specific embodiments, the cytokine receptor is CCR1. In certain embodiments, the cellular activity is cell migration. Some embodiments include reducing cell migration of monocytes. In certain embodiments, the cellular activity is cell signaling through Toll-like receptors (TLR)s.

In other aspects, the present invention provides methods for treating a disease, disorder or other condition in a subject in need thereof by administering a composition according to the present invention. By way of illustration, such diseases, disorders or conditions may include, but are not limited to, cancer, inflammatory disease, immune disease (including autoimmune disease) and/or conditions associated with abnormal angiogenesis.

In certain embodiments, the condition is a neurological condition. In specific embodiments, the neurological condition is associated with 6-hydroxydopamine (6-OHDA)-induced neuron death. In certain embodiments, the condition is an inflammatory disease. In specific embodiments, the inflammatory disease is arthritic gout or inflammatory bowel disease.

In still other aspects, the polypeptides, antibodies and/or other compositions of the present invention may be used in essentially any type of screening assay known and available in the art. For example, compositions of the invention (e.g., polypeptides, polynucleotides and/or antibodies) may be used in conjunction with essentially any known screening methodology in order to identify suitable cell types and/or disease conditions amenable to treatment according to the present invention. In other examples, compositions of the invention (e.g., polypeptides, polynucleotides and/or antibodies) may be used in conjunction with known screening methodologies in order to identify binding partners, competitive inhibitors and/or other cellular effectors that mediate or modulate, either directly or indirectly, the non-canonical activities of the compositions herein. For example, in a particular embodiment, a screening method is provided for identifying test compounds as inhibitors, or alternatively, potentiators, of an interaction between a composition of the invention and one or more of its binding partners, cellular effectors and/or cell types subject to modulation. This may include, for example, steps of forming a reaction mixture including: (i) a composition of the invention, (ii) a binding partner, cellular effector and/or cell type known to be modulated by said composition, and (iii) a test compound; and detecting interaction of the test compound with the binding partner, cellular effector and/or cell type. A statistically significant change (potentiation or inhibition) in activity or modulation in the presence of the test compound, relative to the interaction in the absence of the test compound, indicates a potential agonist (mimetic or potentiator) or antagonist (inhibitor) of activity.

BRIEF DESCRIPTION OF SEQUENCE IDENTIFIERS

SEQ ID NO: 1 is a primer sequence (HRS-BPF).
SEQ ID NO: 2 is a primer sequence (HRS-P1R).
SEQ ID NO: 3 is the nucleic acid sequence of the HRS gene (NM_002109.3).
SEQ ID NO: 4 is the amino acid sequence of the full length HRS protein (NP_002100.2)
SEQ ID NO: 5 is a nucleic acid coding sequence of the HRS-SV9 splice variant.
SEQ ID NO: 6 is the amino acid sequence of the HRS-SV9 splice variant polypeptide encoded by SEQ ID NO:5.
SEQ ID NO: 7 is a primer sequence (HRS-3'-UTR).
SEQ ID NO: 8 is a nucleic acid coding sequence of the HRS-SV11 splice variant.
SEQ ID NO: 9 is the amino acid sequence of the HRS-SV11 splice variant polypeptide encoded by SEQ ID NO:8.
SEQ ID NO:10 is a nucleic acid coding sequence of the HRS-SV14 splice variant.
SEQ ID NO:11 is the amino acid sequence of the HRS-SV14 splice variant polypeptide encoded by SEQ ID NO:10.
SEQ ID NO:12 is a primer sequence (hsH1-E2F1).
SEQ ID NO:13 is a primer sequence (hsH1-E13R1).
SEQ ID NO:14 is a primer sequence (rnH1-E02F1).
SEQ ID NO:15 is a primer sequence (rnH1-E12J13R2).
SEQ ID NO:16 is amino acids 112-171 of HRS from *Pongo abelii* (orangutan).
SEQ ID NO:17 is amino acids 112-171 of bovine HRS.
SEQ ID NO:18 is amino acids 112-171 of mouse HRS.
SEQ ID NO:19 is amino acids 112-171 of HRS from *Mesocricetus auratus* (golden hamster).
SEQ ID NO:20 is amino acids 112-166 of HRS from *Fugu rubripes* (Japanese puffer fish).
SEQ ID NO:21 is amino acids 112-167 of HRS from *Caenorhabditis elegans*.
SEQ ID NO:22 is amino acids 112-169 of HRS from *Dictyostelium discoideum*.
SEQ ID NO:23 is amino acids 112-167 of HRS from *Oryza sativa* subsp. *japonica* (rice).
SEQ ID NO:24 is a portion of the coding sequence of exons 3 and 4 of human HRS.
SEQ ID NO:25 is a portion of the amino acid sequence of exons 3 and 4 of human HRS.
SEQ ID NO:26 is a portion of the coding sequence of exons 3 and 4 of human HRS.
SEQ ID NO:27 is a portion of the coding sequence of exons 10 and 11 of human HRS.
SEQ ID NO:28 is a portion of the amino acid sequence of exons 10 and 11 of human HRS.
SEQ ID NO:29 is amino acids 112-171 of HRS-SV11.

BRIEF DESCRIPTION OF THE DRAWINGS

FIG. 1A shows an illustration of an mRNA transcript of the HRS gene and primer positions for PCR reactions (BPF: forward primer, P4R: reverse primer). FIG. 1B shows a gel photo of PCR reaction products from human skeletal muscle, IMR32 cells and HEK293T cells. The upper arrow points to a DNA fragment amplified from the HRS-SV9 transcript. The lower arrow points to a DNA fragment amplified from HRS reference sequence.

FIG. 2A shows an illustration of an mRNA transcript of the HRS gene and primer positions for PCR reactions (BPF: forward primer, HRS-3'UTR: reverse primer). FIG. 2B shows a gel photo of PCR reaction products from IMR32 cells. The lower arrow points to a DNA fragment amplified from the HRS-SV11 transcript. The upper arrow points to a DNA fragment amplified from the HRS reference sequence. FIG. 2C shows that the HRS-SV11 splice variant transcript was identified in human brain tissue.

FIGS. 3A-D illustrate mRNA transcripts and protein sequences of wild type, full length HRS (HRS ref), HRS-SV9, HRS-SV11, and HRS-SV14. FIG. 3A shows an illustration of mRNA transcripts showing that HRS-SV9 has an insertion from Intron 2 and HRS-SV11 has a deletion from Exon 3 to Exon 10. FIG. 3B shows protein structural information encoded by the mRNA transcripts, showing that HRS-SV9 has only the first 60 amino acids of HRS, including the intact WHEP domain, whereas HRS-SV11 has a deletion of the whole aminoacylation domain, leaving only the WHEP and anticodon domains. FIGS. 3C and 3D show the nucleic acid coding sequences (SEQ ID NOs: 5, 8, and 10) and encoded protein sequences (SEQ ID NOS: 6, 9, and 11) for HRS-SV9, HRS-SV11, and HRS-SV14, respectively.

FIG. 4A shows an immunoblot with the N-terminal HRS antibody (against amino acids 1-97). The reference band is shown by the upper arrow of FIG. 4A. The lower arrow of FIG. 4A points to a band whose size is consistent with predicted size of the HRS-SV11 splice variant polypeptide. FIG. 4B shows an immunoblot with the C-terminal HRS antibody (against 50-200 amino acids near the C-terminus). The upper arrow points to the reference protein, while lower arrow points to a band with similar size as seen with the N-terminal antibody.

FIG. 5A shows results for HEK293T cells, C2C12 myoblasts (MB) and C2C12 myotubes (MT); the lower arrow points to a band having a size that is consistent with the predicted size of the HRS-SV9 splice variant polypeptide. FIGS. 5B-C show the results for total cell lysate of IMR32 and HEK293T cells that over-express a myc-tagged HRS-SV11; the cells were immunoblotted with either the N-terminal HRS mAb (FIG. 5B), or a polyclonal HRS antibody (raised against the C-terminus of wild type human HRS protein) (FIG. 5C). A protein band, which migrated slightly faster than myc-tagged HRS-SV11 protein, was detected in IMR32 cell lysate by both antibodies (lower arrows in B and C) and could be the HRS-SV11 protein.

FIG. 6A, upper panel, shows arrows pointing to overexpressed proteins in total cell lysates (TCL). FIG. 6B, lower panel, shows that in media fractions all three proteins were detected. HRS-Ref was probed with anti-Myc antibody, while HRS-SV9 and HRS-SV11 were probed with anti-HRS (N-terminus) antibody. A tubulin blot in TCL showed equal loading, while a tubulin blot in the media fraction demonstrated leaky control. FIG. 6C shows that EGFP was not secreted when over-expressed in HEK293T cells, as indicated by the absence of an EGFP band (~35 kDa) in the media fraction.

FIGS. 9A-D show that HRS-SV11 protected cultured cortical neuron and PC12 cells against neurotoxin 6-OHDA. FIG. 9A shows that pre-treating rat cortical neurons with HRS-SV11 significantly reduced cortical neuron death induced by 25 μM 6-OHDA as measurement of cell viability by MTT assay. HRS-SV11 also effectively protected PC12 cells from 6-OHDA (200 μM)-induced cell death, as shown by MTT assay (FIG. 9B) and LDH assay (FIG. 9C). As shown in FIG. 9D, HRS-SV11's protective effect was an acute effect, with short time pre-treatment achieved similar protective effect as 24 hrs pre-treatment. Data are means±S.D. from three separate experiments. Tert-butylhydroquinone (tBHQ) and Triton X-100 (in short Triton) (2%) served as positive controls for MTT and LDH assays, respectively (B, C). $*p<0.05$, $**p<0.01$.

FIG. 10A shows the results of incubation with β-amyloid (1-42) ($A\beta_{42}$□) aggregates for 24 hrs, which induced cortical neuron death in a dose-dependent manner. FIG. 10B shows that pre-treating cortical neurons for 24 hrs with HRS-SV11, from 1 nM to 1 μM, had no protective effect as measured by MTT assay. FIG. 10C shows monosodium glutamate (MSG) induced cortical neuron death in a dose-dependent manner as measurement of LDH release, and FIG. 10D shows that HRS-SV11 had no beneficial effect against monosodium glutamate-induced toxicity; memantine at 10 μM significantly prevented neuron death, serving as a positive control. FIG. 10E shows that MPP+ induced PC12 cell death in a dose-dependent manner as measured by MTT assay, and FIG. 10F shows that HRS-SV11 did not protect PC12 cells from MPP+ stress after 24 hrs pre-treatment. Data are means±S.D. from three separate experiments.

As shown in FIG. 11A, addition of HRS-SV11 did not suppress p-quinone's accumulation, while vitamin C, a known anti-oxidant, did suppress its accumulation. FIG. 11B shows that hydrogen peroxide ($H_2O_2$) induced cortical neuron death in a dose-dependent manner, and FIG. 11C shows that pre-treating with HRS-SV11 did not protect these neurons from death. As shown in FIG. 11D, pre-treating cortical neurons with HRS-SV11 reduced neuron death upon 6-OHDA challenge, but co-application of HRS-SV11 with 6-OHDA had no protective effect. Before 6-OHDA application, washing and refreshing media after HRS-SV11 pre-treatment did not affect HRS-SV11's protective effect (see FIG. 11E). Data are means±S.D. from three separate experiments. $*p<0.05$, $**p<0.01$.

FIGS. 12A-D show that HRS-SV11 prevented DNA fragmentation induced by 6-OHDA in PC12 cells. Apoptosis of PC12 cells was examined by Hoechst 33258 staining. FIG. 12A shows PC12 cells treated with buffer control alone; FIG. 12B shows treatment with 6-OHDA (200 μM) for 8 h; and FIG. 12C shows pre-treatment with HRS-SV11 (500 nM) for 24 h followed by 8 h challenge with 6-OHDA (200 μM). As shown in FIG. 12D, numbers of apoptotic cells were counted (distinguished by presence of fragmented nuclei), demonstrating that pre-treatment with 1 μM HRS-SV11 greatly reduced the number of apoptotic cells.

FIGS. 13A-C show that mutation of cysteine (Cys) residues in the C-terminus of HRS-SV11 abolished the protective function. FIG. 13A shows that HRS-SV11 (SEQ ID NO:29) contains three Cys residues (C117, C169 and C171). Among them, C117 and C171 (arrows, FIG. 13A) are highly conserved across species, as shown by the alignment of amino acids 112 to about 171 of a variety of HRS sequences (SEQ ID NOS:16-24 and 29). As shown in FIG. 13B, the C2S (mutation of C169 and C171 into serine residue) and delC (deletion of last three amino acids, including C169 and C171) mutants were mostly monomer, while the C117S mutant was mostly dimer. The wild type HRS-SV11 had a peak in between monomer and dimer, indicating there was a very dynamic switch between these two forms. As shown in FIG. 13C, mutations of C169 and C171 into serine residue (HRS-SV11_C2S) or deletion of last three amino acids, including C169 and C171 (HRS-SV11_delC) abolished HRS-SV11's neuroprotective function, suggesting critical role of these Cys. **$p<0.01$.

As shown in FIGS. 14A-B, HRS-SV11's neuroprotective effect in PC12 cells was suppressed by co-inhibition of JNK by SB202190 at 10 µM and p38 by SP600125 at 10 µM (FIG. 14A), and by inhibition of JAK2 by AG490 at 40 µM (FIG. 14B). FIG. 14B also shows that the neuroprotective effect of HRS-SV11 was not suppressed by the inhibition of phospholipase C (PLC) by U73122, or MKK by arctigenin. FIGS. 14C-D show that similar observations were made with cortical neurons. Data are means±S.D. from three separate experiments. *$p<0.05$, **$p<0.01$.

As shown in FIG. 15C, binding to CCR-5 expressing cells was not affected by pre-treating cells with Met-RANTES. FIG. 15D shows that binding was specific to CCR5, since no binding was observed on CCR1-expressing cells. Control cells were incubated with FITC-His antibody only.

FIG. 16A shows that the identification of a new splicing variant of human HRS in human fetus brain cDNA (arrow). As shown in FIGS. 16A-B, cloning and sequencing revealed that this HRS splicing variant results from skipping of Exon 4 to Exon 10 in the wild-type HRS transcript (SEQ ID NOS:24-28 are in order from the upper to the lower part of FIG. 16B). On the protein level, HRS-SV14 protein was predicted to contain the WHEP domain, anticodon binding domain, and the first motif of the aminoacylation domain (see FIG. 16C). FIG. 16D shows that HRS-SV14, when pre-treated for 24 hr, protected PC12 cells from 6-OHDA-induced neuron death; and the effect was comparable to HRS-SV11. Data are means±S.D. from three separate experiments. *$p<0.05$.

FIG. 18A shows coomassie blue staining of recombinant HRS-SV11 protein preparation with or without proteinase K digestion; no visible protein band was detected in proteinase K-treated HRS-SV11 preparation, as compared to untreated HRS-SV11 preparation (arrowhead indicates HRS-SV11 recombinant protein). As shown in FIGS. 18B-C, pre-treating cortical neurons (FIG. 18B) and PC12 cells (FIG. 18C) with proteinase K-digested HRS-SV11 abolished its protective effect against 6-OHDA. tBHQ served as a positive control. NS stands for no significance. Data are means±S.D. from three separate experiments. *$p<0.05$, **$p<0.01$.

DETAILED DESCRIPTION OF THE INVENTION

Figure 1A:
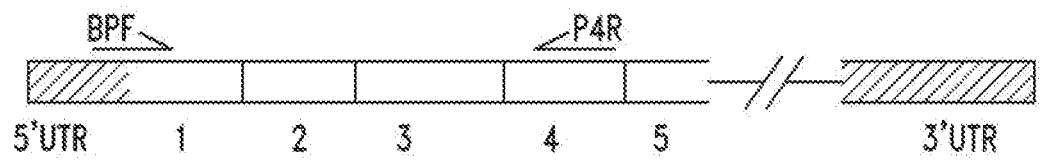
FIGS. 1A-B show the identification of the HRS-SV9 splice variant from a human skeletal muscle library.

The practice of the present invention will employ, unless indicated specifically to the contrary, conventional methods of molecular biology and recombinant DNA techniques within the skill of the art, many of which are described below for the purpose of illustration. Such techniques are explained fully in the literature. See, e.g., Sambrook, et al., *Molecular Cloning: A Laboratory Manual* (2nd Edition, 1989); Maniatis et al., *Molecular Cloning: A Laboratory Manual* (1982); *DNA Cloning: A Practical Approach*, vol. I & II (D. Glover, ed.); *Oligonucleotide Synthesis* (N. Gait, ed., 1984); *Nucleic Acid Hybridization* (B. Hames & S. Higgins, eds., 1985); *Transcription and Translation* (B. Hames & S. Higgins, eds., 1984); *Animal Cell Culture* (R. Freshney, ed., 1986); *A Practical Guide to Molecular Cloning* (B. Perbal, ed., 1984).

All publications, patents and patent applications cited herein are hereby incorporated by reference in their entirety.

Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

As used in this specification and the appended claims, the singular forms "a," "an" and "the" include plural references unless the content clearly dictates otherwise. By way of example, "an element" means one element or more than one element.

By "about" is meant a quantity, level, value, number, frequency, percentage, dimension, size, amount, weight or length that varies by as much as 30, 25, 20, 25, 10, 9, 8, 7, 6, 5, 4, 3, 2 or 1% to a reference quantity, level, value, number, frequency, percentage, dimension, size, amount, weight or length.

An "agonist" refers to a molecule that intensifies or mimics the non-canonical biological activity of an HRS. Agonists may include proteins, nucleic acids, carbohydrates, small molecules, or any other compound or composition that modulates the activity of an HRS either by directly interacting with the HRS or its binding partner, or by acting on components of the biological pathway in which the HRS participates. Included are partial and full agonists.

The term "antagonist" refers to a molecule that inhibits or attenuates the non-canonical biological activity of an HRS.

Antagonists may include proteins such as antibodies, nucleic acids, carbohydrates, small molecules, or any other compound or composition that modulates the activity of an HRS or its binding partner, either by directly interacting with the HRS or its binding partner or by acting on components of the biological pathway in which the HRS participates. Included are partial and full antagonists.

By "coding sequence" is meant any nucleic acid sequence that contributes to the code for the polypeptide product of a gene. By contrast, the term "non-coding sequence" refers to any nucleic acid sequence that does not contribute to the code for the polypeptide product of a gene.

Throughout this specification, unless the context requires otherwise, the words "comprise," "comprises," and "comprising" will be understood to imply the inclusion of a stated step or element or group of steps or elements but not the exclusion of any other step or element or group of steps or elements.

By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

As used herein, the terms "function" and "functional" and the like refer to a biological, enzymatic, or therapeutic function.

By "gene" is meant a unit of inheritance that occupies a specific locus on a chromosome and consists of transcriptional and/or translational regulatory sequences and/or a coding region and/or non-translated sequences (i.e., introns, 5' and 3' untranslated sequences).

"Homology" refers to the percentage number of amino acids that are identical or constitute conservative substitutions. Homology may be determined using sequence comparison programs such as GAP (Deveraux et al., 1984, *Nucleic Acids Research* 12, 387-395), which is incorporated herein by reference. In this way sequences of a similar or substantially different length to those cited herein could be compared by insertion of gaps into the alignment, such gaps being determined, for example, by the comparison algorithm used by GAP.

The term "host cell" includes an individual cell or cell culture that can be or has been a recipient of any recombinant vector(s) or isolated polynucleotide of the invention. Host cells include progeny of a single host cell, and the progeny may not necessarily be completely identical (in morphology or in total DNA complement) to the original parent cell due to natural, accidental, or deliberate mutation and/or change. A host cell includes cells transfected or infected in vivo or in vitro with a recombinant vector or a polynucleotide of the invention. A host cell which comprises a recombinant vector of the invention is a recombinant host cell.

By "isolated" is meant material that is substantially or essentially free from components that normally accompany it in its native state. For example, an "isolated polynucleotide," as used herein, includes a polynucleotide that has been purified from the sequences that flank it in its naturally-occurring state, e.g., a DNA fragment which has been removed from the sequences that are normally adjacent to the fragment. Alternatively, an "isolated peptide" or an "isolated polypeptide" and the like, as used herein, includes the in vitro isolation and/or purification of a peptide or polypeptide molecule from its natural cellular environment, and from association with other components of the cell; i.e., it is not significantly associated with in vivo substances.

The term "mRNA" or sometimes refer by "mRNA transcripts" as used herein, include, but not limited to pre-mRNA transcript(s), transcript processing intermediates, mature mRNA(s) ready for translation and transcripts of the gene or genes, or nucleic acids derived from the mRNA transcript(s). Transcript processing may include splicing, editing and degradation. As used herein, a nucleic acid derived from an mRNA transcript refers to a nucleic acid for whose synthesis the mRNA transcript or a subsequence thereof has ultimately served as a template. A cDNA reverse transcribed from an mRNA, an RNA transcribed from that cDNA, a DNA amplified from the cDNA, an RNA transcribed from the amplified DNA, etc., are all derived from the mRNA transcript and detection of such derived products is indicative of the presence and/or abundance of the original transcript in a sample. Thus, mRNA derived samples include, but are not limited to, mRNA transcripts of the gene or genes, cDNA reverse transcribed from the mRNA, cRNA transcribed from the cDNA, DNA amplified from the genes, RNA transcribed from amplified DNA, and the like.

"Non-canonical" activity as used herein, refers generally to an activity possessed by an HRS polypeptide of the invention that is other than aminoacylation and, more specifically, other than the addition of its cognate amino acid onto its cognate tRNA molecule. Non-limiting examples of non-canonical activities include RNA-binding, amino acid-binding, modulation of cell proliferation, modulation of cell migration, modulation of cell differentiation (e.g., hematopoiesis), modulation of apoptosis or other forms of cell death, modulation of cell signaling, modulation of angiogenesis, modulation of cell binding, modulation of cellular metabolism, modulation of cytokine production or activity, modulation of cytokine receptor activity, modulation of inflammation, and the like.

The term "modulating" includes "increasing" or "stimulating," as well as "decreasing" or "reducing," typically in a statistically significant or a physiologically significant amount as compared to a control. An "increased" or "enhanced" amount is typically a "statistically significant" amount, and may include an increase that is 1.1, 1.2, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the amount produced by no composition (the absence of an agent or compound) or a control composition. A "decreased" or reduced amount is typically a "statistically significant" amount, and may include a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% decrease in the amount produced by no composition (the absence of an agent or compound) or a control composition, including all integers in between. Other examples of "statistically significant" amounts are described herein.

By "obtained from" is meant that a sample such as, for example, a polynucleotide extract or polypeptide extract is isolated from, or derived from, a particular source of the subject. For example, the extract can be obtained from a tissue or a biological fluid isolated directly from the subject. "Derived" or "obtained from" can also refer to the source of a polypeptide or polynucleotide sequence. For instance, an HRS sequence of the present invention may be "derived" from the sequence information of an HRS proteolytic fragment or HRS splice variant, or a portion thereof, whether naturally-occurring or artificially generated, and may thus comprise, consist essentially of, or consist of that sequence.

The recitations "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity.

A "splice junction" as used herein includes the region in a mature mRNA transcript or the encoded polypeptide where the 3' end of a first exon joins with the 5' end of a second exon. The size of the region may vary, and may include 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100 or more (including all integers in between) nucleotide or amino acid residues on either side of the exact residues where the 3' end of one exon joins with the 5' end of another exon. An "exon" refers to a nucleic acid sequence that is represented in the mature form of an RNA molecule after either portions of a precursor RNA (introns) have been removed by cis-splicing or two or more precursor RNA molecules have been ligated by trans-splicing. The mature RNA molecule can be a messenger RNA or a functional form of a non-coding RNA such as rRNA or tRNA. Depending on the context, an exon can refer to the sequence in the DNA or its RNA transcript. An "intron" refers to a non-coding nucleic acid region within a gene, which is not translated into a protein. Non-coding intronic sections are transcribed to precursor mRNA (pre-mRNA) and some other RNAs (such as long noncoding RNAs), and subsequently removed by splicing during the processing to mature RNA.

A "splice variant" refers to a mature mRNA and its encoded protein that are produced by alternative splicing, a process by which the exons of the RNA (a primary gene transcript or pre-mRNA) are reconnected in multiple ways during RNA splicing. The resulting different mRNAs may be translated into different protein isoforms, allowing a single gene to code for multiple proteins.

A "subject," as used herein, includes any animal that exhibits a symptom, or is at risk for exhibiting a symptom, which can be treated or diagnosed with an HRS polynucleotide or polypeptide of the invention. Suitable subjects (patients) include laboratory animals (such as mouse, rat, rabbit, or guinea pig), farm animals, and domestic animals or pets (such as a cat or dog). Non-human primates and, preferably, human patients, are included.

"Treatment" or "treating," as used herein, includes any desirable effect on the symptoms or pathology of a disease or condition that can be effected by the non-canonical activities of an HRS polynucleotide or polypeptide, as described herein, and may include even minimal changes or improvements in one or more measurable markers of the disease or condition being treated. Also included are treatments that relate to non-HRS therapies, in which an HRS sequence described herein provides a clinical marker of treatment. "Treatment" or "treating" does not necessarily indicate complete eradication or cure of the disease or condition, or associated symptoms thereof. The subject receiving this treatment is any subject in need thereof. Exemplary markers of clinical improvement will be apparent to persons skilled in the art.

By "vector" or "nucleic acid construct" is meant a polynucleotide molecule, preferably a DNA molecule derived, for example, from a plasmid, bacteriophage, yeast or virus, into which a polynucleotide can be inserted or cloned. A vector preferably contains one or more unique restriction sites and can be capable of autonomous replication in a defined host cell including a target cell or tissue or a progenitor cell or tissue thereof, or be integrable with the genome of the defined host such that the cloned sequence is reproducible. Accordingly, the vector can be an autonomously replicating vector, i.e., a vector that exists as an extra-chromosomal entity, the replication of which is independent of chromosomal replication, e.g., a linear or closed circular plasmid, an extra-chromosomal element, a mini-chromosome, or an artificial chromosome. The vector can contain any means for assuring self-replication. Alternatively, the vector can be one which, when introduced into the host cell, is integrated into the genome and replicated together with the chromosome(s) into which it has been integrated.

The terms "wild-type" and "naturally occurring" are used interchangeably to refer to a gene or gene product that has the characteristics of that gene or gene product when isolated from a naturally occurring source. A wild-type gene or gene product (e.g., a polypeptide) is that which is most frequently observed in a population and is thus arbitrarily designed the "normal" or "wild-type" form of the gene.

HRS Splice Variant Polypeptides

As noted above, according to one aspect of the invention, there are provided HRS "splice variant" polypeptides having non-canonical activities of therapeutic relevance, as well as compositions comprising the same.

The terms "polypeptide," "peptide," and "protein" are used interchangeably herein to refer to a polymer of amino acid residues and to variants and synthetic analogues of the same. Thus, these terms apply to amino acid polymers in which one or more amino acid residues are synthetic non-naturally occurring amino acids, such as a chemical analogue of a corresponding naturally occurring amino acid, as well as to naturally-occurring amino acid polymers.

Polypeptides are not limited to a specific length, but, in the context of the present invention, typically represent a fragment of a full length protein, and may include post-translational modifications, for example, glycosylations, acetylations, phosphorylations and the like, as well as other modifications known in the art, both naturally occurring and non-naturally occurring. Polypeptides and proteins of the invention may be prepared using any of a variety of well known recombinant and/or synthetic techniques, illustrative examples of which are further discussed below.

The recitation "polypeptide variant" refers to polypeptides that are distinguished from a reference HRS splice variant polypeptide (e.g., SEQ ID NOS:6, 9, 11) by the addition, deletion, and/or substitution of at least one amino acid residue, and which typically retain the non-canonical activity of the reference HRS splice variant polypeptide. In certain embodiments, a polypeptide variant is distinguished from a reference polypeptide by one or more substitutions, which may be conservative or non-conservative, as described herein and known in the art. In certain embodiments, the polypeptide variant comprises conservative substitutions and, in this regard, it is well understood in the art that some amino acids may be changed to others with broadly similar properties without changing the nature of the activity of the polypeptide.

In certain embodiments, a polypeptide variant includes an amino acid sequence having at least about 50%, 55%, 60%, 65%, 70%, 75%, 80%, 85%, 90%, 91%, 92%, 93%, 94% 95%, 96%, 97%, 98% or more sequence identity or similarity to a corresponding sequence of an HRS reference polypeptide, as described herein, and retains the non-canonical activity of that reference polypeptide. Also included are sequences differing from the reference HRS sequences by the addition, deletion, or substitution of 1, 2, 3, 4, 5, 6, 7, 8, 9, 10, 11, 12, 13, 14, 15, 16, 17, 18, 19, 20, 30, 40, 50, 60, 70, 80, 90, 100, 110, 120, 130, 140, 150 or more amino acids but which retain the properties of the reference HRS polypeptide. In other embodiments, variant polypeptides differ from the corresponding HRS reference sequences by at least 1% but less than 20%, 15%, 10% or 5% of the residues. (If this comparison requires alignment, the sequences should be aligned for maximum similarity. "Looped" out sequences from deletions or insertions, or mismatches, are considered differences.) The differences are, suitably, differences or changes at a non-essential residue or a conservative substitution.

Also included are biologically active "fragments" of the HRS reference polypeptides. Representative biologically active fragments generally participate in an interaction, e.g., an intramolecular or an inter-molecular interaction. An inter-molecular interaction can be a specific binding interaction or an enzymatic interaction. An inter-molecular interaction can be between an HRS polypeptide and a cellular binding partner, such as a cellular receptor or other host molecule that participates in the non-canonical activity of the HRS polypeptide.

Typically, biologically active fragments comprise a domain or motif with at least one activity of an HRS reference polypeptide and may include one or more (and in some cases all) of the various active domains, and include fragments having a non-canonical activity. In some cases, biologically active fragments of an HRS polypeptide have a biological activity that is unique to the particular, truncated fragment, such that the full-length HRS polypeptide may not have that activity. In certain cases, the biological activity may be revealed by separating the biologically active HRS polypeptide fragment from the other full-length HRS polypeptide sequences, or by altering certain residues of the full-length HRS wild-type polypeptide sequence to unmask the biologically active domains.

For example, in one illustrative embodiment, the HRS splice variant polypeptide is a HRS fragment comprising at least the WHEP domain of HRS, or an active fragment or variant thereof. In another illustrative embodiment, the polypeptide is a HRS fragment comprising at least the anticodon binding domain of HRS, or an active fragment or variant thereof. In yet another illustrative embodiment, the polypeptide is a HRS fragment comprising at least the WHEP domain and the anticodon binding domain of HRS. In still another illustrative embodiment, the polypeptide is a HRS fragment lacking the aminoacylation domain and substantially devoid of aminoacylation activity.

In a more particular embodiment, the HRS splice variant polypeptide is a polypeptide comprising a sequence set forth in SEQ ID NOs:6, 9 or 11. In another embodiment, the HRS splice variant polypeptide is a polypeptide comprising an active fragment of SEQ ID NOs: 6, 9 or 11 (i.e., a fragment of SEQ ID NOs: 6, 9 or 11 that substantially retains at least one non-canonical activity exhibited by SEQ ID NOs: 6, 9 or 11). For example, such a fragment may comprise at least about 5, 10, 15, 20, 25, or 50, or more, contiguous amino acid residues of SEQ ID NOs: 6, 9 or 11, as well as all intermediate lengths. Intermediate lengths are intended to include all integers therebetween, for example, 6, 7, 8, etc., 51, 52, 53, etc. In addition, such a fragment may comprise at least about 5, 10, 15, 20, 25, 50, 75, 100, 125, or 150, or more, contiguous amino acid residues of SEQ ID NO: 9, as well as all intermediate lengths.

A biologically active fragment of an HRS reference polypeptide can be a polypeptide fragment which is, for example, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 110, 120, 130, 140, 150, 160, 170 or more contiguous or non-contiguous amino acids, including all integers in between, of the amino acid sequences set forth SEQ ID NOS:6, 9, or 11. In certain embodiments, the C-terminal or N-terminal region of any HRS reference polypeptide may be truncated by about 1, 2, 3, 4, 5, 6, 7, 8, 9, 10, 15, 20, 25, 30, 35, 40, 45, 50, 60, 70, 80, 90, 100, 110, 120, 130, 140, 150, 160, 170, 180 or more amino acids, including all integers and ranges in between (e.g., 101, 102, 103, 104, 105), so long as the truncated HRS polypeptide retains the non-canonical activity of the reference HRS splice variant polypeptide. Suitably, the biologically-active fragment has no less than about 1%, 10%, 25%, or 50% of an activity of the biologically-active (i.e., non-canonical activity) HRS reference polypeptide from which it is derived.

In other illustrative embodiments, a HRS fragment of SEQ ID NO: 6, 9 or 11 may range in size from about 20-30, 20-40, 20-50, 20-60, 20-70, 20-80, 20-90, 20-100, 20-125, 20-150 or 20-175 amino acids in length. In other embodiments, the fragment will range in size from about 30-40, 30-50, 30-60, 30-70, 30-80, 30-90, 30-100, 30-125, 30-150 or 30-175 amino acids in length. In other embodiments, the fragment will range in size from about 40-50, 40-60, 40-70, 40-80, 40-90, 40-100, 40-125, 40-150 or 40-175 amino acids in length. In still other illustrative embodiments, the fragment will range in size from about 50-60, 50-70, 50-80, 50-90, 50-100, 50-125, 50-150 or 50-175 amino acids in length.

In still other embodiments, the present invention provides active variants of a HRS splice variant polypeptide (e.g., SEQ ID NOs: 6, 9 or 11), wherein said variants substantially retain at least one non-canonical activity exhibited by SEQ ID NOs: 6, 9 or 11. Certain illustrative variants of the sequence set forth in SEQ ID NOs: 6, 9 or 11 include those having at least about 70%, 75%, 80%, 85%, 90%, 91%, 92%, 93%, 94%, 95%, 96%, 97%, 98%, or 99% identity (determined as described below), along their lengths, to SEQ ID NOs: 6, 9 or 11.

A variant may differ from SEQ ID NOs: 6, 9 or 11 in one or more substitutions, deletions, additions and/or insertions. Such variants may be naturally occurring or may be synthetically generated, for example, by modifying SEQ ID NOs: 6, 9 or 11 (or a polynucleotide encoding SEQ ID NOs: 6, 9 or 11) and evaluating their biological activity as described herein using any of a number of techniques well known in the art.

In certain embodiments, a variant will contain conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Modifications may be made in the structure of the polynucleotides and polypeptides of the present invention and still obtain a functional molecule that encodes a variant or derivative polypeptide with desirable characteristics. When it is desired to alter the amino acid sequence of a polypeptide to create an equivalent, or even an improved, variant of a HRS splice variant polypeptide of the invention, one skilled in the art, for example, can change one or more of the codons of the encoding DNA sequence according to Table 1.

Certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that generally defines that protein's biological functional activity, certain amino acid sequence substitutions can be made in a protein sequence, and, of course, its underlying DNA coding sequence, and nevertheless obtain a protein with like properties. It is thus contemplated that various changes may be made in the polypeptide sequences of the disclosed compositions, or corresponding DNA sequences which encode said polypeptides without appreciable loss of their desired utility or activity.

TABLE 1

| Amino Acids | | | Codons | | | | |
|---|---|---|---|---|---|---|---|
| Alanine | Ala | A | GCA | GCC | GCG | GCU | |
| Cysteine | Cys | C | UGC | UGU | | | |
| Aspartic acid | Asp | D | GAC | GAU | | | |
| Glutamic acid | Glu | E | GAA | GAG | | | |
| Phenylalanine | Phe | F | UUC | UUU | | | |
| Glycine | Gly | G | GGA | GGC | GGG | GGU | |
| Histidine | His | H | CAC | CAU | | | |
| Isoleucine | Ile | I | AUA | AUC | AUU | | |
| Lysine | Lys | K | AAA | AAG | | | |
| Leucine | Leu | L | UUA | UUG | CUA | CUC | CUG | CUU |
| Methionine | Met | M | AUG | | | | |
| Asparagine | Asn | N | AAC | AAU | | | |
| Proline | Pro | P | CCA | CCC | CCG | CCU | |
| Glutamine | Gln | Q | CAA | CAG | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | |
| Valine | Val | V | GUA | GUC | GUG | GUU | |
| Tryptophan | Trp | W | UGG | | | | |
| Tyrosine | Tyr | Y | UAC | UAU | | | |

In making such changes, the hydropathic index of amino acids may also be considered. The importance of the hydropathic amino acid index in conferring interactive biologic function on a protein is generally understood in the art (Kyte and Doolittle, 1982, incorporated herein by reference). For example, it is known that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of its hydrophobicity and charge characteristics (Kyte and Doolittle, 1982). These values are: isoleucine (+4.5); valine (+4.2); leucine (+3.8); phenylalanine (+2.8); cysteine/cysteine (+2.5); methionine (+1.9); alanine (+1.8); glycine (0.4); threonine (0.7); serine (0.8); tryptophan (0.9); tyrosine (1.3); proline (1.6); histidine (3.2); glutamate (3.5); glutamine (3.5); aspartate (3.5); asparagine (3.5); lysine (3.9); and arginine (4.5).

It is known in the art that certain amino acids may be substituted by other amino acids having a similar hydropathic index or score and still result in a protein with similar biological activity, i.e. still obtain a biological functionally equivalent protein. In making such changes, the substitution of amino acids whose hydropathic indices are within ±2 is preferred, those within ±1 are particularly preferred, and those within ±0.5 are even more particularly preferred.

It is also understood in the art that the substitution of like amino acids can be made effectively on the basis of hydrophilicity. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions may be based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

Amino acid substitutions may further be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain non-conservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on secondary structure and hydropathic nature of the polypeptide.

Polypeptides may comprise a signal (or leader) sequence at the N-terminal end of the protein, which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

When comparing polypeptide sequences, two sequences are said to be "identical" if the sequence of amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted, for example, using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J. (1990) Unified Approach to Alignment and Phylogenes pp. 626-645 *Methods in Enzymology* vol. 183, Academic Press, Inc., San Diego, Calif.; Higgins, D. G. and Sharp, P. M. (1989) *CABIOS* 5:151-153; Myers, E. W. and Muller W. (1988) *CABIOS* 4:11-17; Robinson, E. D. (1971) *Comb. Theor* 11:105; Santou, N. Nes, M. (1987) *Mol. Biol. Evol.* 4:406-425; Sneath, P. H. A. and Sokal, R. R. (1973) *Numerical Taxonomy—the Principles and Practice of Numerical Taxonomy*, Freeman Press, San Francisco, Calif.; Wilbur, W. J. and Lipman, D. J. (1983) *Proc. Nat'l Acad., Sci. USA* 80:726-730.

Alternatively, optimal alignment of sequences for comparison may be conducted by the local identity algorithm of Smith and Waterman (1981) *Add. APL. Math* 2:482, by the identity alignment algorithm of Needleman and Wunsch (1970) *J. Mol. Biol.* 48:443, by the search for similarity methods of Pearson and Lipman (1988) *Proc. Nat'l Acad. Sci. USA* 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

Examples of algorithms that are suitable for determining percent sequence identity and sequence similarity are the BLAST and BLAST 2.0 algorithms, which are described in Altschul et al. (1977) *Nucl. Acids Res.* 25:3389-3402 and Altschul et al. (1990) *J. Mol. Biol.* 215:403-410, respectively. BLAST and BLAST 2.0 can be used, for example with the parameters described herein, to determine percent sequence identity for the polynucleotides and polypeptides of the invention. Software for performing BLAST analyses is publicly available through the National Center for Biotechnology Information. For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment.

In one illustrative approach, the "percentage of sequence identity" is determined by comparing two optimally aligned sequences over a window of comparison of at least 20 positions, wherein the portion of the polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical amino acid residue occurs in both sequences to yield the number of matched positions, dividing the number of matched positions by the total number of positions in the reference sequence (i.e., the window size) and multiplying the results by 100 to yield the percentage of sequence identity.

In certain embodiments of the invention, there are provided fusion polypeptides, and polynucleotides encoding fusion polypeptides. Fusion polypeptides refer to HRS splice variant polypeptides of the invention that have been covalently linked, either directly or indirectly via an amino acid linker, to one or more heterologous polypeptide sequences (fusion partners). The polypeptides forming the fusion protein are typically linked C-terminus to N-terminus, although they can also be linked C-terminus to C-terminus, N-terminus to N-terminus, or N-terminus to C-terminus. The polypeptides of the fusion protein can be in any order.

The fusion partner may be designed and included for essentially any desired purpose provided they do not adversely affect the desired activity of the polypeptide. For example, in one embodiment, a fusion partner comprises a sequence that assists in expressing the protein (an expression enhancer) at higher yields than the native recombinant protein. Other fusion partners may be selected so as to increase the solubility of the protein or to enable the protein to be targeted to desired intracellular compartments or to be secreted outside the cell. Still further fusion partners may include affinity tags, which facilitate purification of the protein.

More generally, fusion to heterologous sequences, such as an Fc fragment, may be utilized to remove unwanted characteristics or to improve the desired characteristics (e.g., pharmacokinetic properties) of an HRS polypeptide. For example, fusion to a heterologous sequence may increase chemical stability, decrease immunogenicity, improve in vivo targeting, and/or increase half-life in circulation of an HRS polypeptide.

Fusion to heterologous sequences may also be used to create bi-functional fusion proteins, such as bi-functional proteins that are not only possess a selected non-canonical activity through the HRS polypeptide, but are also capable of modifying (i.e., stimulating or inhibiting) other pathways through the heterologous polypeptide. Examples of such pathways include, but are not limited to, various immune system-related pathways, such as innate or adaptive immune activation pathways, or cell-growth regulatory pathways, such as angiogenesis. In certain aspects, the heterologous polypeptide may act synergistically with the HRS polypeptide to modulate a cellular pathway in a subject. Examples of heterologous polypeptides that may be utilized to create a bi-functional fusion protein include, but are not limited to, thrombopoietin, cytokines (e.g., IL-11), chemokines, and various hematopoietic growth factors, in addition to biologically active fragments and/or variants thereof.

Fusion polypeptides may generally be prepared using standard techniques. For example, DNA sequences encoding the polypeptide components of a desired fusion may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion polypeptide that retains the biological activity of both component polypeptides.

A peptide linker sequence may be employed to separate the first and second polypeptide components by a distance sufficient to ensure that each polypeptide folds into its secondary and tertiary structures, if desired. Such a peptide linker sequence is incorporated into the fusion protein using standard techniques well known in the art. Certain peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39 46 (1985); Murphy et al., *Proc. Natl. Acad. Sci. USA* 83:8258 8262 (1986); U.S. Pat. Nos. 4,935,233 and 4,751,180. The linker sequence may generally be from 1 to about 50 amino acids in length. Linker sequences are not required when the first and second polypeptides have nonessential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding the second polypeptide.

In general, polypeptides and fusion polypeptides (as well as their encoding polynucleotides) are isolated. An "isolated" polypeptide or polynucleotide is one that is removed from its original environment. For example, a naturally-occurring protein is isolated if it is separated from some or all of the coexisting materials in the natural system. Preferably, such polypeptides are at least about 90% pure, more preferably at least about 95% pure and most preferably at least about 99% pure. A polynucleotide is considered to be isolated if, for example, it is cloned into a vector that is not a part of the natural environment.

In still other embodiments, a HRS splice variant polypeptide of the invention may be part of a dimer. Dimers may include, for example, homodimers between two identical HRS polypeptides, heterodimers between two different HRS polypeptides and/or heterodimers between a HRS polypeptide and a heterologous polypeptide. The monomers and/or dimers may be soluble and may be isolated or purified to homogeneity. Certain heterodimers, such as those between a HRS polypeptide and a heterologous polypeptide, may be bi-functional.

Also included are monomers of HRS polypeptides, including isolated HRS monomers that do not substantially dimerize with themselves (homodomerize) or with a second HRS polypeptide (heterodimerize), whether due to one or more substitutions, truncations, deletions, additions, chemical modifications, or a combination of these alterations. In certain embodiments, monomeric HRS polypeptides possess biological activities, including non-canonical activities, which are not possessed by dimeric or multimeric HRS polypeptide complexes.

In other embodiments, a HRS polypeptide of the invention may be part of a multi-unit complex. A multi-unit complex of the present invention can include, for example, at least 2, 3, 4, or 5 or more monomers. The monomers and/or multi-unit complexes of the present invention may be soluble and may be isolated or purified to homogeneity. Monomer units of a multi-unit complex may be different, homologous, substantially homologous, or identical to one another. However, a multi-unit complex of the invention includes at least one monomer comprising a HRS polypeptide as described herein or, in other embodiments, at least two or more HRS polypeptides as described herein.

Covalently linked monomers can be linked directly (by bonds) or indirectly (e.g., via a linker). For directly linking the polypeptide herein, it may be beneficial to modify the polypeptides to enhance dimerization. For example, one or more amino acid residues of a HRS polypeptide may be modified by the addition or substation by one or more cysteines. Methods for creating amino acid substitutions, such as cysteine substitutions, or other modifications to facilitate linking, are well known to those skilled in the art.

Certain embodiments of the present invention also contemplate the use of modified HRS polypeptides, including modifications that improve desired characteristics of a HRS polypeptide, as described herein. Illustrative modifications of HRS polypeptides of the invention include, but are not limited to, chemical and/or enzymatic derivatizations at one or more constituent amino acids, including side chain modifications, backbone modifications, and N- and/or C-terminal modifications including acetylation, hydroxylation, methylation, amidation, and the attachment of carbohydrate or lipid moieties, cofactors, and the like. Exemplary modifications also include pegylation of a HRS polypeptide (see, e.g., Veronese and Harris, *Advanced Drug Delivery Reviews* 54: 453-456, 2002, herein incorporated by reference).

In certain aspects, chemoselective ligation technology may be utilized to modify HRS polypeptides of the invention, such as by attaching polymers in a site-specific and controlled manner. Such technology typically relies on the incorporation of chemoselective anchors into the protein backbone by either chemical or recombinant means and subsequent modification with a polymer carrying a complementary linker. As a result, the assembly process and the covalent structure of the resulting protein-polymer conjugate may be controlled, enabling the rational optimization of drug properties, such as efficacy and pharmacokinetic properties (see, e.g., Kochendoerfer, *Current Opinion in Chemical Biology* 9:555-560, 2005).

The HRS polypeptides described herein may be prepared by any suitable procedure known to those of skill in the art, such as by recombinant techniques. For example, HRS polypeptides may be prepared by a procedure including the steps of: (a) preparing a construct comprising a polynucleotide sequence that encodes an HRS polypeptide and that is operably linked to a regulatory element; (b) introducing the construct into a host cell; (c) culturing the host cell to express the HRS polypeptide; and (d) isolating the HRS polypeptide from the host cell. Recombinant HRS polypeptides can be conveniently prepared using standard protocols as described for example in Sambrook, et al., (1989, supra), in particular Sections 16 and 17; Ausubel et al., (1994, supra), in particular Chapters 10 and 16; and Coligan et al., Current Protocols in Protein Science (John Wiley & Sons, Inc. 1995-1997), in particular Chapters 1, 5 and 6.

In addition to recombinant production methods, polypeptides of the invention, and fragments thereof, may be produced by direct peptide synthesis using solid-phase techniques (Merrifield, J. Am. Chem. Soc. 85:2149-2154 (1963)). Protein synthesis may be performed using manual techniques or by automation. Automated synthesis may be achieved, for example, using Applied Biosystems 431A Peptide Synthesizer (Perkin Elmer). Alternatively, various fragments may be chemically synthesized separately and combined using chemical methods to produce the desired molecule.

Polynucleotide Compositions

The present invention also provides isolated polynucleotides that encode a HRS splice variant polypeptide of the invention, as described herein, as well as compositions comprising such polynucleotides. In certain embodiments, typically due to the singular nature of an HRS splice variant, which combines exons in a new or exceptional way, the HRS polynucleotides comprise a unique or exceptional splice junction. Exemplary reference HRS splice variant polynucleotides include SEQ ID NOS:5, 8, and 10, and variants and complements thereof.

Also included within the HRS polynucleotides of the present invention are primers, probes, antisense oligonucleotides, and RNA interference agents that comprise all or a portion of these reference polynucleotides, which are complementary to all or a portion of these reference polynucleotides, or which specifically hybridize to these reference polynucleotides, as described herein.

As used herein, the terms "DNA" and "polynucleotide" and "nucleic acid" refer to a DNA molecule that has been isolated free of total genomic DNA of a particular species. Therefore, a DNA segment encoding a polypeptide refers to a DNA segment that contains one or more coding sequences yet is substantially isolated away from, or purified free from, total genomic DNA of the species from which the DNA segment is obtained. Included within the terms "DNA segment" and "polynucleotide" are DNA segments and smaller fragments of such segments, and also recombinant vectors, including, for example, plasmids, cosmids, phagemids, phage, viruses, and the like.

As will be understood by those skilled in the art, the polynucleotide sequences of this invention can include genomic sequences, extra-genomic and plasmid-encoded sequences and smaller engineered gene segments that express, or may be adapted to express, proteins, polypeptides, peptides and the like. Such segments may be naturally isolated, or modified synthetically by the hand of man.

As will be recognized by the skilled artisan, polynucleotides may be single-stranded (coding or antisense) or double-stranded, and may be DNA (genomic, cDNA or synthetic) or RNA molecules. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes a HRS polypeptide of the invention or a portion thereof) or may comprise a variant, or a biological functional equivalent of such a sequence. Polynucleotide variants may contain one or more substitutions, additions, deletions and/or insertions, as further described below, preferably such that the desired non-canonical activity of the encoded polypeptide is not substantially diminished relative to the unmodified polypeptide. The effect on the activity of the encoded polypeptide may generally be assessed as described herein and as would be recognized in the art.

The present invention further provides isolated polynucleotide fragments comprising various lengths of contiguous stretches of sequence identical to or complementary to a HRS splice variant polynucleotide (e.g., SEQ ID NOs: 5, 8, or 10), as described herein, wherein the isolated polynucleotide encodes a HRS splice variant polypeptide of the invention, or an active fragment or variant thereof.

For example, polynucleotides are provided by this invention that encode at least about 5, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 41, 43, 44, 45, 46, 47, 48, 49, 50, 60, 70, 80, 90, 100, 110, 120, 130, 140, 150, 160, 170 or more, contiguous amino acid residues of a HRS polypeptide of the invention, as well as all intermediate lengths. It will be readily understood that "intermediate lengths", in this context, means any length between the quoted values, such as 21, 22, 23, etc.; 31, 32, 33, etc.; 41, 42, 43, etc.

The polynucleotides of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a polynucleotide fragment of almost any length may be employed; with the total length preferably being limited by the ease of preparation and use in the intended recombinant DNA protocol.

As noted above, certain embodiments relate to HRS polynucleotides that encode an HRS polypeptide. Among other uses, these embodiments may be utilized to recombinantly produce a desired HRS polypeptide or variant thereof, or to express the HRS polypeptide in a selected cell or subject. It will be appreciated by those of ordinary skill in the art that, as a result of the degeneracy of the genetic code, there are many nucleotide sequences that can encode a given HRS polypeptide as described herein. Some of these polynucleotides may bear only limited homology to the reference nucleotide sequence. Nevertheless, such polynucleotides (i.e., degenerate variant polynucleotides) would be understood to encode the very same polypeptide. Accordingly, polynucleotides that vary due to differences in codon usage are specifically contemplated by the present invention, for example polynucleotides that are optimized for human and/or primate codon selection.

Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

Polynucleotides and fusions thereof may be prepared, manipulated and/or expressed using any of a variety of well established techniques known and available in the art. For example, polynucleotide sequences which encode polypeptides of the invention, or fusion proteins or functional equivalents thereof, may be used in recombinant DNA molecules to direct expression of a HRS polypeptide of the invention in appropriate host cells. Due to the inherent degeneracy of the genetic code, other DNA sequences that encode substantially the same or a functionally equivalent amino acid sequence may be produced and these sequences may be used to clone and express a given polypeptide.

As will be understood by those of skill in the art, it may be advantageous in some instances to produce polypeptide-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

Moreover, the polynucleotide sequences of the present invention can be engineered using methods generally known in the art in order to alter polypeptide encoding sequences for a variety of reasons, including but not limited to, alterations which modify the cloning, processing, expression and/or activity of the gene product.

In order to express a desired polypeptide, a nucleotide sequence encoding the polypeptide, or a functional equivalent, may be inserted into appropriate expression vector, i.e., a vector which contains the necessary elements for the transcription and translation of the inserted coding sequence. Methods which are well known to those skilled in the art may be used to construct expression vectors containing sequences encoding a polypeptide of interest and appropriate transcriptional and translational control elements. These methods include in vitro recombinant DNA techniques, synthetic techniques, and in vivo genetic recombination. Such techniques are described in Sambrook et al., Molecular Cloning, A Laboratory Manual (1989), and Ausubel et al., Current Protocols in Molecular Biology (1989).

A variety of expression vector/host systems are known and may be utilized to contain and express polynucleotide sequences. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems, including viral-based expression systems.

The "control elements" or "regulatory sequences" present in an expression vector are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the PBLUESCRIPT phagemid (Stratagene, La Jolla, Calif.) or PSPORT1 plasmid (Gibco BRL, Gaithersburg, Md.) and the like may be used. In mammalian cell systems, promoters from mammalian genes or from mammalian viruses are generally preferred. If it is necessary to generate a cell line that contains multiple copies of the sequence encoding a polypeptide, vectors based on SV40 or EBV may be advantageously used with an appropriate selectable marker.

Specific initiation signals may also be used to achieve more efficient translation of sequences encoding a polypeptide of interest. Such signals include the ATG initiation codon and adjacent sequences. The efficiency of expression may be enhanced by the inclusion of enhancers which are appropriate for the particular cell system which is used, such as those described in the literature (Scharf. et al., *Results Probl. Cell Differ.* 20:125-162 (1994)).

In addition, a host cell strain may be chosen for its ability to modulate the expression of the inserted sequences or to process the expressed protein in the desired fashion. Such post-translational modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells such as CHO, HeLa, MDCK, HEK293, and W138, which have specific cellular machinery and characteristic mechanisms for such post-translational activities, may be chosen to ensure the correct modification and processing of the foreign protein.

For long-term, high-yield production of recombinant proteins, stable expression is generally preferred. For example, cell lines which stably express a polynucleotide of interest may be transformed using expression vectors which may contain viral origins of replication and/or endogenous expression elements and a selectable marker gene on the same or on a separate vector. Following the introduction of the vector, cells may be allowed to grow for 1-2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler et al., *Cell* 11:223-232 (1977)) and adenine phosphoribosyltransferase (Lowy et al., *Cell* 22:817-823 (1990)) genes which can be employed in tk- or aprt-cells, respectively. Also, antimetabolite, antibiotic or herbicide resistance can be used as the basis for selection; for example, dhfr which confers resistance to methotrexate (Wigler et al., *Proc. Natl. Acad. Sci. U.S.A.* 77:3567-70 (1980)); npt, which confers resistance to the aminoglycosides, neomycin and G-418 (Colbere-Garapin et al., *J. Mol. Biol.* 150:1-14 (1981)); and als or pat, which confer resistance to chlorsulfuron and phosphinotricin acetyltransferase, respectively (Murry, supra).

A variety of protocols for detecting and measuring the expression of polynucleotide-encoded products, using either polyclonal or monoclonal antibodies specific for the product are known in the art. Examples include enzyme-linked immunosorbent assay (ELISA), radioimmunoassay (RIA), and fluorescence activated cell sorting (FACS). These and other assays are described, among other places, in Hampton et al., *Serological Methods, a Laboratory Manual* (1990) and Maddox et al., *J. Exp. Med.* 158:1211-1216 (1983).

Host cells transformed with a polynucleotide sequence of interest may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides of the invention may be designed to contain signal sequences which direct secretion of the encoded polypeptide through a prokaryotic or eukaryotic cell membrane. Other recombinant constructions may be used to join sequences encoding a polypeptide of interest to nucleotide sequence encoding a polypeptide domain which will facilitate purification of soluble proteins.

In addition to recombinant production methods, polypeptides of the invention, and fragments thereof, may be produced by direct peptide synthesis using solid-phase techniques (Merrifield, *J. Am. Chem. Soc.* 85:2149-2154 (1963)). Protein synthesis may be performed using manual techniques or by automation. Automated synthesis may be achieved, for example, using Applied Biosystems 431A Peptide Synthesizer (Perkin Elmer). Alternatively, various fragments may be chemically synthesized separately and combined using chemical methods to produce the full length molecule.

According to another aspect of the invention, polynucleotides encoding polypeptides of the invention may be delivered to a subject in vivo, e.g., using gene therapy techniques. Gene therapy refers generally to the transfer of heterologous nucleic acids to the certain cells, target cells, of a mammal, particularly a human, with a disorder or conditions for which such therapy is sought. The nucleic acid is introduced into the selected target cells in a manner such that the heterologous DNA is expressed and a therapeutic product encoded thereby is produced.

Various viral vectors that can be utilized for gene therapy as taught herein include adenovirus, herpes virus, vaccinia, adeno-associated virus (AAV), or, preferably, an RNA virus such as a retrovirus. Preferably, the retroviral vector is a derivative of a murine or avian retrovirus, or is a lentiviral vector. The preferred retroviral vector is a lentiviral vector. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), SIV, BIV, HIV and Rous Sarcoma Virus (RSV). A number of additional retroviral vectors can incorporate multiple genes. All of these vectors can transfer or incorporate a gene for a selectable marker so that transduced cells can be identified and generated. By inserting a zinc finger derived-DNA binding polypeptide sequence of interest into the viral vector, along with another gene that encodes the ligand for a receptor on a specific target cell, for example, the vector may be made target specific. Retroviral vectors can be made target specific by inserting, for example, a polynucleotide encoding a protein (dimer). Illustrative targeting may be accomplished by using an antibody to target the retroviral vector. Those of skill in the art will know of, or can readily ascertain without undue experimentation, specific polynucleotide sequences which can be inserted into the retroviral genome to allow target specific delivery of the retroviral vector containing the zinc finger-nucleotide binding protein polynucleotide.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsulation. Helper cell lines which have deletions of the packaging signal include but are not limited to PSI.2, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced. The vector virions produced by this method can then be used to infect a tissue cell line, such as NIH 3T3 cells, to produce large quantities of chimeric retroviral virions.

"Non-viral" delivery techniques for gene therapy can also be used including, for example, DNA-ligand complexes, adenovirus-ligand-DNA complexes, direct injection of DNA, $CaPO_4$ precipitation, gene gun techniques, electroporation, liposomes, lipofection, and the like. Any of these methods are widely available to one skilled in the art and would be suitable for use in the present invention. Other suitable methods are available to one skilled in the art, and it is to be understood that the present invention can be accomplished using any of the available methods of transfection. Lipofection can be accomplished by encapsulating an isolated DNA molecule within a liposomal particle and contacting the liposomal particle with the cell membrane of the target cell. Liposomes are self-assembling, colloidal particles in which a lipid bilayer, composed of amphiphilic molecules such as phosphatidyl serine or phosphatidyl choline, encapsulates a portion of the surrounding media such that the lipid bilayer surrounds a hydrophilic interior. Unilammellar or multilammellar liposomes can be constructed such that the interior contains a desired chemical, drug, or, as in the instant invention, an isolated DNA molecule.

Certain embodiments include polynucleotides that hybridize to a reference HRS polynucleotide sequence, or to their complements, under stringency conditions described below. As used herein, the term "hybridizes under low stringency, medium stringency, high stringency, or very high stringency conditions" describes conditions for hybridization and washing. Guidance for performing hybridization reactions can be found in Ausubel et al., (1998, supra), Sections 6.3.1-6.3.6. Aqueous and non-aqueous methods are described in that reference and either can be used.

Reference herein to low stringency conditions include and encompass from at least about 1% v/v to at least about 15% v/v formamide and from at least about 1 M to at least about 2 M salt for hybridization at 42° C., and at least about 1 M to at least about 2 M salt for washing at 42° C. Low stringency conditions also may include 1% Bovine Serum Albumin (BSA), 1 mM EDTA, 0.5 M $NaHPO_4$ (pH 7.2), 7% SDS for hybridization at 65° C., and (i) 2×SSC, 0.1% SDS; or (ii) 0.5% BSA, 1 mM EDTA, 40 mM $NaHPO_4$ (pH 7.2), 5% SDS for washing at room temperature. One embodiment of low stringency conditions includes hybridization in 6× sodium chloride/sodium citrate (SSC) at about 45° C., followed by two washes in 0.2×SSC, 0.1% SDS at least at 50° C. (the temperature of the washes can be increased to 55° C. for low stringency conditions).

Medium stringency conditions include and encompass from at least about 16% v/v to at least about 30% v/v formamide and from at least about 0.5 M to at least about 0.9 M salt for hybridization at 42° C., and at least about 0.1 M to at least about 0.2 M salt for washing at 55° C. Medium stringency conditions also may include 1% Bovine Serum Albumin (BSA), 1 mM EDTA, 0.5 M $NaHPO_4$ (pH 7.2), 7% SDS for hybridization at 65° C., and (i) 2×SSC, 0.1% SDS; or (ii) 0.5% BSA, 1 mM EDTA, 40 mM $NaHPO_4$ (pH 7.2), 5% SDS for washing at 60-65° C. One embodiment of medium stringency conditions includes hybridizing in 6×SSC at about 45° C., followed by one or more washes in 0.2×SSC, 0.1% SDS at 60° C. High stringency conditions include and encompass from at least about 31% v/v to at least about 50% v/v formamide and from about 0.01 M to about 0.15 M salt for hybridization at 42° C., and about 0.01 M to about 0.02 M salt for washing at 55° C.

High stringency conditions also may include 1% BSA, 1 mM EDTA, 0.5 M $NaHPO_4$ (pH 7.2), 7% SDS for hybridization at 65° C., and (i) 0.2×SSC, 0.1% SDS; or (ii) 0.5% BSA, 1 mM EDTA, 40 mM $NaHPO_4$ (pH 7.2), 1% SDS for washing at a temperature in excess of 65° C. One embodiment of high stringency conditions includes hybridizing in 6×SSC at about 45° C., followed by one or more washes in 0.2×SSC, 0.1% SDS at 65° C. One embodiment of very high stringency conditions includes hybridizing in 0.5 M sodium phosphate, 7% SDS at 65° C., followed by one or more washes in 0.2×SSC, 1% SDS at 65° C.

Other stringency conditions are well known in the art and a skilled artisan will recognize that various factors can be manipulated to optimize the specificity of the hybridization. Optimization of the stringency of the final washes can serve to ensure a high degree of hybridization. For detailed examples, see Ausubel et al., supra at pages 2.10.1 to 2.10.16 and Sambrook et al. (1989, supra) at sections 1.101 to 1.104.

While stringent washes are typically carried out at temperatures from about 42° C. to 68° C., one skilled in the art will appreciate that other temperatures may be suitable for stringent conditions. Maximum hybridization rate typically occurs at about 20° C. to 25° C. below the $T_m$ for formation of a DNA-DNA hybrid. It is well known in the art that the $T_m$ is the melting temperature, or temperature at which two complementary polynucleotide sequences dissociate. Methods for estimating $T_m$ are well known in the art (see Ausubel et al., supra at page 2.10.8).

In general, the $T_m$ of a perfectly matched duplex of DNA may be predicted as an approximation by the formula: $T_m = 81.5 + 16.6 (\log_{10} M) + 0.41 (\% G+C) - 0.63 (\% \text{formamide}) - (600/\text{length})$ wherein: M is the concentration of $Na^+$, preferably in the range of 0.01 molar to 0.4 molar; % G+C is the sum of guanosine and cytosine bases as a percentage of the total number of bases, within the range between 30% and 75% G+C; % formamide is the percent formamide concentration by volume; length is the number of base pairs in the DNA duplex. The $T_m$ of a duplex DNA decreases by approximately 1° C. with every increase of 1% in the number of randomly mismatched base pairs. Washing is generally carried out at $T_m$—15° C. for high stringency, or $T_m$—30° C. for moderate stringency.

In one example of a hybridization procedure, a membrane (e.g., a nitrocellulose membrane or a nylon membrane) containing immobilized DNA is hybridized overnight at 42° C. in a hybridization buffer (50% deionized formamide, 5×SSC, 5×Denhardt's solution (0.1% ficoll, 0.1% polyvinylpyrollidone and 0.1% bovine serum albumin), 0.1% SDS and 200 mg/mL denatured salmon sperm DNA) containing a labeled probe. The membrane is then subjected to two sequential medium stringency washes (i.e., 2×SSC, 0.1% SDS for 15 min at 45° C., followed by 2×SSC, 0.1% SDS for 15 min at 50° C.), followed by two sequential higher stringency washes (i.e., 0.2×SSC, 0.1% SDS for 12 min at 55° C. followed by 0.2×SSC and 0.1% SDS solution for 12 min at 65-68° C.

Embodiments of the present invention also include oligonucleotides, whether for detection, amplification, antisense therapies, or other purpose. For these and related purposes, the term "oligonucleotide" or "oligo" or "oligomer" is intended to encompass a singular "oligonucleotide" as well as plural "oligonucleotides," and refers to any polymer of two or more of nucleotides, nucleosides, nucleobases or related compounds used as a reagent in the amplification methods of the present invention, as well as subsequent detection methods. The oligonucleotide may be DNA and/or RNA and/or analogs thereof.

The term oligonucleotide does not necessarily denote any particular function to the reagent, rather, it is used generically to cover all such reagents described herein. An oligonucleotide may serve various different functions, e.g., it may function as a primer if it is capable of hybridizing to a complementary strand and can further be extended in the presence of a nucleic acid polymerase, it may provide a promoter if it contains a sequence recognized by an RNA polymerase and allows for transcription, and it may function to prevent hybridization or impede primer extension if appropriately situated and/or modified. An oligonucleotide may also function as a probe, or an antisense agent. An oligonucleotide can be virtually any length, limited only by its specific function, e.g., in an amplification reaction, in detecting an amplification product of the amplification reaction, or in an antisense or RNA interference application. Any of the oligonucleotides described herein can be used as a primer, a probe, an antisense oligomer, or an RNA interference agent.

The term "primer" as used herein refers to a single-stranded oligonucleotide capable of acting as a point of initiation for template-directed DNA synthesis under suitable conditions defined, for example, by buffer and temperature, in the presence of four different nucleoside triphosphates and an agent for polymerization, such as a DNA or RNA polymerase or reverse transcriptase. The length of the primer, in any given case, depends on, for example, the intended use of the primer, and generally ranges from about 15 to 30 nucleotides, although shorter and longer primers may be used. Short primer molecules generally require cooler temperatures to form sufficiently stable hybrid complexes with the template. A primer need not reflect the exact sequence of the template but must be sufficiently complementary to hybridize with such template. The primer site is the area of the template to which a primer hybridizes. The primer pair is a set of primers including a 5' upstream primer that hybridizes with the 5' end of the sequence to be amplified and a 3' downstream primer that hybridizes with the complement of the 3' end of the sequence to be amplified.

The term "probe" as used herein refers to a surface-immobilized molecule that can be recognized by a particular target. See, e.g., U.S. Pat. No. 6,582,908 for an example of arrays having all possible combinations of probes with 10, 12, and more bases. Probes and primers as used herein typically comprise at least 10-15 contiguous nucleotides of a known sequence. In order to enhance specificity, longer probes and primers may also be employed, such as probes and primers that comprise at least 20, 25, 30, 40, 50, 60, 70, 80, 90, 100, or at least 150 nucleotides of an HRS reference sequence or its complement. Probes and primers may be considerably longer than these examples, and it is understood that any length supported by the knowledge in the art and the specification, including the tables, figures, and Sequence Listing, may be used.

Methods for preparing and using probes and primers are described in the references, for example Sambrook, J. et al. (1989) Molecular Cloning: A Laboratory Manual, 2.sup.nd ed., vol. 1-3, Cold Spring Harbor Press, Plainview N.Y.; Ausubel, F. M. et al. (1987) Current Protocols in Molecular Biology, Greene Publ. Assoc. & Wiley-Intersciences, New York N.Y.; Innis, M. et al. (1990) PCR Protocols. A Guide to Methods and Applications, Academic Press, San Diego Calif. PCR primer pairs can be derived from a known sequence, for example, by using computer programs intended for that purpose such as Primer (Version 0.5, 1991, Whitehead Institute for Biomedical Research, Cambridge Mass.).

Oligonucleotides for use as primers or probes may be selected using software known in the art. For example, OLIGO 4.06 software is useful for the selection of PCR primer pairs of up to 100 nucleotides each, and for the analysis of oligonucleotides and larger polynucleotides of up to 5,000 nucleotides from an input polynucleotide sequence of up to 32 kilobases. The Primer3 primer selection program (available to the public from the Whitehead Institute/MIT Center for Genome Research, Cambridge Mass.) allows the user to input a "mispriming library," in which sequences to avoid as primer binding sites are user-specified. The oligonucleotides and polynucleotide fragments identified by any of the above selection methods are useful in hybridization technologies, for example, as PCR or sequencing primers, microarray elements, or specific probes to identify fully or partially complementary polynucleotides in a sample of nucleic acids. Methods of oligonucleotide selection are not limited to those described herein.

The terms "antisense oligomer" or "antisense compound" or "antisense oligonucleotide" are used interchangeably and refer to a sequence of cyclic subunits, each bearing a base-pairing moiety, linked by intersubunit linkages that allow the base-pairing moieties to hybridize to a target sequence in a nucleic acid (typically an RNA) by Watson-Crick base pairing, to form a nucleic acid:oligomer heteroduplex within the target sequence, and typically thereby prevent translation of that RNA. Also included are methods of use thereof to modulate expression of a selected HRS transcript, such as a splice variant or proteolytic fragment, and/or its corresponding polypeptide.

Antisense oligonucleotides may contain between about 8 and 40 subunits, typically about 8-25 subunits, and preferably about 12 to 25 subunits. In certain embodiments, oligonucleotides may have exact sequence complementarity to the target sequence or near complementarity, as defined below. In certain embodiments, the degree of complementarity between the target and antisense targeting sequence is sufficient to form a stable duplex. The region of complementarity of the antisense oligomers with the target RNA sequence may be as short as 8-11 bases, but is preferably 12-15 bases or more, e.g., 12-20 bases, or 12-25 bases, including all integers in between these ranges. An antisense oligomer of about 14-15 bases is generally long enough to have a unique complementary sequence in targeting the selected HRS transcript.

In certain embodiments, antisense oligomers as long as 40 bases may be suitable, where at least a minimum number of bases, e.g., 10-12 bases, are complementary to the target sequence. In general, however, facilitated or active uptake in cells is optimized at oligomer lengths less than about 30. For certain oligomers, described further below, an optimum balance of binding stability and uptake generally occurs at lengths of 18-25 bases. Included are antisense oligomers (e.g., PNAs, LNAs, 2'-OMe, MOE, morpholinos) that consist of about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 bases, in which at least about 6, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 contiguous or non-contiguous bases are complementary to their HRS target sequence, or variants thereof.

In certain embodiments, antisense oligomers may be 100% complementary to the HRS nucleic acid target sequence, or it may include mismatches, e.g., to accommodate variants, as long as a heteroduplex formed between the oligomer and HRS nucleic acid target sequence is sufficiently stable to withstand the action of cellular nucleases and other modes of degradation which may occur in vivo. Oligomer backbones which are less susceptible to cleavage by nucleases are discussed below. Mismatches, if present, are less destabilizing toward the end regions of the hybrid duplex than in the middle. The number of mismatches allowed will depend on the length of the oligomer, the percentage of G:C base pairs in the duplex, and the position of the mismatch(es) in the duplex, according to well understood principles of duplex stability. Although such an antisense oligomer is not necessarily 100% complementary to the HRS nucleic acid target sequence, it is effective to stably and specifically bind to the target sequence, such that a biological activity of the nucleic acid target, e.g., expression of HRS protein(s), is modulated.

The stability of the duplex formed between an oligomer and a target sequence is a function of the binding Tm and the susceptibility of the duplex to cellular enzymatic cleavage. The Tm of an antisense oligonucleotide with respect to complementary-sequence RNA may be measured by conventional methods, such as those described by Hames et al., Nucleic Acid Hybridization, IRL Press, 1985, pp. 107-108 or as described in Miyada C. G. and Wallace R. B., 1987, Oligonucleotide hybridization techniques, Methods Enzymol. Vol. 154 pp. 94-107. In certain embodiments, antisense oligomer may have a binding Tm, with respect to a complementary-sequence RNA, of greater than body temperature and preferably greater than 50° C. Tm's in the range 60-80° C. or greater are preferred. According to well known principles, the Tm of an oligomer compound, with respect to a complementary-based RNA hybrid, can be increased by increasing the ratio of C:G paired bases in the duplex, and/or by increasing the length (in base pairs) of the heteroduplex.

Antisense oligomers can be designed to block or inhibit translation of mRNA or to inhibit natural pre-mRNA splice processing, or induce degradation of targeted mRNAs, and may be said to be "directed to" or "targeted against" a target sequence with which it hybridizes. In certain embodiments, the target sequence may include any coding or non-coding sequence of an HRS mRNA transcript, and may thus by within an exon or within an intron. In certain embodiments, the target sequence is relatively unique or exceptional among HRSs and is selective for reducing expression of a selected HRS proteolytic fragment or splice variant. In certain embodiments, the target site includes a 3' or 5' splice site of a pre-processed mRNA, or a branch point. The target sequence for a splice site may include an mRNA sequence having its 5' end 1 to about 25 to about 50 base pairs downstream of a splice acceptor junction or upstream of a splice donor junction in a preprocessed mRNA. In certain embodiments, a target sequence may include a splice junction of an alternatively splice HRS mRNA, such as a splice junction that does not occur in the full-length HRS, or is unique or exceptional to that transcript, in that it either does not occur or only seldom occurs in other HRS splice variants. An oligomer is more generally said to be "targeted against" a biologically relevant target, such as reference HRS polynucleotide, when it is targeted against the nucleic acid of the target in the manner described herein.

A "subunit" of an oligonucleotide refers to one nucleotide (or nucleotide analog) unit. The term may refer to the nucleotide unit with or without the attached intersubunit linkage, although, when referring to a "charged subunit", the charge typically resides within the intersubunit linkage (e.g., a phosphate or phosphorothioate linkage or a cationic linkage).

The cyclic subunits of an oligonucleotide may be based on ribose or another pentose sugar or, in certain embodiments, alternate or modified groups. Examples of modified oligonucleotide backbones include, without limitation, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Also contemplated are peptide nucleic acids (PNAs), locked nucleic acids (LNAs), 2'-O-Methyl oligonucleotides (2'-OMe), 2'-methoxyethoxy oligonucleotides (MOE), morpholinos, among other oligonucleotides known in the art.

The purine or pyrimidine base pairing moiety is typically adenine, cytosine, guanine, uracil, thymine or inosine. Also included are bases such as pyridin-4-one, pyridin-2-one, phenyl, pseudouracil, 2,4,6-trime115thoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine), propyne, quesosine, 2-thiouridine, 4-thiouridine, wybutosine, wybutoxosine, 4-acetyltidine, 5-(carboxyhydroxymethyl)uridine, 5'-carboxymethylaminomethyl-2-thiouridine, 5-carboxymethylaminomethyluridine, β-D-galactosylqueosine, 1-methyladenosine, 1-methylinosine, 2,2-dimethylguanosine, 3-methylcytidine, 2-methyladenosine, 2-methylguanosine, N6-methyladenosine, 7-methylguanosine, 5-methoxyaminomethyl-2-thiouridine, 5-methylaminomethyluridine, 5-methylcarbonyhnethyluridine, 5-methyloxyuridine, 5-methyl-2-thiouridine, 2-methylthio-N6-isopentenyladenosine, β-D-mannosylqueosine, uridine-5-oxyacetic acid, 2-thiocytidine, threonine derivatives and others (Burgin et al., 1996, Biochemistry, 35, 14090; Uhlman & Peyman, supra). By "modified bases" in this aspect is meant nucleotide bases other than adenine (A), guanine (G), cytosine (C), thymine (T), and uracil (U), as illustrated above; such bases can be used at any position in the antisense molecule. Persons skilled in the art will appreciate that depending on the uses of the oligomers, Ts and Us are interchangeable. For instance, with other antisense chemistries such as 2'-O-methyl antisense oligonucleotides that are more RNA-like, the T bases may be shown as U.

An oligonucleotide is typically complementary to a target sequence, such as a target DNA or RNA. The terms "complementary" and "complementarity" refer to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. Or, there may be "complete" or "total" complementarity (100%) between the nucleic acids. The degree of complementarity between nucleic acid strands has significant effects on the efficiency and strength of hybridization between nucleic acid strands. While perfect complementarity is often desired, some embodiments can include one or more but preferably 20, 19, 18, 17, 16, 15, 14, 13, 12, 11, 10, 9, 8, 7, 6, 5, 4, 3, 2, or 1 mismatches with respect to the target sequence. Variations at any location within the oligomer are included. In certain embodiments, variations in sequence near the termini of an oligomer are generally preferable to variations in the interior, and if present are typically within about 10, 9, 8, 7, 6, 5, 4, 3, 2, or 1 nucleotides of the 5' and/or 3' terminus.

The term "target sequence" refers to a portion of the target RNA against which the oligonucleotide is directed, that is, the sequence to which the oligonucleotide will hybridize by Watson-Crick base pairing of a complementary sequence. In certain embodiments, the target sequence may be a contiguous region of an HRS mRNA (e.g., a unique splice junction of an HRS mRNA), or may be composed of non-contiguous regions of the mRNA.

The term "targeting sequence" or in certain embodiments "antisense targeting sequence" refers to the sequence in an oligonucleotide that is complementary (meaning, in addition, substantially complementary) to the target sequence in the DNA or RNA target molecule. The entire sequence, or only a portion, of the antisense compound may be complementary to the target sequence. For example, in an oligonucleotide having 20-30 bases, about 6, 7, 8, 9, 10, 11, 12, 13, 14, 15, 16, 17, 18, 19, 20, 21, 22, 23, 24, 25, 26, 27, 28, or 29 may be targeting sequences that are complementary to the target region. Typically, the targeting sequence is formed of contiguous bases, but may alternatively be formed of non-contiguous sequences that when placed together, e.g., from opposite ends of the oligonucleotide, constitute sequence that spans the target sequence.

Target and targeting sequences are described as "complementary" to one another when hybridization occurs in an antiparallel configuration. A targeting sequence may have "near" or "substantial" complementarity to the target sequence and still function for the purpose of the present invention, that is, it may still be functionally "complementary."

An oligonucleotide "specifically hybridizes" to a target polynucleotide if the oligomer hybridizes to a target (e.g., an HRS reference polynucleotide or its complement) under physiological conditions, with a Tm substantially greater than 45° C., preferably at least 50° C., and typically 60° C.-80° C. or higher. Such hybridization preferably corresponds to stringent hybridization conditions. At a given ionic strength and pH, the Tm is the temperature at which 50% of a target sequence hybridizes to a complementary polynucleotide. Again, such hybridization may occur with "near" or "substantial" complementarity of the antisense oligomer to the target sequence, as well as with exact complementarity.

The terms specifically binds or specifically hybridizes refer generally to an oligonucleotide probe or polynucleotide sequence that not only binds to its intended target gene sequence in a sample under selected hybridization conditions, but does not bind significantly to other target sequences in the sample, and thereby discriminates between its intended target and all other targets in the target pool. A probe that specifically hybridizes to its intended target sequence may also detect concentration differences under the selected hybridization conditions, as described herein.

As noted above, certain oligonucleotides provided herein include peptide nucleic acids (PNAs). Also included are "locked nucleic acid" subunits (LNAs). The structures of LNAs are known in the art: for example, Wengel, et al., Chemical Communications (1998) 455; Tetrahedron (1998) 54, 3607, and Accounts of Chem. Research (1999) 32, 301); Obika, et al., Tetrahedron Letters (1997) 38, 8735; (1998) 39, 5401, and Bioorganic Medicinal Chemistry (2008)16, 9230. Certain oligonucleotides may comprise morpholino-based subunits bearing base-pairing moieties, joined by uncharged or substantially uncharged linkages. The terms "morpholino oligomer" or "PMO" (phosphoramidate- or phosphorodiamidate morpholino oligomer) refer to an oligonucleotide analog composed of morpholino subunit structures, where (i) the structures are linked together by phosphorus-containing linkages, one to three atoms long, preferably two atoms long, and preferably uncharged or cationic, joining the morpholino nitrogen of one subunit to a 5' exocyclic carbon of an adjacent subunit, and (ii) each morpholino ring bears a purine or pyrimidine or an equivalent base-pairing moiety effective to bind, by base specific hydrogen bonding, to a base in a polynucleotide.

In certain embodiments, oligonucleotides can be prepared by stepwise solid-phase synthesis, employing methods detailed in the references cited above, and below with respect to the synthesis of oligonucleotides having a mixture or uncharged and cationic backbone linkages. In some cases, it may be desirable to add additional chemical moieties to the oligonucleotide, e.g., to enhance pharmacokinetics or to facilitate capture or detection of the compound. Such a moiety may be covalently attached, typically to a terminus of the oligomer, according to standard synthetic methods. For example, addition of a polyethylene glycol moiety or other hydrophilic polymer, e.g., one having 10-100 monomeric subunits, may be useful in enhancing solubility. One or more charged groups, e.g., anionic charged groups such as an organic acid, may enhance cell uptake.

A variety of detectable molecules may be used to render an oligonucleotide detectable, such as a radioisotopes, fluorochromes, dyes, enzymes, nanoparticles, chemiluminescent markers, biotin, or other monomer known in the art that can be detected directly (e.g., by light emission) or indirectly (e.g., by binding of a fluorescently-labeled antibody).

Certain embodiments relate to RNA interference (RNAi) agents that target one or more mRNA transcripts of an HRS reference polynucleotide, including fragments and variants thereof. Also included are methods of use thereof to modulate the levels of a selected HRS transcript, such as an HRS splice variant or proteolytic fragment.

The term "double-stranded" means two separate nucleic acid strands comprising a region in which at least a portion of the strands are sufficiently complementary to hydrogen bond and form a duplex structure. The term "duplex" or "duplex structure" refers to the region of a double stranded molecule wherein the two separate strands are substantially complementary, and thus hybridize to each other. "dsRNA" refers to a ribonucleic acid molecule having a duplex structure comprising two complementary and anti-parallel nucleic acid strands (i.e., the sense and antisense strands). Not all nucleotides of a dsRNA must exhibit Watson-Crick base pairs; the two RNA strands may be substantially complementary. The RNA strands may have the same or a different number of nucleotides.

The strands of a dsRNA are sufficiently complementary to hybridize to form a duplex structure. In certain embodiments, the complementary RNA strand may be less than 30 nucleotides, less than 25 nucleotides in length, or even 19 to 24 nucleotides in length. In certain aspects, the complementary nucleotide sequence may be 20-23 nucleotides in length, or 22 nucleotides in length.

In certain embodiments, at least one of the RNA strands comprises a nucleotide overhang of 1 to 4 nucleotides in length. In other embodiments, one or both of the strands are blunt-ended. In certain embodiments, the dsRNA may further comprise at least one chemically modified nucleotide.

Certain embodiments of the present invention may comprise microRNAs. Micro-RNAs represent a large group of small RNAs produced naturally in organisms, some of which regulate the expression of target genes. Micro-RNAs are formed from an approximately 70 nucleotide single-stranded hairpin precursor transcript by Dicer. (V. Ambros et al. Current Biology 13:807, 2003).

Certain embodiments may also employ short-interfering RNAs (siRNA). Each strand of an siRNA agent can be equal to or less than 35, 30, 25, 24, 23, 22, 21, 20, 19, 18, 17, 16, or 15 nucleotides in length. The strand is preferably at least 19 nucleotides in length. For example, each strand can be between 21 and 25 nucleotides in length. Preferred siRNA agents have a duplex region of 17, 18, 19, 29, 21, 22, 23, 24, or 25 nucleotide pairs, and one or more overhangs, preferably one or two 3' overhangs, of 2-3 nucleotides.

A "single strand RNAi agent" as used herein, is an RNAi agent which is made up of a single molecule. It may include a duplexed region, formed by intrastrand pairing, e.g., it may be, or include, a hairpin or pan-handle structure. A single strand RNAi agent is at least 14, and more preferably at least 15, 20, 25, 29, 35, 40, or 50 nucleotides in length. It is preferably less than 200, 100, or 60 nucleotides in length.

Hairpin RNAi modulating agents may have a duplex region equal to or at least 17, 18, 19, 29, 21, 22, 23, 24, or 25 nucleotide pairs. The duplex region may preferably be equal to or less than 200, 100, or 50, in length. Certain ranges for the duplex region are 15-30, 17 to 23, 19 to 23, and 19 to 21 nucleotides pairs in length. The hairpin may have a single strand overhang or terminal unpaired region, preferably the 3', and preferably of the antisense side of the hairpin. In certain embodiments, overhangs are 2-3 nucleotides in length.

The present invention further encompasses oligonucleotides employing ribozymes. Also included are vector delivery systems that are capable of expressing the HRS-targeting sequences described herein. Included are vectors that express siRNA or other duplex-forming RNA interference molecules. Exemplary delivery systems may include viral vector systems (i.e., viral-mediated transduction) including, but not limited to, retroviral (e.g., lentiviral) vectors, adenoviral vectors, adeno-associated viral vectors, and herpes viral vectors, among others known in the art.

Oligonucleotides and RNAi agents that target one or more portions of an HRS polynucleotide reference sequence or its complement may be used in any of the therapeutic, diagnostic, or drug screening methods described herein and apparent to persons skilled in the art.

Antibody Compositions, Fragments Thereof and Other Binding Agents

According to another aspect, the present invention further provides binding agents, such as antibodies, antigen-binding fragments thereof, soluble receptors, aptamers, small molecules, etc., that exhibit binding specificity for a HRS splice variant polypeptide or its cellular binding partner as disclosed herein, or to a portion, variant or derivative thereof, and methods of using same.

In some embodiments, such binding agents will be effective for modulating one or more of the non-canonical activities mediated by a HRS polypeptide of the invention. In certain other embodiments, for example, the binding agent is one that binds to a HRS polypeptide of the invention and inhibits its ability to bind to one or more of its cellular binding partners. Accordingly, such binding agents may be used to treat or prevent diseases, disorders or other conditions that are mediated by, or modulated by, a HRS polypeptide of the invention by antagonizing it activity. In certain embodiments, for example, the binding agent binds to the cellular binding partner of an HRS polypeptide, and mimics the HRS polypeptide activity, such as by increasing or agonizing the non-canonical activity mediated by the HRS polypeptide. Accordingly, such binding agents may be used to diagnose, treat, or prevent diseases, disorders or other conditions that are mediated by an HRS polypeptide of the invention, such as by antagonizing or agonizing its activity partially or fully.

An binding agent such as an antibody, or antigen-binding fragment thereof, is said to "specifically bind," "immunologically bind," and/or is "immunologically reactive" to a polypeptide of the invention if it reacts at a detectable level (within, for example, an ELISA assay) with the polypeptide, and does not react detectably with unrelated polypeptides under similar conditions.

Immunological binding, as used in this context, generally refers to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and on geometric parameters that equally influence the rate in both directions. Thus, both the "on rate constant" ($K_{on}$) and the "off rate constant" ($K_{off}$) can be determined by calculation of the concentrations and the actual rates of association and dissociation. The ratio of $K_{off}/K_{on}$ enables cancellation of all parameters not related to affinity, and is thus equal to the dissociation constant $K_d$. See, e.g., Davies et al. (1990) Annual Rev. Biochem. 59:439-473.

An "antigen-binding site," or "binding portion" of an antibody, refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions," or "FRs". Thus the term "FR" refers to amino acid sequences which are naturally found between and adjacent to hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs."

A binding agent may be, for example, a ribosome, with or without a peptide component, an RNA molecule or a polypeptide. In a preferred embodiment, a binding agent is an antibody or an antigen-binding fragment thereof. Antibodies may be prepared by any of a variety of techniques known to those of ordinary skill in the art. See, e.g., Harlow and Lane, *Antibodies: A Laboratory Manual*, Cold Spring Harbor Laboratory, 1988. Monoclonal antibodies specific for a polypeptide of interest may be prepared, for example, using the technique of Kohler and Milstein, Eur. J. Immunol. 6:511-519, 1976, and improvements thereto. The polypeptides of this invention may be used in the purification process in, for example, an affinity chromatography step.

An "Fv" fragment can be produced by preferential proteolytic cleavage of an IgM, and on rare occasions IgG or IgA immunoglobulin molecule. Fv fragments are, however, more commonly derived using recombinant techniques known in the art. The Fv fragment includes a non-covalent $V_H::V_L$ heterodimer including an antigen-binding site which retains much of the antigen recognition and binding capabilities of the native antibody molecule. Inbar et al. (1972) Proc. Nat. Acad. Sci. USA 69:2659-2662; Hochman et al. (1976) Biochem 15:2706-2710; and Ehrlich et al. (1980) Biochem 19:4091-4096.

A single chain Fv ("sFv") polypeptide is a covalently linked $V_H::V_L$ heterodimer which is expressed from a gene fusion including $V_H$- and $V_L$-encoding genes linked by a peptide-encoding linker. Huston et al. (1988) Proc. Nat. Acad. Sci. USA 85(16):5879-5883. A number of methods have been described to discern chemical structures for converting the naturally aggregated—but chemically separated—light and heavy polypeptide chains from an antibody V region into an sFv molecule which will fold into a three dimensional structure substantially similar to the structure of an antigen-binding site. See, e.g., U.S. Pat. Nos. 5,091,513 and 5,132,405, to Huston et al.; and U.S. Pat. No. 4,946,778, to Ladner et al.

Each of the above-described molecules includes a heavy chain and a light chain CDR set, respectively interposed between a heavy chain and a light chain FR set which provide support to the CDRS and define the spatial relationship of the CDRs relative to each other. As used herein, the term "CDR set" refers to the three hypervariable regions of a heavy or light chain V region. Proceeding from the N-terminus of a heavy or light chain, these regions are denoted as "CDR1," "CDR2," and "CDR3" respectively. An antigen-binding site, therefore, includes six CDRs, comprising the CDR set from each of a heavy and a light chain V region. A polypeptide comprising a single CDR, (e.g., a CDR1, CDR2 or CDR3) is referred to herein as a "molecular recognition unit." Crystallographic analysis of a number of antigen-antibody complexes has demonstrated that the amino acid residues of CDRs form extensive contact with bound antigen, wherein the most extensive antigen contact is with the heavy chain CDR3. Thus, the molecular recognition units are primarily responsible for the specificity of an antigen-binding site.

As used herein, the term "FR set" refers to the four flanking amino acid sequences which frame the CDRs of a CDR set of a heavy or light chain V region. Some FR residues may contact bound antigen; however, FRs are primarily responsible for folding the V region into the antigen-binding site, particularly the FR residues directly adjacent to the CDRS. Within FRs, certain amino residues and certain structural features are very highly conserved. In this regard, all V region sequences contain an internal disulfide loop of around 90 amino acid residues. When the V regions fold into a binding-site, the CDRs are displayed as projecting loop motifs which form an antigen-binding surface. It is generally recognized that there are conserved structural regions of FRs which influence the folded shape of the CDR loops into certain "canonical" structures—regardless of the precise CDR amino acid sequence. Further, certain FR residues are known to participate in non-covalent interdomain contacts which stabilize the interaction of the antibody heavy and light chains.

A number of "humanized" antibody molecules comprising an antigen-binding site derived from a non-human immunoglobulin have been described, including chimeric antibodies having rodent V regions and their associated CDRs fused to human constant domains (Winter et al. (1991) Nature 349:293-299; Lobuglio et al. (1989) Proc. Nat. Acad. Sci. USA 86:4220-4224; Shaw et al. (1987) J Immunol. 138:4534-4538; and Brown et al. (1987) Cancer Res. 47:3577-3583), rodent CDRs grafted into a human supporting FR prior to fusion with an appropriate human antibody constant domain (Riechmann et al. (1988) Nature 332:323-327; Verhoeyen et al. (1988) Science 239:1534-

1536; and Jones et al. (1986) Nature 321:522-525), and rodent CDRs supported by recombinantly veneered rodent FRs (European Patent Publication No. 519,596, published Dec. 23, 1992). These "humanized" molecules are designed to minimize unwanted immunological response toward rodent antihuman antibody molecules which limits the duration and effectiveness of therapeutic applications of those moieties in human recipients.

As noted above, "peptides" are included as binding agents. The term peptide typically refers to a polymer of amino acid residues and to variants and synthetic analogues of the same. In certain embodiments, the term "peptide" refers to relatively short polypeptides, including peptides that consist of about 2, 3, 4, 5, 6, 7, 8, 9, 10, 11, 12, 13, 14, 15, 16, 17, 18, 19, 20, 25, 30, 35, 40, 45, or 50 amino acids, including all integers and ranges (e.g., 5-10, 8-12, 10-15) in between, and interact with an HRS polypeptide, its cellular binding partner, or both. Peptides can be composed of naturally-occurring amino acids and/or non-naturally occurring amino acids, as described herein.

A binding agent may include a peptide mimetic or other small molecule. A "small molecule" refers to an organic compound that is of synthetic or biological origin (biomolecule), but is typically not a polymer. Organic compounds refer to a large class of chemical compounds whose molecules contain carbon, typically excluding those that contain only carbonates, simple oxides of carbon, or cyanides. A "biomolecule" refers generally to an organic molecule that is produced by a living organism, including large polymeric molecules (biopolymers) such as peptides, polysaccharides, and nucleic acids as well, and small molecules such as primary secondary metabolites, lipids, phospholipids, glycolipids, sterols, glycerolipids, vitamins, and hormones. A "polymer" refers generally to a large molecule or macromolecule composed of repeating structural units, which are typically connected by covalent chemical bond.

In certain embodiments, a small molecule has a molecular weight of less than 1000 Daltons, typically between about 300 and 700 Daltons, and including about 50, 100, 150, 200, 250, 300, 350, 400, 450, 500, 550, 500, 650, 600, 750, 700, 850, 800, 950, or 1000 Daltons.

Aptamers are also included as binding agents. Examples of aptamers included nucleic acid aptamers (e.g., DNA aptamers, RNA aptamers) and peptide aptamers. Nucleic acid aptamers refer generally to nucleic acid species that have been engineered through repeated rounds of in vitro selection or equivalent method, such as SELEX (systematic evolution of ligands by exponential enrichment), to bind to various molecular targets such as small molecules, proteins, nucleic acids, and even cells, tissues and organisms. Hence, included are nucleic acid aptamers that bind to the HRS polypeptides described herein and/or their cellular binding partners.

Peptide aptamers typically include a variable peptide loop attached at both ends to a protein scaffold, a double structural constraint that typically increases the binding affinity of the peptide aptamer to levels comparable to that of an antibody's (e.g., in the nanomolar range). In certain embodiments, the variable loop length may be composed of about 10-20 amino acids (including all integers in between), and the scaffold may include any protein that has good solubility and compacity properties. Certain exemplary embodiments may utilize the bacterial protein Thioredoxin-A as a scaffold protein, the variable loop being inserted within the reducing active site (-Cys-Gly-Pro-Cys- loop in the wild protein), with the two cysteines lateral chains being able to form a disulfide bridge. Hence, included are peptide aptamers that bind to the HRS polypeptides described herein and/or their cellular binding partners. Peptide aptamer selection can be performed using different systems known in the art, including the yeast two-hybrid system.

As noted above, the HRS polypeptides and binding agents of the present invention can be used in any of the diagnostic, drug discovery, or therapeutic methods described herein.

In another embodiment of the invention, binding agents such as monoclonal antibodies of the present invention may be coupled to one or more agents of interest. For example, a therapeutic agent may be coupled (e.g., covalently bonded) to a suitable monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al.

Where a therapeutic agent is more potent when free from the antibody portion of the immunoconjugates of the present invention, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671,958, to Rodwell et al.), and acid-catalyzed hydrolysis (e.g., U.S. Pat. No. 4,569,789, to Blattler et al.).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers that provide multiple sites for attachment can be used.

Formulation and Administration

The compositions of the invention (e.g., HRS splice variant polypeptides, polynucleotides, binding agents, antibodies, etc.) are generally formulated in pharmaceutically-acceptable or physiologically-acceptable solutions for administration to a cell, tissue or animal, either alone, or in combination with one or more other modalities of therapy. It will also be understood that, if desired, the compositions of the invention may be administered in combination with other agents as well, such as, e.g., other proteins or polypeptides or various pharmaceutically-active agents. There is virtually no limit to other components that may also be included in the compositions, provided that the additional agents do not adversely affect the effects desired to be achieved with a HRS composition of the invention.

In the pharmaceutical compositions of the invention, formulation of pharmaceutically-acceptable excipients and carrier solutions is well-known to those of skill in the art, as is the development of suitable dosing and treatment approaches for using the particular compositions described herein in a variety of treatment regimens, including e.g., oral, parenteral, intravenous, intranasal, intracranial and intramuscular administration and formulation.

In certain applications, the pharmaceutical compositions disclosed herein may be delivered via oral administration to a subject. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain circumstances it will be desirable to deliver the pharmaceutical compositions disclosed herein parenterally, intravenously, intramuscularly, or even intraperitoneally as described, for example, in U.S. Pat. Nos. 5,543,158; 5,641,515 and 5,399,363 (each specifically incorporated herein by reference in its entirety). Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form should be sterile and should be fluid to the extent that easy syringability exists. It should be stable under the conditions of manufacture and storage and should be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion (see, e.g., *Remington's Pharmaceutical Sciences*, 15th Edition, pp. 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and the general safety and purity standards as required by FDA Office of Biologics standards.

Sterile injectable solutions can be prepared by incorporating the active compounds in the required amount in the appropriate solvent with the various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" refers to molecular entities and compositions that do not produce an allergic or similar untoward reaction when administered to a human or other mammal. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

In certain embodiments, the pharmaceutical compositions may be delivered by intranasal sprays, inhalation, and/or other aerosol delivery vehicles. Methods for delivering genes, polynucleotides, and peptide compositions directly to the lungs via nasal aerosol sprays has been described e.g., in U.S. Pat. Nos. 5,756,353 and 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

In certain embodiments, the delivery may occur by use of liposomes, nanocapsules, microparticles, microspheres, lipid particles, vesicles, and the like, for the introduction of the compositions of the present invention into suitable host cells. In particular, the compositions of the present invention may be formulated for delivery either encapsulated in a lipid particle, a liposome, a vesicle, a nanosphere, a nanoparticle or the like. The formulation and use of such delivery vehicles can be carried out using known and conventional techniques.

Kits comprising Compositions of the Invention

The invention, in other aspects, provides kits comprising one or more containers filled with one or more of the HRS splice variant polypeptides, polynucleotides, antibodies, compositions thereof, etc., of the invention, as described herein. The kits can include written instructions on how to use such compositions (e.g., to modulate cellular signaling, angiogenesis, cancer, inflammatory conditions, etc.).

The kits herein may also include a one or more additional therapeutic agents or other components suitable or desired for the indication being treated. An additional therapeutic agent may be contained in a second container, if desired. Examples of additional therapeutic agents include, but are not limited to antineoplastic agents, anti-inflammatory agents, antibacterial agents, antiviral agents, angiogenic agents, etc.

The kits herein can also include one or more syringes or other components necessary or desired to facilitate an intended mode of delivery (e.g., stents, implantable depots, etc.).

Methods of Use

Embodiments of the present invention also include methods of using the HRS compositions or "agents" described herein for diagnostic, drug discovery, and/or therapeutic purposes. The term HRS "agents" refers generally to the HRS polynucleotides, HRS polypeptides, binding agents, and other compounds described herein. For diagnostic purposes, the HRS agents can be used in a variety of non-limiting ways, such as to distinguish between different cell types or different cellular states, or to identify subjects having a relevant disease or condition. For drug discovery purposes, the HRS agents can be used to identify one or more cellular "binding partners" of an HRS polypeptide, characterize one or more "non-canonical" activities of an HRS polypeptide, identify agents that selectively or non-selectively agonize or antagonize the interaction of an HRS polypeptide with its binding partner(s), and/or identify agents that selectively or non-selectively agonize or antagonize one or more "non-canonical" activities of an HRS polypeptide. For therapeutic purposes, the HRS agents or compositions provided herein can be used to treat a variety of diseases or conditions, detailed below.

A. Diagnostics

As noted above, HRS agents described herein can be used in diagnostic assays. These embodiments include the detection of the HRS polynucleotide sequence(s) or corresponding polypeptide sequence(s) or portions thereof of one or more newly identified HRS splice variants, and/or one or more splice junctions of those splice variants. In certain embodiments, the polynucleotide or corresponding polypeptide sequence(s) of at least one of the splice junctions is unique to that particular HRS splice variant. In certain embodiments, the presence or levels of one or more newly identified HRS splice variants, as typically characterized by the polynucleotide or corresponding polypeptide sequence of their splice junctions, associate or correlate with one or more cellular types or cellular states. Hence, as noted above, the presence or levels of an HRS splice variant or its splice junction can be used to distinguish between different cellular types or different cellular states. The presence or levels of HRS splice variants or their splice junctions can be detected according to polynucleotide and/or polypeptide-based diagnostic techniques.

Certain of the methods provided herein rely on the differential expression of an HRS splice variant to characterize the condition or state of a cell, tissue, or subject, and to distinguish it from another cell, tissue, or subject. Non-limiting examples include methods of detecting the presence or levels of an HRS splice variant or its splice junction in a biological sample to distinguish between cells or tissues of different species, cells of different tissues or organs, cellular developmental states such as neonatal and adult, cellular differentiation states, conditions such as healthy, diseased and treated, intracellular and extracellular fractions, in addition to primary cell cultures and other cell cultures, such as immortalized cell cultures.

Differential expression refers generally to a statistically significant difference in one or more gene expression levels of an HRS polynucleotide or polypeptide sequence compared to the expression levels of the same sequence in an appropriate control. The statistically significant difference may relate to either an increase or a decrease in expression levels, as measured by RNA levels, protein levels, protein function, or any other relevant measure of gene expression such as those described herein.

A result is typically referred to as statistically significant if it is unlikely to have occurred by chance. The significance level of a test or result relates traditionally to a frequentist statistical hypothesis testing concept. In simple cases, statistical significance may be defined as the probability of making a decision to reject the null hypothesis when the null hypothesis is actually true (a decision known as a Type I error, or "false positive determination"). This decision is often made using the p-value: if the p-value is less than the significance level, then the null hypothesis is rejected. The smaller the p-value, the more significant the result. Bayes factors may also be utilized to determine statistical significance (see, e.g., Goodman S., *Ann Intern Med* 130:1005-13, 1999).

In more complicated, but practically important cases, the significance level of a test or result may reflect an analysis in which the probability of making a decision to reject the null hypothesis when the null hypothesis is actually true is no more than the stated probability. This type of analysis allows for those applications in which the probability of deciding to reject may be much smaller than the significance level for some sets of assumptions encompassed within the null hypothesis.

In certain exemplary embodiments, statistically significant differential expression may include situations wherein the expression level of a given HRS sequence provides at least about a 1.2×, 1.3×, 1.4×, 1.5×, 1.6×, 1.7×, 1.8×, 1.9×, 2.0×, 2.2×, 2.4×, 2.6×, 2.8×, 3.0×, 4.0×, 5.0×, 6.0×, 7.0×, 8.0×, 9.0×, 10.0×, 15.0×, 20.0×, 50.0×, 100.0×, or greater difference in expression (i.e., differential expression that may be higher or lower expression) in a suspected biological sample as compared to an appropriate control, including all integers and decimal points in between (e.g., 1.24×, 1.25×, 2.1×, 2.5×, 60.0×, 75.0×, etc.). In certain embodiments, statistically significant differential expression may include situations wherein the expression level of a given HRS sequence provides at least about 4, 5, 6, 7, 8, 9, 10, 11, 12, 13, 14, 15, 16, 17, 18, 19, 20, 25, 30, 35, 40, 45, 50, 60, 70, 80, 90, 100, 200, 300, 400, 500, 600, 700, 800, 900, 1000 percent (%) or greater difference in expression (i.e., differential expression that may be higher or lower) in a suspected biological sample as compared to an appropriate control, including all integers and decimal points in between.

As an additional example, differential expression may also be determined by performing Z-testing, i.e., calculating an absolute Z score, as described herein and known in the art (see Example 1). Z-testing is typically utilized to identify significant differences between a sample mean and a population mean. For example, as compared to a standard normal table (e.g., a control tissue), at a 95% confidence interval (i.e., at the 5% significance level), a Z-score with an absolute value greater than 1.96 indicates non-randomness. For a 99% confidence interval, if the absolute Z is greater than 2.58, it means that p<0.01, and the difference is even more significant—the null hypothesis can be rejected with greater confidence. In these and related embodiments, an absolute Z-score of 1.96, 2, 2.58, 3, 4, 5, 6, 7, 8, 9, 10, 11, 12, 13, 14, 15, 16, 17, 18, 19, 20 or more, including all decimal points in between (e.g., 10.1, 10.6, 11.2, etc.), may provide a strong measure of statistical significance. In certain embodiments, an absolute Z-score of greater than 6 may provide exceptionally high statistical significance.

Substantial similarly relates generally to the lack of a statistically significant difference in the expression levels between the biological sample and the reference control. Examples of substantially similar expression levels may include situations wherein the expression level of a given SSCIGS provides less than about a 0.05×, 0.1×, 0.2×, 0.3×, 0.4×, 0.5×, 0.6×, 0.7×, 0.8×, 0.9×. 1.0×, 1.1×, 1.2×, 1.3×, or 1.4× difference in expression (i.e., differential expression that may be higher or lower expression) in a suspected biological sample as compared to a reference sample, including all decimal points in between (e.g., 0.15×, 0.25×, 0.35×, etc.). In certain embodiments, differential expression may include situations wherein the expression level of a given HRS sequence provides less than about 0.25, 0.5, 1, 2, 3, 4, 5, 6, 7, 8, 9, 10, 11, 12, 13, 14, 15, 16, 17, 18, 19, 20, 30, 40, 50 percent (%) difference in expression (i.e., differential expression that may be higher or lower) in a suspected biological sample as compared to a reference sample, including all decimal points in between.

In certain embodiments, such as when using an Affymetrix Microarray to measure the expression levels of an HRS polynucleotide or polypeptide sequence, differential expression may also be determined by the mean expression value summarized by Affymetrix Microarray Suite 5 software (Affymetrix, Santa Clara, Calif.), or other similar software, typically with a scaled mean expression value of 1000.

Embodiments of the present invention include methods of detecting the presence or levels of an HRS polynucleotide or polypeptide reference sequence or a portion thereof to distinguish between cells, tissues, or other biological samples of a different organism or species, wherein the presence or levels of that sequence associates with a selected organism or species. General examples include methods of distinguishing between humans and any combination of bacteria, fungi, plants, and other non-human animals. Included within animals are methods of distinguishing between humans and any combination of vertebrates and invertebrates, including vertebrates such as fish, amphibians, reptiles, birds, and non-human mammals, and invertebrates such as insects, mollusks, crustaceans, and corals. Included within non-human mammals are methods of distinguishing between humans and any combination of non-human mammals from the Order Afrosoricida, Macroscelidea, Tubulidentata, Hyracoidea, Proboscidea, Sirenia, Cingulata, Pilosa, Scandentia, Dermoptera, Primates, Rodentia, Lagomorpha, Erinaceomorpha, Soricomorpha, Chiroptera, Pholidota, Cetacea, Carnivora, Perissodactyla, or Artiodactyla. Included within the Primate Order are monkeys, apes, gorillas, and chimpanzees, among others known in the art. Accordingly, the presence or levels of an HRS polynucleotide or polypeptide reference sequence or variant, as described herein, may be used to identify the source of a given biological sample, such as a cell, tissue, or organ, by distinguishing between any combination of these organisms, or by distinguishing between humans and any one or more of these organisms, such as a panel of organisms. In certain embodiments, the source of a given biological sample may also be determined by comparing the presence or levels of an HRS sequence or a portion thereof to a pre-determined value.

Embodiments of the present invention include methods of detecting the presence or levels of an HRS polynucleotide or polypeptide reference sequence or a portion thereof to distinguish between cells or other biological samples that originate from different tissues or organs. Non-limiting examples include methods of distinguishing between a cell or other biological sample that originates from any combination of skin (e.g., dermis, epidermis, subcutaneous layer), hair follicles, nervous system (e.g., brain, spinal cord, peripheral nerves), auditory system or balance organs (e.g., inner ear, middle ear, outer ear), respiratory system (e.g., nose, trachea, lungs), gastroesophogeal tissues, the gastrointestinal system (e.g., mouth, esophagus, stomach, small intestines, large intestines, rectum), vascular system (e.g., heart, blood vessels and arteries), liver, gallbladder, lymphatic/immune system (e.g., lymph nodes, lymphoid follicles, spleen, thymus, bone marrow), uro-genital system (e.g., kidneys, ureter, bladder, urethra, cervix, Fallopian tubes, ovaries, uterus, vulva, prostate, bulbourethral glands, epidiymis, prostate, seminal vesicles, testicles), musculoskeletal system (e.g., skeletal muscles, smooth muscles, bone, cartilage, tendons, ligaments), adipose tissue, mammaries, and the endocrine system (e.g., hypothalamus, pituitary, thyroid, pancreas, adrenal glands). Hence, based on the association of an HRS polynucleotide or polypeptide sequence as described herein, these methods may be used to identify or characterize the tissue or organ from which a cell or other biological sample is derived.

Embodiments of the present invention include methods of detecting the presence or levels of an HRS polynucleotide or polypeptide reference sequence or a portion thereof to distinguish between or characterize the developmental or differentiation state of the cell. Also included are methods of differentiating between germ cells, stem cells, and somatic cells. Examples of developmental states include neonatal and adult. Examples of cellular differentiation states include all of the discreet and identifiable stages between a totipotent cell, a pluripotent cell, a multipotent progenitor stem cell and a mature, fully differentiated cell.

A totipotent cell has total potential, typically arises during sexual and asexual reproduction, and includes and spores and zygotes, though in certain instances cells can dedifferentiate and regain totipotency. A pluripotent cell includes a stem cell that has the potential to differentiate into any of the three germ layers, including the endoderm (interior stomach lining, gastrointestinal tract, the lungs), the mesoderm (muscle, bone, blood, urogenital), and the ectoderm (epidermal tissues and nervous system). Multipotent progenitor cells are typically capable of differentiating into a limited number of tissue types. Examples of multipotent cells include, without limitation, hematopoietic stem cells (adult stem cells) from the bone marrow that give rise to immune cells such as red blood cells, white blood cells, and platelets, mesenchymal stem cells (adult stem cells) from the bone marrow that give rise to stromal cells, fat cells, and various types of bone cells, epithelial stem cells (progenitor cells) that give rise to the various types of skin cells, and muscle satellite cells (progenitor cells) that contribute to differentiated muscle tissue. Accordingly, the presence or levels of particular HRS polynucleotide or polypeptide sequence (e.g., splice junction of an HRS splice variant), can be used to distinguish between or characterize the above-noted cellular differentiation states, as compared to a control or a predetermined level.

Embodiments of the present invention include methods of detecting the presence or levels of an HRS polynucleotide or polypeptide reference sequence to characterize or diagnose the condition or a cell, tissue, organ, or subject, in which that condition may be characterized as healthy, diseased, at risk for being diseased, or treated. For such diagnostic purposes, the term "diagnostic" or "diagnosed" includes identifying the presence or nature of a pathologic condition, characterizing the risk of developing such a condition, and/or measuring the change (or no change) of a pathologic condition in response to therapy. Diagnostic methods may differ in their sensitivity and specificity. In certain embodiments, the "sensitivity" of a diagnostic assay refers to the percentage of diseased cells, tissues or subjects which test positive (percent of "true positives"). Diseased cells, tissues or subjects not detected by the assay are typically referred to as "false negatives." Cells, tissues or subjects that are not diseased and which test negative in the assay may be termed "true negatives." In certain embodiments, the "specificity" of a diagnostic assay may be defined as one (1) minus the false positive rate, where the "false positive" rate is defined as the proportion of those samples or subjects without the disease and which test positive. While a particular diagnostic method may not provide a definitive diagnosis of a condition, it suffices if the method provides a positive indication that aids in diagnosis.

In certain instances, the presence or risk of developing a pathologic condition can be diagnosed by comparing the presence or levels of one or more selected HRS polynucleotide or polypeptide reference sequences or portions thereof that correlate with the condition, whether by increased or decreased levels, as compared to a suitable control. A "suitable control" or "appropriate control" includes a value, level, feature, characteristic, or property determined in a cell or other biological sample of a tissue or organism, e.g., a control or normal cell, tissue or organism, exhibiting, for example, normal traits, such as the absence of the condition. In certain embodiments, a "suitable control" or "appropriate control" is a predefined value, level, feature, characteristic, or property. Other suitable controls will be apparent to persons skilled in the art. Examples of diseases and conditions are described elsewhere herein.

Embodiments of the present invention include HRS polynucleotide or nucleic acid-based detection techniques, which offer certain advantages due to sensitivity of detection. Hence, certain embodiments relate to the use or detection of HRS polynucleotides as part of a diagnostic method or assay. The presence and/or levels of HRS polynucleotides may be measured by any method known in the art, including hybridization assays such as Northern blot, quantitative or qualitative polymerase chain reaction (PCR), quantitative or qualitative reverse transcriptase PCR (RT-PCR), microarray, dot or slot blots, or in situ hybridization such as fluorescent in situ hybridization (FISH), among others. Certain of these methods are described in greater detail below.

HRS polynucleotides such as DNA and RNA can be collected and/or generated from blood, biological fluids, tissues, organs, cell lines, or other relevant sample using techniques known in the art, such as those described in Kingston. (2002 *Current Protocols in Molecular Biology*, Greene Publ. Assoc. Inc. & John Wiley & Sons, Inc., N.Y., NY (see, e.g., as described by Nelson et al. *Proc Natl Acad Sci USA*, 99: 11890-11895, 2002) and elsewhere.

Complementary DNA (cDNA) libraries can be generated using techniques known in the art, such as those described in Ausubel et al. (2001 *Current Protocols in Molecular Biology*, Greene Publ. Assoc. Inc. & John Wiley & Sons, Inc., N.Y., NY); Sambrook et al. (1989 Molecular Cloning, Second Ed., Cold Spring Harbor Laboratory, Plainview, N.Y.); Maniatis et al. (1982 *Molecular Cloning*, Cold Spring Harbor Laboratory, Plainview, N.Y.) and elsewhere.

Certain embodiments may employ hybridization methods for detecting HRS polynucleotide sequences. Methods for conducting polynucleotide hybridization assays have been well developed in the art. Hybridization assay procedures and conditions will vary depending on the application and are selected in accordance with the general binding methods known including those referred to in: Maniatis et al. Molecular Cloning: A Laboratory Manual (2nd Ed. Cold Spring Harbor, N.Y., 1989); Berger and Kimmel Methods in Enzymology, Vol. 152, Guide to Molecular Cloning Techniques (Academic Press, Inc., San Diego, Calif., 1987); Young and Davism, P.N.A.S, 80: 1194 (1983). Methods and apparatus for carrying out repeated and controlled hybridization reactions have been described in U.S. Pat. Nos. 5,871,928, 5,874,219, 6,045,996 and 6,386,749, 6,391,623 each of which are incorporated herein by reference Certain embodiments may employ nucleic acid amplification methods for detecting HRS polynucleotide sequences. The term "amplification" or "nucleic acid amplification" refers to the production of multiple copies of a target nucleic acid that contains at least a portion of the intended specific target nucleic acid sequence. The multiple copies may be referred to as amplicons or amplification products. In certain embodiments, the amplified target contains less than the complete target gene sequence (introns and exons) or an expressed target gene sequence (spliced transcript of exons and flanking untranslated sequences). For example, specific amplicons may be produced by amplifying a portion of the target polynucleotide by using amplification primers that hybridize to, and initiate polymerization from, internal positions of the target polynucleotide. Preferably, the amplified portion contains a detectable target sequence that may be detected using any of a variety of well-known methods.

"Selective amplification" or "specific amplification," as used herein, refers to the amplification of a target nucleic acid sequence according to the present invention wherein detectable amplification of the target sequence is substantially limited to amplification of target sequence contributed by a nucleic acid sample of interest that is being tested and is not contributed by target nucleic acid sequence contributed by some other sample source, e.g., contamination present in reagents used during amplification reactions or in the environment in which amplification reactions are performed.

By "amplification conditions" is meant conditions permitting nucleic acid amplification according to the present invention. Amplification conditions may, in some embodiments, be less stringent than "stringent hybridization conditions" as described herein. Oligonucleotides used in the amplification reactions of the present invention hybridize to their intended targets under amplification conditions, but may or may not hybridize under stringent hybridization conditions. On the other hand, detection probes of the present invention typically hybridize under stringent hybridization conditions. Acceptable conditions to carry out nucleic acid amplifications according to the present invention can be easily ascertained by someone having ordinary skill in the art depending on the particular method of amplification employed.

Many well-known methods of nucleic acid amplification require thermocycling to alternately denature double-stranded nucleic acids and hybridize primers; however, other well-known methods of nucleic acid amplification are isothermal. The polymerase chain reaction (U.S. Pat. Nos. 4,683,195; 4,683,202; 4,800,159; 4,965,188), commonly referred to as PCR, uses multiple cycles of denaturation, annealing of primer pairs to opposite strands, and primer extension to exponentially increase copy numbers of the target sequence. In a variation called RT-PCR, reverse transcriptase (RT) is used to make a complementary DNA (cDNA) from mRNA, and the cDNA is then amplified by PCR to produce multiple copies of DNA.

As noted above, the term "PCR" refers to multiple amplification cycles that selectively amplify a target nucleic acid species. Included are quantitative PCR (qPCR), real-time PCR), reverse transcription PCR (RT-PCR) and quantitative reverse transcription PCR (qRT-PCR) is well described in the art. The term "pPCR" refers to quantitative polymerase chain reaction, and the term "qRT-PCR" refers to quantitative reverse transcription polymerase chain reaction. qPCR and qRT-PCR may be used to amplify and simultaneously quantify a targeted cDNA molecule. It enables both detection and quantification of a specific sequence in a cDNA pool, such as a selected HRS gene or transcript.

The term "real-time PCR" may use DNA-binding dye to bind to all double-stranded (ds) DNA in PCR, causing fluorescence of the dye. An increase in DNA product during PCR therefore leads to an increase in fluorescence intensity and is measured at each cycle, thus allowing DNA concentrations to be quantified. However, dsDNA dyes such as SYBR Green will bind to all dsDNA PCR products. Fluorescence is detected and measured in the real-time PCR thermocycler, and its geometric increase corresponding to exponential increase of the product is used to determine the threshold cycle ("Ct") in each reaction.

The term "Ct Score" refers to the threshold cycle number, which is the cycle at which PCR amplification has surpassed a threshold level. If there is a higher quantity of mRNA for a particular gene in a sample, it will cross the threshold earlier than a lowly expressed gene since there is more starting RNA to amplify. Therefore, a low Ct score indicates high gene expression in a sample and a high Ct score is indicative of low gene expression.

Certain embodiments may employ the ligase chain reaction (Weiss, R. 1991, Science 254: 1292), commonly referred to as LCR, which uses two sets of complementary DNA oligonucleotides that hybridize to adjacent regions of the target nucleic acid. The DNA oligonucleotides are covalently linked by a DNA ligase in repeated cycles of thermal denaturation, hybridization and ligation to produce a detectable double-stranded ligated oligonucleotide product.

In certain embodiments, other techniques may be used to evaluate RNA transcripts of the transcripts from a particular cDNA library, including microarray analysis (Han, M., et al., *Nat Biotechnol*, 19: 631-635, 2001; Bao, P., et al., *Anal Chem*, 74: 1792-1797, 2002; Schena et al., *Proc. Natl. Acad. Sci. USA* 93:10614-19, 1996; and Heller et al., *Proc. Natl. Acad. Sci. USA* 94:2150-55, 1997) and SAGE (serial analysis of gene expression). Like MPSS, SAGE is digital and can generate a large number of signature sequences. (see e.g., Velculescu, V. E., et al., *Trends Genet*, 16: 423-425, 2000; Tuteja R. and Tuteja N. Bioessays. 2004 August; 26(8):916-22), although orders of magnitude fewer than that are available from techniques such as MPSS.

In certain embodiments, the term "microarray" includes a "nucleic acid microarray" having a substrate-bound plurality of nucleic acids, hybridization to each of the plurality of bound nucleic acids being separately detectable. The substrate can be solid or porous, planar or non-planar, unitary or distributed. Nucleic acid microarrays include all the devices so called in Schena (ed.), DNA Microarrays: A Practical Approach (Practical Approach Series), Oxford University Press (1999); Nature Genet. 21(1) (suppl.): 1-60 (1999); Schena (ed.), Microarray Biochip: Tools and Technology, Eaton Publishing Company/BioTechniques Books Division (2000). Nucleic acid microarrays may include a substrate-bound plurality of nucleic acids in which the plurality of nucleic acids are disposed on a plurality of beads, rather than on a unitary planar substrate, as described, for example, in Brenner et al., *Proc. Natl. Acad. Sci. USA* 97(4): 1665-1670 (2000). Examples of nucleic acid microarrays may be found in U.S. Pat. Nos. 6,391,623, 6,383,754, 6,383,749, 6,380,377, 6,379,897, 6,376,191, 6,372,431, 6,351,712 6,344,316, 6,316,193, 6,312,906, 6,309,828, 6,309,824, 6,306,643, 6,300,063, 6,287,850, 6,284,497, 6,284,465, 6,280,954, 6,262,216, 6,251,601, 6,245,518, 6,263,287, 6,251,601, 6,238,866, 6,228,575, 6,214,587, 6,203,989, 6,171,797, 6,103,474, 6,083,726, 6,054,274, 6,040,138, 6,083,726, 6,004,755, 6,001,309, 5,958,342, 5,952,180, 5,936,731, 5,843,655, 5,814,454, 5,837,196, 5,436,327, 5,412,087, and 5,405,783, the disclosures of which are incorporated by reference.

Additional examples include nucleic acid arrays that are commercially available from Affymetrix (Santa Clara, Calif.) under the brand name GeneChip™. Further exemplary methods of manufacturing and using arrays are provided in, for example, U.S. Pat. Nos. 7,028,629; 7,011,949; 7,011,945; 6,936,419; 6,927,032; 6,924,103; 6,921,642; and 6,818,394.

The present invention as related to arrays and microarrays also contemplates many uses for polymers attached to solid substrates. These uses include gene expression monitoring, profiling, library screening, genotyping and diagnostics. Gene expression monitoring and profiling methods and methods useful for gene expression monitoring and profiling are shown in U.S. Pat. Nos. 5,800,992, 6,013,449, 6,020, 135, 6,033,860, 6,040,138, 6,177,248 and 6,309,822. Genotyping and uses therefore are shown in U.S. Ser. Nos. 10/442,021, 10/013,598 (U.S. Application No. 2003/0036069), and U.S. Pat. Nos. 5,925,525, 6,268,141, 5,856,092, 6,267,152, 6,300,063, 6,525,185, 6,632,611, 5,858,659, 6,284,460, 6,361,947, 6,368,799, 6,673,579 and 6,333,179. Other methods of nucleic acid amplification, labeling and analysis that may be used in combination with the methods disclosed herein are embodied in U.S. Pat. Nos. 5,871,928, 5,902,723, 6,045,996, 5,541,061, and 6,197,506.

As will be apparent to persons skilled in the art, certain embodiments may employ oligonucleotides, such as primers or probes, for amplification or detection, as described herein. While the design and sequence of oligonucleotides depends on their function as described herein, several variables are generally taken into account. Among the most relevant are: length, melting temperature (Tm), specificity, complementarity with other oligonucleotides in the system, G/C content, polypyrimidine (T, C) or polypurine (A, G) stretches, and the 3'-end sequence.

Certain embodiments therefore include methods for detecting a target HRS polynucleotide in a sample, typically wherein the polynucleotide comprises the sequence of a reference HRS polynucleotide described herein, comprising a) hybridizing the sample with a probe comprising a sequence complementary to the target polynucleotide in the sample, and which probe specifically hybridizes to said target polynucleotide, under conditions whereby a hybridization complex is formed between said probe and said target polynucleotide or fragments thereof, and b) detecting the presence or absence of said hybridization complex, and optionally, if present, the amount thereof. Also included are methods for detecting a target HRS polynucleotide in a sample, the polynucleotide comprising the sequence of a reference HRS polynucleotide, as described herein, comprising a) amplifying the target polynucleotide or fragment thereof, and b) detecting the presence or absence of said amplified target polynucleotide or fragment thereof, and, optionally, if present, the amount thereof.

Embodiments of the present invention include a variety of HRS polypeptide-based detection techniques, including antibody-based detection techniques. Included in these embodiments are the use of HRS polypeptides to generate antibodies or other binders, which may then be used in diagnostic methods and compositions to detect or quantitate selected HRS polypeptides in a cell or other biological sample, typically from a subject.

Certain embodiments may employ standard methodologies such as western blotting and immunoprecipitation, enzyme-linked immunosorbent assays (ELISA), flow cytometry, and immunofluorescence assays (IFA). These well-known methods typically utilize one or more monoclonal or polyclonal antibodies as described herein that specifically bind to a selected HRS polypeptide of the invention, or a unique region of that HRS polypeptide, and generally do not bind significantly to other HRS polypeptides, such as a full-length HRS polypeptide. In certain embodiments, the unique region of the HRS polypeptide may be encoded by a unique splice junction or a particular three-dimensional structure of a newly identified alternate splice variant.

Certain embodiments may employ "arrays," such as "microarrays." In certain embodiments, a "microarray" may also refer to a "peptide microarray" or "protein microarray" having a substrate-bound collection or plurality of polypeptides, the binding to each of the plurality of bound polypeptides being separately detectable. Alternatively, the peptide microarray may have a plurality of binders, including but not limited to monoclonal antibodies, polyclonal antibodies, phage display binders, yeast 2 hybrid binders, and aptamers, which can specifically detect the binding of the HRS polypeptides described herein. The array may be based on autoantibody detection of these HRS polypeptides, as described, for example, in Robinson et al., *Nature Medicine* 8(3):295-301 (2002). Examples of peptide arrays may be found in WO 02/31463, WO 02/25288, WO 01/94946, WO 01/88162, WO 01/68671, WO 01/57259, WO 00/61806, WO 00/54046, WO 00/47774, WO 99/40434, WO 99/39210, and WO 97/42507 and U.S. Pat. Nos. 6,268,210, 5,766,960, and 5,143,854, each of which are incorporated by reference.

Certain embodiments may employ MS or other molecular weight-based methods for diagnostically detecting HRS polypeptide sequences. Mass spectrometry (MS) refers generally to an analytical technique for determining the elemental composition of a sample or molecule. MS may also be used for determining the chemical structures of molecules, such as peptides and other chemical compounds.

Generally, the MS principle consists of ionizing chemical compounds to generate charged molecules or molecule fragments, and then measuring their mass-to-charge ratios. In an illustrative MS procedure: a sample is loaded onto the MS instrument, and undergoes vaporization, the components of the sample are ionized by one of a variety of methods (e.g., by impacting them with an electron beam), which results in the formation of positively charged particles, the positive ions are then accelerated by a magnetic field, computations are performed on the mass-to-charge ratio (m/z) of the particles based on the details of motion of the ions as they transit through electromagnetic fields, and, detection of the ions, which in step prior were sorted according to m/z.

An illustrative MS instruments has three modules: an ion source, which converts gas phase sample molecules into ions (or, in the case of electrospray ionization, move ions that exist in solution into the gas phase); a mass analyzer, which sorts the ions by their masses by applying electromagnetic fields; and a detector, which measures the value of an indicator quantity and thus provides data for calculating the abundances of each ion present.

The MS technique has both qualitative and quantitative uses, including identifying unknown compounds, determining the isotopic composition of elements in a molecule, and determining the structure of a compound by observing its fragmentation. Other uses include quantifying the amount of a compound in a sample or studying the fundamentals of gas phase ion chemistry (the chemistry of ions and neutrals in a vacuum). Accordingly, MS techniques may be used according to any of the methods provided herein to measure the presence or levels of an HRS polypeptide of the invention in a biological sample, and to compare those levels to a control sample or a pre-determined value.

B. Discovery of Compounds and Therapeutic Agents

Certain embodiments relate to the use of HRS polypeptide or HRS polynucleotide references sequences in drug discovery, typically to identify agents that modulate one or more of the non-canonical activities of the reference HRS. For example, certain embodiments include methods of identifying one or more "binding partners" of an HRS reference polypeptide, or a polypeptide that comprises an HRS reference sequence such as a cellular protein or other host molecule that associates with the HRS polypeptide and participates in its non-canonical activity or activities. Also included are methods of identifying a compound (e.g., polypeptide) or other agent that agonizes or antagonizes the non-canonical activity of an HRS reference polypeptide or active variant thereof, such as by interacting with the HRS polypeptide and/or one or more of its cellular binding partners.

Certain embodiments therefore include methods of identifying a binding partner of an HRS reference polypeptide, comprising a) combining the HRS polypeptide with a biological sample under suitable conditions, and b) detecting specific binding of the HRS polypeptide to a binding partner, thereby identifying a binding partner that specifically binds to the HRS reference polypeptide. Also included are methods of screening for a compound that specifically binds to an HRS reference polypeptide or a binding partner of the HRS polypeptide, comprising a) combining the polypeptide or the binding partner with at least one test compound under suitable conditions, and b) detecting binding of the polypeptide or the binding partner to the test compound, thereby identifying a compound that specifically binds to the polypeptide or its binding partner. In certain embodiments, the compound is a polypeptide or peptide. In certain embodiments, the compound is a small molecule or other (e.g., non-biological) chemical compound. In certain embodiments, the compound is a peptide mimetic.

Any method suitable for detecting protein-protein interactions may be employed for identifying cellular proteins that interact with an HRS reference polypeptide, interact with one or more of its cellular binding partners, or both. Examples of traditional methods that may be employed include co-immunoprecipitation, cross-linking, and co-purification through gradients or chromatographic columns of cell lysates or proteins obtained from cell lysates, mainly to identify proteins in the lysate that interact with the HRS polypeptide.

In these and related embodiments, at least a portion of the amino acid sequence of a protein that interacts with an HRS polypeptide or its binding partner can be ascertained using techniques well known to those of skill in the art, such as via the Edman degradation technique. See, e.g., Creighton Proteins: Structures and Molecular Principles, W.H. Freeman & Co., N.Y., pp. 34 49, 1983. The amino acid sequence obtained may be used as a guide for the generation of oligonucleotide mixtures that can be used to screen for gene sequences encoding such proteins. Screening may be accomplished, for example, by standard hybridization or PCR techniques, as described herein and known in the art. Techniques for the generation of oligonucleotide mixtures and the screening are well known. See, e.g., Ausubel et al. Current Protocols in Molecular Biology Green Publishing Associates and Wiley Interscience, N.Y., 1989; and Innis et al., eds. PCR Protocols: A Guide to Methods and Applications Academic Press, Inc., New York, 1990.

Additionally, methods may be employed in the simultaneous identification of genes that encode the binding partner or other polypeptide. These methods include, for example, probing expression libraries, in a manner similar to the well known technique of antibody probing of lam bda-gt11 libraries, using labeled HRS protein, or another polypeptide, peptide or fusion protein, e.g., a variant HRS polypeptide or HRS domain fused to a marker (e.g., an enzyme, fluor, luminescent protein, or dye), or an Ig-Fc domain.

One method that detects protein interactions in vivo is the two-hybrid system. An example of this system has been described (Chien et al., *PNAS USA* 88:9578 9582, 1991) and is commercially available from Clontech (Palo Alto, Calif.). In certain instances, the two-hybrid system or other such methodology may be used to screen activation domain libraries for proteins that interact with the "bait" gene product. By way of example, and not by way of limitation, an HRS reference polypeptide or variant may be used as the bait gene product. An HRS binding partner may also be used as a "bait" gene product. Total genomic or cDNA sequences are fused to the DNA encoding an activation domain. This library and a plasmid encoding a hybrid of a bait HRS gene product fused to the DNA-binding domain are co-transformed into a yeast reporter strain, and the resulting transformants are screened for those that express the reporter gene.

Also included are three-hybrid systems, which allow the detection of RNA-protein interactions in yeast. See, e.g., Hook et al., *RNA*. 11:227-233, 2005. Accordingly, these and related methods can be used to identify a cellular binding partner of an HRS polypeptide. These and related methods can also be used to identify other compounds such as binding agents or nucleic acids that interact with the HRS polypeptide, its cellular binding partner, or both.

As noted above, once isolated, binding partners can be identified and can, in turn, be used in conjunction with standard techniques to identify proteins or other compounds with which it interacts. Certain embodiments thus relate to methods of screening for a compound that specifically binds to the binding partner of an HRS reference polypeptide, comprising a) combining the binding partner with at least one test compound under suitable conditions, and b) detecting binding of the binding partner to the test compound, thereby identifying a compound that specifically binds to the binding partner. In certain embodiments, the test compound is a polypeptide. In certain embodiments, the test compound is a chemical compound, such as a small molecule compound or peptide mimetic.

Certain embodiments include methods of screening for a compound that modulates the activity of an HRS reference polypeptide, comprising a) combining the polypeptide with at least one test compound under conditions permissive for the activity of the polypeptide, b) assessing the activity of the polypeptide in the presence of the test compound, and c) comparing the activity of the polypeptide in the presence of the test compound with the activity of the polypeptide in the absence of the test compound, wherein a change in the activity of the polypeptide in the presence of the test compound is indicative of a compound that modulates the activity of the polypeptide.

Certain embodiments include methods of screening for a compound that modulates the activity of a binding partner of an HRS reference polypeptide, comprising a) combining the polypeptide with at least one test compound under conditions permissive for the activity of the binding partner, b) assessing the activity of the binding partner in the presence of the test compound, and c) comparing the activity of the binding partner in the presence of the test compound with the activity of the binding partner in the absence of the test compound, wherein a change in the activity of the binding partner in the presence of the test compound is indicative of a compound that modulates the activity of the binding partner. Typically, these and related embodiments include assessing a selected non-canonical activity that is associated with the HRS polypeptide or its binding partner. Included are in vitro and in vivo conditions, such as cell culture conditions.

Certain embodiments include methods of screening a compound for effectiveness as a full or partial agonist of an HRS reference polypeptide or an active fragment or variant thereof, comprising a) exposing a sample comprising the polypeptide to a compound, and b) detecting agonist activity in the sample, typically by measuring an increase in the non-canonical activity of the HRS polypeptide. Certain methods include a) exposing a sample comprising a binding partner of the HRS polypeptide to a compound, and b) detecting agonist activity in the sample, typically by measuring an increase in the selected non-canonical activity of the HRS polypeptide. Certain embodiments include compositions that comprise an agonist compound identified by the method and a pharmaceutically acceptable carrier or excipient.

Also included are methods of screening a compound for effectiveness as a full or partial antagonist of an HRS reference polypeptide, comprising a) exposing a sample comprising the polypeptide to a compound, and b) detecting antagonist activity in the sample, typically by measuring a decrease in the non-canonical activity of the HRS polypeptide. Certain methods include a) exposing a sample comprising a binding partner of the HRS polypeptide to a compound, and b) detecting antagonist activity in the sample, typically by measuring a decrease in the selected non-canonical activity of the HRS polypeptide. Certain embodiments include compositions that comprise an antagonist compound identified by the method and a pharmaceutically acceptable carrier or excipient.

In certain embodiments, in vitro systems may be designed to identify compounds capable of interacting with or modulating an HRS reference sequence or its binding partner. Certain of the compounds identified by such systems may be useful, for example, in modulating the activity of the pathway, and in elaborating components of the pathway itself. They may also be used in screens for identifying compounds that disrupt interactions between components of the pathway; or may disrupt such interactions directly. One exemplary approach involves preparing a reaction mixture of the HRS polypeptide and a test compound under conditions and for a time sufficient to allow the two to interact and bind, thus forming a complex that can be removed from and/or detected in the reaction mixture In vitro screening assays can be conducted in a variety of ways. For example, an HRS polypeptide, a cellular binding partner, or test compound(s) can be anchored onto a solid phase. In these and related embodiments, the resulting complexes may be captured and detected on the solid phase at the end of the reaction. In one example of such a method, the HRS polypeptide and/or its binding partner are anchored onto a solid surface, and the test compound(s), which are not anchored, may be labeled, either directly or indirectly, so that their capture by the component on the solid surface can be detected. In other examples, the test compound(s) are anchored to the solid surface, and the HRS polypeptide and/or its binding partner, which are not anchored, are labeled or in some way detectable. In certain embodiments, microtiter plates may conveniently be utilized as the solid phase. The anchored component (or test compound) may be immobilized by non-covalent or covalent attachments. Non-covalent attachment may be accomplished by simply coating the solid surface with a solution of the protein and drying. Alternatively, an immobilized antibody, preferably a monoclonal antibody, specific for the protein to be immobilized may be used to anchor the protein to the solid surface. The surfaces may be prepared in advance and stored.

To conduct an exemplary assay, the non-immobilized component is typically added to the coated surface containing the anchored component. After the reaction is complete, un-reacted components are removed (e.g., by washing) under conditions such that any specific complexes formed will remain immobilized on the solid surface. The detection of complexes anchored on the solid surface can be accomplished in a number of ways. For instance, where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the previously non-immobilized component (the antibody, in turn, may be directly labeled or indirectly labeled with a labeled anti-Ig antibody).

Alternatively, the presence or absence of binding of a test compound can be determined, for example, using surface plasmon resonance (SPR) and the change in the resonance angle as an index, wherein an HRS polypeptide or a cellular binding partner is immobilized onto the surface of a commercially available sensorchip (e.g., manufactured by Biacore™) according to a conventional method, the test compound is contacted therewith, and the sensorchip is illuminated with a light of a particular wavelength from a particular angle. The binding of a test compound can also be measured by detecting the appearance of a peak corresponding to the test compound by a method wherein an HRS polypeptide or a cellular binding partner is immobilized onto the surface of a protein chip adaptable to a mass spectrometer, a test compound is contacted therewith, and an ionization method such as MALDI-MS, ESI-MS, FAB-MS and the like is combined with a mass spectrometer (e.g., double-focusing mass spectrometer, quadrupole mass spectrometer, time-of-flight mass spectrometer, Fourier transformation mass spectrometer, ion cyclotron mass spectrometer and the like).

In certain embodiments, cell-based assays, membrane vesicle-based assays, or membrane fraction-based assays can be used to identify compounds that modulate interactions in the non-canonical pathway of the selected HRS polypeptide. To this end, cell lines that express an HRS polypeptide and/or a binding partner, or a fusion protein containing a domain or fragment of such proteins (or a combination thereof), or cell lines (e.g., COS cells, CHO cells, HEK293 cells, Hela cells etc.) that have been genetically engineered to express such protein(s) or fusion protein(s) can be used. Test compound(s) that influence the non-canonical activity can be identified by monitoring a change (e.g., a statistically significant change) in that activity as compared to a control or a predetermined amount.

For embodiments that relate to antisense and RNAi agents, for example, also included are methods of screening a compound for effectiveness in altering expression of an HRS reference polynucleotide, comprising a) exposing a sample comprising the HRS reference polynucleotide to a compound such as a potential antisense oligonucleotide, and b) detecting altered expression of the HRS polynucleotide. In certain non-limiting examples, these and related embodiments can be employed in cell-based assays or in cell-free translation assays, according to routine techniques in the art. Also included are the antisense and RNAi agents identified by such methods.

Also included are any of the above methods, or other screening methods known in the art, which are adapted for high-throughput screening (HTS). HTS typically uses automation to run a screen of an assay against a library of candidate compounds, for instance, an assay that measures an increase or a decrease in a non-canonical activity, as described herein.

C. Methods of Treatment

In another aspect, the present invention relates to methods of using the compositions of the present invention for treating a cell, tissue or subject with a composition as described herein. The cells or tissue that may be modulated by the present invention are preferably mammalian cells, or more preferably human cells. Such cells can be of a healthy state or of a diseased state.

Accordingly, the HRS agents described herein, including HRS polypeptides, HRS polynucleotides, HRS polynucleotide-based vectors, antisense oligonucleotides, RNAi agents, as well as binding agents such as peptides, antibodies and antigen-binding fragments, peptide mimetics and other small molecules, can be used to treat a variety of non-limiting diseases or conditions associated with the non-canonical activities of a reference HRS. Examples of such non-canonical activities include modulation of cell proliferation, modulation of cell migration, modulation of cell differentiation (e.g., hematopoiesis), modulation of apoptosis or other forms of cell death, modulation of cell signaling, modulation of angiogenesis, modulation of cell binding, modulation of cellular metabolism, modulation of cytokine production or activity, modulation of cytokine receptor activity, modulation of inflammation, and the like.

Included are polynucleotide-based therapies, such as antisense therapies and RNAi interference therapies, which typically relate to reducing the expression of a target molecule, such as a particular splice variant of an HRS polypeptide or a cellular binding partner of an HRS polypeptide, which otherwise contributes to its non-canonical activity. Antisense or RNAi therapies typically antagonize the non-canonical activity, such as by reducing expression of the HRS reference polypeptide. Also included are polypeptides, antibodies, peptide mimetics, or other small molecule-based therapies, which either agonize or antagonize the non-canonical activity of an HRS reference polypeptide, such as by interacting directly with the HRS polypeptide, its cellular binding partner(s), or both.

In certain embodiments, for example, methods are provided for modulating therapeutically relevant cellular activities including, but not limited to, cellular metabolism, cell differentiation, cell proliferation, cell death, cell mobilization, cell migration, immune system function, gene transcription, mRNA translation, cell impedance, cytokine production, and the like, comprising contacting a cell with a HRS composition as described herein. Accordingly, the HRS compositions may be employed in treating essentially any cell or tissue or subject that would benefit from modulation of one or more such activities.

The HRS compositions may also be used in any of a number of therapeutic contexts including, for example, those relating to the treatment or prevention of neoplastic diseases, immune system diseases (e.g., autoimmune diseases and inflammation), infectious diseases, metabolic diseases, neuronal/neurological diseases, muscular/cardiovascular diseases, diseases associated with aberrant hematopoiesis, diseases associated with aberrant angiogenesis, diseases associated with aberrant cell survival, and others.

For example, the compositions of the invention may be used as immunomodulators for treating anti- or pro-inflammatory indications by modulating the cells that mediate, either directly or indirectly, autoimmune and/or inflammatory disease, conditions and disorders. The utility of the compositions of the invention as immunomodulators can be monitored using any of a number of known and available techniques in the art including, for example, migration assays (e.g., using leukocytes, lymphocytes, monocytes), cytokine production assays, cell viability assays (e.g., using B-cells, T-cells, monocytes, NK cells), and the like.

"Inflammation" refers generally to the biological response of tissues to harmful stimuli, such as pathogens, damaged cells (e.g., wounds), and irritants. The term "inflammatory response" refers to the specific mechanisms by which inflammation is achieved and regulated, including, merely by way of illustration, immune cell activation or migration, cytokine production, vasodilation, including kinin release, fibrinolysis, and coagulation, among others described herein and known in the art. Ideally, inflammation is a protective attempt by the body to both remove the injurious stimuli and initiate the healing process for the affected tissue or tissues. In the absence of inflammation, wounds and infections would never heal, creating a situation in which progressive destruction of the tissue would threaten survival. On the other hand, excessive or chronic inflammation may associate with a variety of diseases, such as hay fever, atherosclerosis, and rheumatoid arthritis, among others described herein and known in the art.

Clinical signs of chronic inflammation are dependent upon duration of the illness, inflammatory lesions, cause and anatomical area affected. (see, e.g., Kumar et al., Robbins Basic Pathology-8$^{th}$ Ed., 2009 Elsevier, London; Miller, L M, Pathology Lecture Notes, Atlantic Veterinary College, Charlottetown, PEI, Canada). Chronic inflammation is associated with a variety of pathological conditions or diseases, including, for example, allergies, Alzheimer's disease, anemia, aortic valve stenosis, arthritis such as rheumatoid arthritis and osteoarthritis and arthritic gout, cancer, congestive heart failure, fibromyalgia, fibrosis, heart attack, kidney failure, lupus, pancreatitis, stroke, surgical complications, inflammatory lung disease, inflammatory bowel disease, atherosclerosis, neurological disorders, diabetes, metabolic disorders, obesity, and psoriasis, among others described herein and known in the art. Hence, HRS compositions may be used to treat or manage chronic inflammation, modulate any of one or more of the individual chronic inflammatory responses, or treat any one or more diseases or conditions associated with chronic inflammation.

Criteria for assessing the signs and symptoms of inflammatory and other conditions, including for purposes of making differential diagnosis and also for monitoring treatments such as determining whether a therapeutically effective dose has been administered in the course of treatment, e.g., by determining improvement according to accepted clinical criteria, will be apparent to those skilled in the art and are exemplified by the teachings of e.g., Berkow et al., eds., The Merck Manual, 16th edition, Merck and Co., Rahway, N.J., 1992; Goodman et al., eds., Goodman and Gilman's The Pharmacological Basis of Therapeutics, 10th edition, Pergamon Press, Inc., Elmsford, N.Y., (2001); Avery's Drug Treatment: Principles and Practice of Clinical Pharmacology and Therapeutics, 3rd edition, ADIS Press, Ltd., Williams and Wilkins, Baltimore, Md. (1987); Ebadi, Pharmacology, Little, Brown and Co., Boston, (1985); Osolci al., eds., Remington's Pharmaceutical Sciences, 18th edition, Mack Publishing Co., Easton, Pa. (1990); Katzung, Basic and Clinical Pharmacology, Appleton and Lange, Norwalk, Conn. (1992).

Also included are methods of modulating an immune response, such as an innate immune response. As used herein, the term "immune response" includes a measurable or observable reaction to an antigen, vaccine composition, or immunomodulatory molecule mediated by one or more cells of the immune system. An immune response typically begins with an antigen or immunomodulatory molecule binding to an immune system cell. A reaction to an antigen or immunomodulatory molecule may be mediated by many cell types, including a cell that initially binds to an antigen or immunomodulatory molecule and cells that participate in mediating an innate, humoral, cell-mediated immune response.

An "innate immune response," as used herein, may involve binding of pathogen-associated molecular patterns (PAMPs) or an HRS polypeptide to cell surface receptors, such as toll-like receptors. Activation of toll-like receptors and Ipaf-signaling pathways in response to PAMPs or other signals leads to the production of immunomodulatory molecules, such as cytokines and co-stimulatory molecules, which induce and/or enhance an immune response. Cells involved in the innate immune response include, for example, dendritic cells, macrophages, natural killer cells, and neutrophils, among others.

Certain embodiments relate to increasing an innate immune response. Other embodiments relate to decreasing an innate immune response. In certain aspects, an innate immune response is mediated by one or more toll-like receptors (TLRs), such as TLR2 and/or TLR4. Certain HRS polypeptides of the invention bind to TLRS such as TLR2 and/or TLR4. TLRs recognize PAMPs that distinguish infectious agents from self and mediating the production of immunomodulatory molecules, such as cytokines, necessary for the development of effective adaptive immunity (Aderem, A and Ulevitch, R. J. *Nature* 406: 782-787 (2000) and Brightbill, H. D., *Immunology* 101: 1-10 (2000), herein incorporated by reference). Members of the toll-like receptor family recognize a variety of antigen types and can discriminate between pathogens. For example, TLR2 recognizes various fungal, Gram-positive, and mycobacterial components, TLR4 recognizes the Gram-negative product lipopolysaccharide (LPS), and TLR9 recognizes nucleic acids such as CpG repeats in bacterial DNA.

HRS compositions that stimulate innate immunity (e.g., via TLR2 and/r TLR4) can be useful in the treatment of a wide variety of conditions, either alone or in combination with other therapies. Specific examples of such conditions include infectious diseases, such as bacterial, viral, and parasitic infectious diseases. HRS compositions that stimulate innate immunity can also be useful as vaccine adjuvants, to enhance a subject's immune response to the primary antigen, whether in a live, attenuated, or other type of vaccine.

Examples of viral infectious diseases or agents (and their corresponding vaccines) include, but are not limited to, Hepatitis A, Hepatitis B, Hepatitis C, Hepatitis E, Caliciviruses associated diarrhoea, Rotavirus diarrhoea, *Haemophilus influenzae* B pneumonia and invasive disease, influenza, measles, mumps, rubella, Parainfluenza associated pneumonia, Respiratory syncytial virus (RSV) pneumonia, Severe Acute Respiratory Syndrome (SARS), Human papillomavirus, Herpes simplex type 2 genital ulcers, HIV/AIDS, Dengue Fever, Japanese encephalitis, Tick-borne encephalitis, West-Nile virus associated disease, Yellow Fever, Epstein-Barr virus, Lassa fever, Crimean-Congo haemorrhagic fever, Ebola haemorrhagic fever, Marburg haemorrhagic fever, Rabies, Rift Valley fever, Smallpox, leprosy, upper and lower respiratory infections, poliomyelitis, among others described elsewhere herein.

Examples of bacterial infections disease or agents include, but are not limited to, *Bacillus antracis, Borellia burgdorferi, Brucella abortus, Brucella canus, Brucella melitensis, Brucella suis, Campylobacter jejuni, Chlamydia pneumoniae, Chlamydia psitacci, Chlamydia trachomatis, Clostridium botulinum, C. difficile, C. perfringens, C. tetani, Corynebacterium diphtheriae* (i.e., diphtheria), *Enterococcus, Escherichia coli, Haemophilus influenza, Helicobacter pylori, Legionella pneumophila, Leptospira, Listeria monocytogenes, Mycobacterium leprae, M. tuberculosis, Mycoplasma pneumoniae, Neisseria gonorrhea, N. meningitidis, Pseudomonas aeruginosa, Rickettsia recketisii, Salmonella typhi, S. typhimurium, Shigella sonnei, Staphylococcus aureus, S. epidermidis, S. saprophyticus, Streptococcus agalactiae, S. pneumoniae, S. pyogenes, Treponema pallidum, Vibrio cholera, Yersinia pestis, Bordatella pertussis,* and otitis media (e.g., often caused by *Streptococcus pneumoniae, Haemophilus influenzae,* or *Moraxella catarrhalis*), among others described elsewhere herein.

Examples of parasitic infectious diseases include, but are not limited to, Amoebiasis (e.g., *Entemoeba histolytica*), Hookworm Disease (e.g., nematode parasites such as *Necator americanus* and *Ancylostoma duodenale*), Leishmaniasis, Malaria (four species of the protozoan parasite *Plasmodium; P. falciparum, P. vivax, P. ovale,* and *P. malariae*), Schistosomiasis (parasitic *Schistosoma; S. mansoni, S. haematobium,* and *S. japonicum*), *Onchocerca volvulus* (River blindness), *Trypanosoma cruzi* (Chagas disease/American sleeping sickness), and *Dracunculus medinensis*, lymphatic filariasis.

Certain HRS compositions may be useful in the treatment or reduction of endotoxic shock, which often results from exposure to foreign antigens, such as lipopolysaccharide (LPS). Because endotoxic shock can be mediated by TLR signaling, and naturally-occurring endogenous HRS fragments (e.g., SV9) may stimulate TLRs, certain of the binding agents, antisense agents, or RNAi agents provided herein may render a subject more resistant to endotoxic shock by antagonizing or otherwise reducing the endogenous HRS fragment-mediated stimulation of TLR2 and/or TLR4.

Certain HRS compositions may be useful in reducing or antagonizing certain immune activities. For instance, given the role of TLRs in modulating cell migration, such as monocyte migration, HRS compositions that signal through TLRs may also modulate cell migration. In certain aspects, HRS compositions reduce or antagonize CCL1 mediated activities, such as immune cell migration, including monocyte migration. As one example, certain HRS compositions may activate TLRs, such as TLR2 and/or TLR4, which in certain instances leads to cytokine secretion (e.g., MIP1a), and down-regulation in the the levels or activity of related cytokine receptors (e.g., CCL1). Hence, HRS compositions may be employed to modulate immune activity such as cell migration associated with TLRs and cytokine receptors such as CCL1, and thereby treat TLR and/or CCR1-mediated diseases or conditions.

Also included are methods of treating immune diseases. Illustrative immune system diseases, disorders or conditions that may be treated according to the present invention include, but are not limited to, primary immunodeficiencies, immune-mediated thrombocytopenia, Kawasaki syndrome, bone marrow transplant (for example, recent bone marrow transplant in adults or children), chronic B cell lymphocytic leukemia, HIV infection (for example, adult or pediatric HIV infection), chronic inflammatory demyelinating polyneuropathy, post-transfusion purpura, and the like.

Additionally, further diseases, disorders and conditions include Guillain-Barre syndrome, anemia (for example, anemia associated with parvovirus B19, patients with stable multiple myeloma who are at high risk for infection (for example, recurrent infection), autoimmune hemolytic anemia (for example, warm-type autoimmune hemolytic anemia), thrombocytopenia (for example, neonatal thrombocytopenia), and immune-mediated neutropenia), transplantation (for example, cytomegalovirus (CMV)- negative recipients of CMV-positive organs), hypogammaglobulinemia (for example, hypogammaglobulinemic neonates with risk factor for infection or morbidity), epilepsy (for example, intractable epilepsy), systemic vasculitic syndromes, myasthenia gravis (for example, decompensation in myasthenia gravis), dermatomyositis, and polymyositis.

Further autoimmune diseases, disorders and conditions include but are not limited to, autoimmune hemolytic anemia, autoimmune neonatal thrombocytopenia, idiopathic thrombocytopenia purpura, autoimmunocytopenia, hemolytic anemia, antiphospholipid syndrome, dermatitis, allergic encephalomyelitis, myocarditis, relapsing polychondritis, rheumatic heart disease, glomerulonephritis (for example, IgA nephropathy), multiple sclerosis, neuritis, uveitis ophthalmia, polyendocrinopathies, purpura (for example, Henloch-Scoenlein purpura), Reiter's disease, stiff-man syndrome, autoimmune pulmonary inflammation, Guillain-Barre Syndrome, insulin dependent diabetes mellitus, and autoimmune inflammatory eye disease.

Additional autoimmune diseases, disorders or conditions include, but are not limited to, autoimmune thyroiditis; hypothyroidism, including Hashimoto's thyroiditis and thyroiditis characterized, for example, by cell-mediated and humoral thyroid cytotoxicity; SLE (which is often characterized, for example, by circulating and locally generated immune complexes); Goodpasture's syndrome (which is often characterized, for example, by anti-basement membrane antibodies); pemphigus (which is often characterized, for example, by epidermal acantholytic antibodies); receptor autoimmunities such as, for example, Graves' disease (which is often characterized, for example, by antibodies to a thyroid stimulating hormone receptor; myasthenia gravis, which is often characterized, for example, by acetylcholine receptor antibodies); insulin resistance (which is often characterized, for example, by insulin receptor antibodies); autoimmune hemolytic anemia (which is often characterized, for example, by phagocytosis of antibody-sensitized red blood cells); and autoimmune thrombocytopenic purpura (which is often characterized, for example, by phagocytosis of antibody-sensitized platelets).

Further autoimmune diseases, disorders or conditions include, but are not limited to, rheumatoid arthritis (which is often characterized, for example, by immune complexes in joints); scleroderma with anti-collagen antibodies (which is often characterized, for example, by nucleolar and other nuclear antibodies); mixed connective tissue disease, (which is often characterized, for example, by antibodies to extractable nuclear antigens, for example, ribonucleoprotein); polymyositis/dermatomyositis (which is often characterized, for example, by nonhistone anti-nuclear antibodies); pernicious anemia (which is often characterized, for example, by antiparietal cell, antimicrosome, and anti-intrinsic factor antibodies); idiopathic Addison's disease (which is often characterized, for example, by humoral and cell-mediated adrenal cytotoxicity); infertility (which is often characterized, for example, by antispennatozoal antibodies); glomerulonephritis (which is often characterized, for example, by glomerular basement membrane antibodies or immune complexes); by primary glomerulonephritis, by IgA nephropathy; bullous pemphigoid (which is often characterized, for example, by IgG and complement in the basement membrane); Sjogren's syndrome (which is often characterized, for example, by multiple tissue antibodies and/or the specific nonhistone antinuclear antibody (SS-B)); diabetes mellitus (which is often characterized, for example, by cell-mediated and humoral islet cell antibodies); and adrenergic drug resistance, including adrenergic drug resistance with asthma or cystic fibrosis (which is often characterized, for example, by beta-adrenergic receptor antibodies).

Still further autoimmune diseases, disorders or conditions include, but are not limited to chronic active hepatitis (which is often characterized, for example by smooth muscle antibodies); primary biliary cirrhosis (which is often characterized, for example, by anti-mitochondrial antibodies); other endocrine gland failure (which is characterized, for example, by specific tissue antibodies in some cases); vitiligo (which is often characterized, for example, by anti-melanocyte antibodies); vasculitis (which is often characterized, for example, by immunoglobulin and complement in vessel walls and/or low serum complement); post-myocardial infarction conditions (which are often characterized, for example, by anti-myocardial antibodies); cardiotomy syndrome (which is often characterized, for example, by anti-myocardial antibodies); urticaria (which is often characterized, for example, by IgG and IgM antibodies to IgE); atopic dermatitis (which is often characterized, for example, by IgG and IgM antibodies to IgE); asthma (which is often characterized, for example, by IgG and IgM antibodies to IgE); inflammatory myopathies; and other inflammatory, granulomatous, degenerative, and atrophic disorders.

Also included are methods of modulating hematopoiesis and related conditions. Examples of hematopoietic processes that may be modulated by the HRS polypeptides of the invention include, without limitation, the formation of myeloid cells (e.g., erythroid cells, mast cells monocytes/macrophages, myeloid dendritic cells, granulocytes such as basophils, neutrophils, and eosinophils, megakaryocytes, platelets) and lymphoid cells (e.g., natural killer cells, lymphoid dendritic cells, B-cells, and T-cells). Certain specific hematopoietic processes include erythropoiesis, granulopoiesis, lymphopoiesis, megakaryopoiesis, thrombopoiesis, and others. Also included are methods of modulating the trafficking or mobilization of hematopoietic cells, including hematopoietic stem cells, progenitor cells, erythrocytes, granulocytes, lymphocytes, megakaryocytes, and thrombocytes.

The methods of modulating hematopoiesis may be practiced in vivo, in vitro, ex vivo, or in any combination thereof. These methods can be practiced on any biological sample, cell culture, or tissue that contains hematopoietic stem cells, hematopoietic progenitor cells, or other stem or progenitor cells that are capable of differentiating along the hematopoietic lineage (e.g., adipose tissue derived stem cells). For in vitro and ex vivo methods, stem cells and progenitor cells, whether of hematopoietic origin or otherwise, can be isolated and/or identified according to the techniques and characteristics described herein and known in the art.

In still other embodiments, the HRS compositions of the invention may be used to modulate angiogenesis, e.g., via modulation of endothelial cell proliferation and/or signaling. Endothelial cell proliferation and/or cell signaling may be monitored using an appropriate cell line (e.g., Human microvascular endothelial lung cells (HMVEC-L) and Human umbilical vein endothelial cells (HUVEC)), and using an appropriate assay (e.g., endothelial cell migration assays, endothelial cell proliferation assays, tube-forming assays, matrigel plug assays, etc.), many of which are known and available in the art.

Therefore, in related embodiments, the compositions of the invention may be employed in the treatment of essentially any cell or tissue or subject that would benefit from modulation of angiogenesis. For example, in some embodiments, a cell or tissue or subject experiencing or susceptible to angiogenesis (e.g., an angiogenic condition) may be contacted with a suitable composition of the invention to inhibit an angiogenic condition. In other embodiments, a cell or tissue experiencing or susceptible to insufficient angiogenesis (e.g., an angiostatic condition) may be contacted with an appropriate composition of the invention in order to interfere with angiostatic activity and/or promote angiogenesis.

Illustrative examples of angiogenic conditions include, but are not limited to, age-related macular degeneration (AMD), cancer (both solid and hematologic), developmental abnormalities (organogenesis), diabetic blindness, endometriosis, ocular neovascularization, psoriasis, rheumatoid arthritis (RA), and skin discolorations (e.g., hemangioma, nevus flammeus or nevus simplex). Examples of anti-angiogenic conditions include, but are not limited to, cardiovascular disease, restenosis, tissue damage after reperfusion of ischemic tissue or cardiac failure, chronic inflammation and wound healing.

In other embodiments, the HRS compositions of the invention may be used to modulate cellular proliferation and/or survival and, accordingly, for treating or preventing diseases, disorders or conditions characterized by abnormalities in cellular proliferation and/or survival. For example, in certain embodiments, the HRS compositions may be used to modulate apoptosis and/or to treat diseases or conditions associated with abnormal apoptosis. Apoptosis is the term used to describe the cell signaling cascade known as programmed cell death. Various therapeutic indications exist for molecules that induce apoptosis (e.g. cancer), as well as those that inhibit apoptosis (i.e. stroke, myocardial infarction, sepsis, etc.). Apoptosis can be monitored by any of a number of available techniques known and available in the art including, for example, assays that measure fragmentation of DNA, alterations in membrane asymmetry, activation of apoptotic caspases and/or release of cytochrome C and AIF.

Illustrative diseases associated with increased cell survival, or the inhibition of apoptosis include, but are not limited to, cancers (such as follicular lymphomas, carcinomas, and hormone-dependent tumors, including, but not limited to colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, breast cancer, prostate cancer, Kaposi's sarcoma and ovarian cancer); autoimmune disorders (such as, multiple sclerosis, Sjogren's syndrome, Graves' disease, Hashimoto's thyroiditis, autoimmune diabetes, biliary cirrhosis, Behcet's disease, Crohn's disease, polymyositis, systemic lupus erythematosus and immune-related glomerulonephritis, autoimmune gastritis, autoimmune thrombocytopenic purpura, and rheumatoid arthritis) and viral infections (such as herpes viruses, pox viruses and adenoviruses), inflammation, graft vs. host disease (acute and/or chronic), acute graft rejection, and chronic graft rejection.

Further illustrative diseases or conditions associated with increased cell survival include, but are not limited to, progression and/or metastases of malignancies and related disorders such as leukemia (including acute leukemias (for example, acute lymphocytic leukemia, acute myelocytic leukemia, including myeloblastic, promyelocytic, myelomonocytic, monocytic, and erythroleukemia)) and chronic leukemias (for example, chronic myelocytic (granulocytic) leukemia and chronic lymphocytic leukemia), myelodysplastic syndrome polycythemia vera, lymphomas (for example, Hodgkin's disease and non-Hodgkin's disease), multiple myeloma, Waldenstrom's macroglobulinemia, heavy chain diseases, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Illustrative diseases associated with increased apoptosis include, but are not limited to, AIDS (such as HIV-induced nephropathy and HIV encephalitis), neurodegenerative disorders (such as Alzheimer's disease, Parkinson's disease, amyotrophic lateral sclerosis, retinitis pigmentosa, cerebellar degeneration and brain tumor or prior associated disease), autoimmune disorders such as multiple sclerosis, Sjogren's syndrome, Graves' disease, Hashimoto's thyroiditis, autoimmune diabetes, biliary cirrhosis, Behcet's disease, Crohn's disease, polymyositis, systemic lupus erythematosus, immune-related glomerulonephritis, autoimmune gastritis, thrombocytopenic purpura, and rheumatoid arthritis, myelodysplastic syndromes (such as aplastic anemia), graft vs. host disease (acute and/or chronic), ischemic injury (such as that caused by myocardial infarction, stroke and reperfusion injury), liver injury or disease (for example, hepatitis related liver injury, cirrhosis, ischemia/reperfusion injury, cholestosis (bile duct injury) and liver cancer), toxin-induced liver disease (such as that caused by alcohol), septic shock, ulcerative colitis, cachexia, and anorexia.

In still further embodiments, the compositions of the invention may be used in the treatment of neuronal/neurological diseases or disorders, illustrative examples of which include Parkinson's disease, Alzheimer's disease, Pick's disease, Creutzfeldt-Jacob disease, Huntington's chorea, alternating hem iplegia, amyotrophic lateral sclerosis, ataxia, cerebral palsy, chronic fatigue syndrome, chronic pain syndromes, congenital neurological anomalies, cranial nerve diseases, delirium, dementia, demyelinating diseases, dysautonomia, epilepsy, headaches, Huntington's disease, hydrocephalus, meningitis, movement disorders, muscle diseases, nervous system neoplasms, neurocutaneous syndromes, neurodegenerative diseases, neurotoxicity syndromes, ocular motility disorders, peripheral nervous system disorders, pituitary disorders, porencephaly, Rett syndrome, sleep disorders, spinal cord disorders, stroke, sydenham's chorea, tourette syndrome, nervous system trauma and injuries, etc. In certain embodiments, the neurological condition is associated with 6-hydroxydopamine (6-OHDA)-induced neuron death, a neurotoxin that is thought to be involved in pathogenesis of certain neurological conditions such as Parkinson's disease, or a related mechanism.

Furthermore, additional embodiments relate to the use of the compositions of the invention in the treatment of metabolic disorders such as adrenoleukodystrophy, Krabbe's disease (globoid cell leukodystrophy), metachromatic leukodystrophy, Alexander's disease, Canavan's disease (spongiform leukodystrophy), Pelizaeus-Merzbacher disease, Cockayne's syndrome, Hurler's disease, Lowe's syndrome, Leigh's disease, Wilson's disease, Hallervorden-Spatz disease, Tay-Sachs disease, etc. The utility of the compositions of the invention in modulating metabolic processes may be monitored using any of a variety of techniques known and available in the art including, for example, assays which measure adipocyte lipogenesis or adipocyte lipolysis.

In more specific embodiments of the invention, the HRS compositions of the invention may be used to modulate cellular signaling, for example, via cell signaling proteins. Cell signaling may be monitored using any of a number of well known assays. For example, the induction of general cell signaling events can be monitored through altered phosphorylation patterns of a variety of target proteins. Detection of cell signaling activities in response to treatment of cells with HRS polypeptides therefore serves as an indicator of distinct biological effects. Target proteins used for this assay may be selected so as to encompass key components of major cellular signaling cascades, thereby providing a broad picture of the cell signaling landscape and its therapeutic relevance. Generally, such assays involve cell treatment with HRS polypeptides followed by immunodetection with antibodies that specifically detect the phosphorylated (activated) forms of the target proteins.

Illustrative target proteins useful for monitoring therapeutically relevant cell signaling events may include, but are not limited to: p38 MAPK (mitogen-activated protein kinase; activated by cellular stress and inflammatory cytokines; involved in cell differentiation and apoptosis); SAPK/JNK (stress-activated protein kinase/Jun-amino-terminal kinase; activated by cellular stresses and inflammatory cytokines); Erk1/2, p44/42 MAPK (mitogen-activated protein kinase Erk1 and Erk2; activated by wide variety of extracellular signals; involved in regulation of cell growth and differentiation); and Akt (activated by insulin and various growth or survival factors; involved in inhibition of apoptosis, regulation of glycogen synthesis, cell cycle regulation and cell growth). General phosphorylation of tyrosine residues may also be monitored as a general indicator of changes in cell signaling mediated by phosphorylation.

Of course, it will be recognized that other classes of proteins, such as cell adhesion molecules (e.g., cadherins, integrins, claudins, catenins, selectins, etc.) and/or ion channel proteins may also be assayed for monitoring cellular events or activities modulated by the compositions of the invention.

In other specific embodiments of the invention, the HRS compositions of the invention may be used to modulate cytokine production by cells, for example, by leukocytes. Cytokine production may be monitored using any of a number of assays known in the art (i.e., RT-PCR, ELISA, ELISpot, flow cytometry, etc.). Generally, such assays involve cell treatment with HRS polypeptides followed by detection of cytokine mRNA or polypeptides to measure changes in cytokine production. Detection of increases and/or decreases in cytokine production in response to treatment of cells with HRS polypeptides therefore serves as an indicator of distinct biological effects. HRS polypeptides of the invention may induce, enhance, and/or inhibit an immune or inflammatory response by modulating cytokine production. For example, HRS polypeptides and compositions of the invention may be used to alter a cytokine profile (i.e., type 1 vs. type 2) in a subject. Illustrative cytokines that may measured for monitoring biological effects of the HRS compositions include, but are not limited IL-1α, IL-1β, IL-2, IL-3, IL-4, IL-5, IL-6, IL-7, IL-10, IL-12, IL-15, IL-18, IL-23 TGF-β, TNF-α, IFN-α, IFN-β, IFN-γ, RANTES, MIP-1α, MIP-1β, MCP-1, GM-CSF, G-CSF, etc.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims. The following examples are provided by way of illustration only and not by way of limitation. Those of skill in the art will readily recognize a variety of noncritical parameters that could be changed or modified to yield essentially similar results.

EXAMPLES

Example 1

Figure 1B:
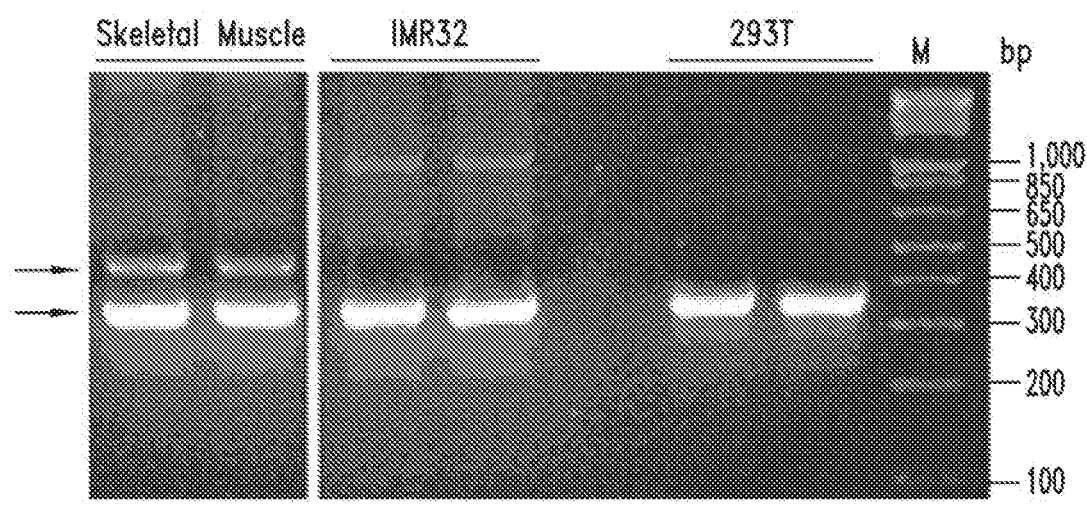

Identification of Alternative Splice Variant, HRS-SV9, of the Human Histidyl-tRNA Synthetase (HRS) Gene An alternative splice variant of the HRS gene, referred to as HRS-SV9, was identified by PCR as follows. A pair of primers, one covering the boundary region of 5'-untranslated region and Exon 1 (HRS-BPF: AGTGGACAGCCGG-GATGGCAGAGC (SEQ ID NO: 1)) and the other near the 3'-end of Exon 4 (HRS-P1R: CAGGAAGTCGCCTATCT-GAAG (SEQ ID NO: 2)), were used to search for an Intron 2 retention splicing event previously reported by the University of California Santa Cruz EST database (EST #BP267368). PCR reaction products using cDNA as template gave rise to one distinct band (FIG. 1B, upper arrow) larger than the reference band (FIG. 1B, lower arrow), which is the fragment amplified from the full-length HRS gene (NM_002109.3; SEQ ID NO: 3). This larger band was detected in a human skeletal muscle cDNA library, but not in cDNA libraries from HEK293T or IMR32 cells, indicating tissue specificity of this splice variant. This band was excised, and the DNA fragment was extracted with a gel purification kit for sequencing.

Figure 3A:
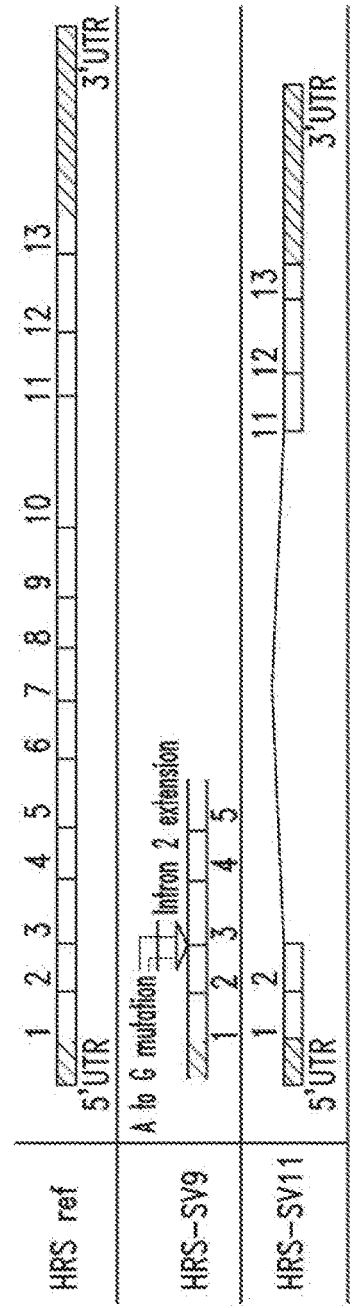
Figure 3B:
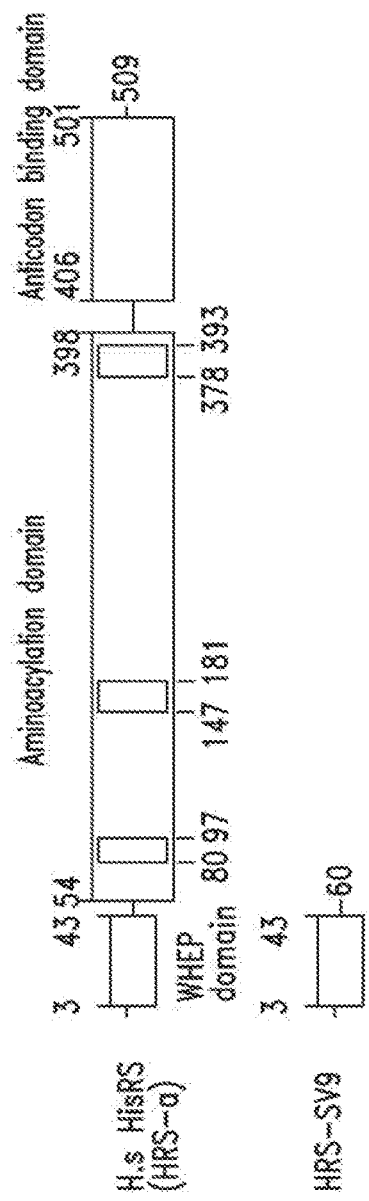
Figure 3B:

DNA sequencing confirmed an insertion from Intron 2, as previously reported, however there was no evidence of the reported T>C mutation in Exon 2, making this as a distinct alternative splice variant of HRS gene (FIG. 3A). The sequence inserted from Intron 2 introduces a stop codon immediately after Exon 2, such that the encoded protein sequence has only the first 60 amino acids of the full length HRS protein (FIG. 3B). FIG. 3C shows the nucleic acid coding sequence (SEQ ID NO: 5) and encoded protein sequence (SEQ ID NO: 6) for the HRS-SV9 splice variant.

Example 2

Figure 2A:
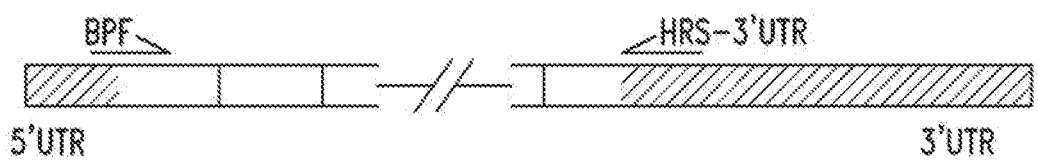
FIGS. 2A-C show the identification of the HRS-SV11 splice variant from an IMR32 cell library and in samples from the human brain.
Figure 2B:
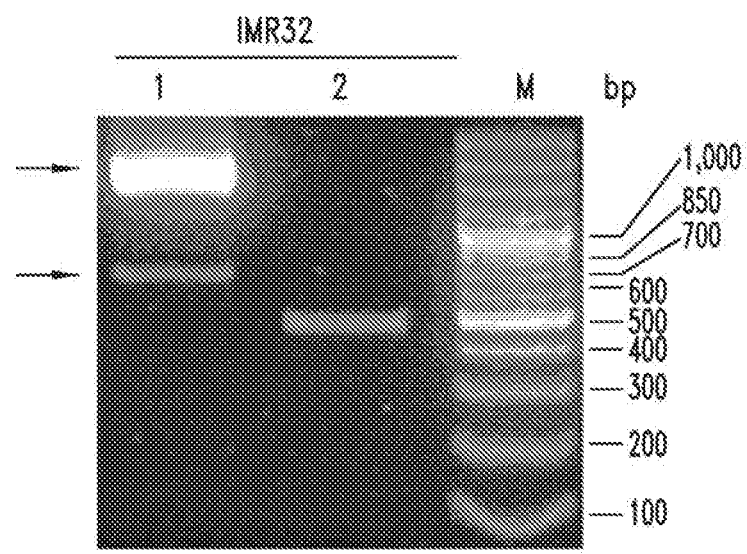

Identification of Alternative Splice Variant, HRS-SV11, of the Human Histidyl-tRNA Synthetase (Hrs) Gene In this example, another alternative splice variant of the HRS gene, referred to as HRS-SV11, was also identified. A pair of primers, one covering the boundary of the 3'-end of 5'-UTR and 5'-end of Exon 1 (HRS-BPF:

AGTGGACAGCCGGGATGGCAGAGC (SEQ ID NO: 1)) and the other covering residues in the 5'-end of 3'-UTR (HRS-3'-UTR: ATAGTGCCAGTCCCACTTCC (SEQ ID NO: 7)), was used. A distinct band (FIG. 2B, lower arrow) smaller than the reference band (FIG. 2B, upper arrow) was observed following PCR amplification of cDNA. The band was excised, gel-purified and sequenced. DNA sequencing confirmed that this is a splice variant of the HRS gene containing a deletion from Exon 3 to Exon 10 (FIG. 3A). This deletion causes no frame-shifting. Thus, at the protein level, HRS-SV11 comprises the N-terminal WHEP domain and the C-terminal anticodon domain of the reference HRS protein, but the aminoacylation domain is missing (FIG. 3B).

Figure 2C:
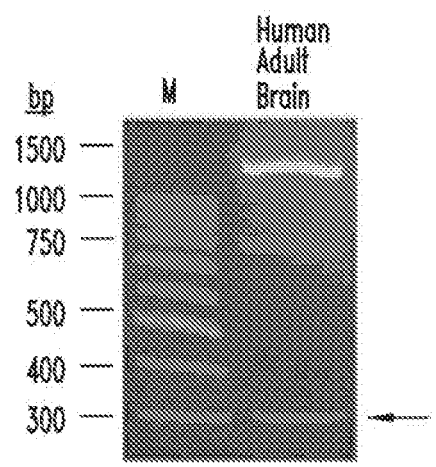

FIG. 3D shows the nucleic acid coding sequence (SEQ ID NO: 8) and encoded protein sequence (SEQ ID NO: 9) for the HRS-SV11 splice variant. As shown in FIG. 2C, this transcript was found in total cDNA of human adult brain, lung, skeletal muscle and THP-1, Jurkat cells.

Example 3

Splice Variants HRS-SV9 and HRS-SV11 May be Naturally Occurring

Figure 4A:
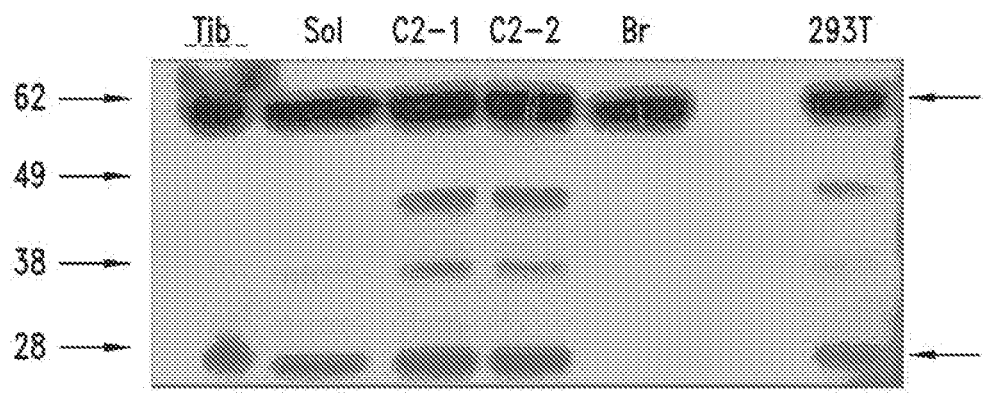
FIGS. 4A-B show immunoblot results using anti-HRS antibodies in rat tibialis muscle (Tib), soleus muscle (Sol), C2C12 myotubes (C2), adult rat brain (Br) and HEK293T cells (293T).
Figure 4B:
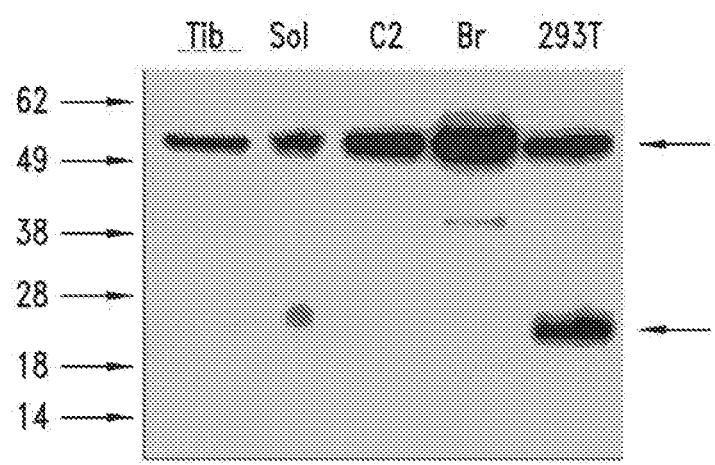

To test the natural existence of these splice variants at the protein level, total cell extract were immunoblotted with anti-HRS antibodies. Two commercial antibodies, a monoclonal antibody with an epitope from amino acids 1-97 (Novus Biologicals) and a polyclonal antibody with an epitope in the 50-200 amino acids near the C-terminus (Abcam), were tested with a number of cell lines, including HEK293T, C2C12, and muscle tissues from adult rats, including tibialis muscles (representing fast muscle) and soleus muscles (representing slow muscle). Both the N- and C-terminal antibodies detected a band (lower arrows in FIGS. 4A and 4B) in HEK293T, adult rat tibialis and soleus muscle having a size consistent with the predicted size of the HRS-SV11 splice variant polypeptide.

Immunoprecipitation with the N-terminal antibody detected a band in differentiated C2C12 myotubes (lower arrow in FIG. 5A), having a size consistent with the predicted size of the HRS-SV9 splice variant polypeptide. Bands were not detected in HEK293T cells or C2C12 differentiated myoblasts.

Figures 5A, 5B, 5C:
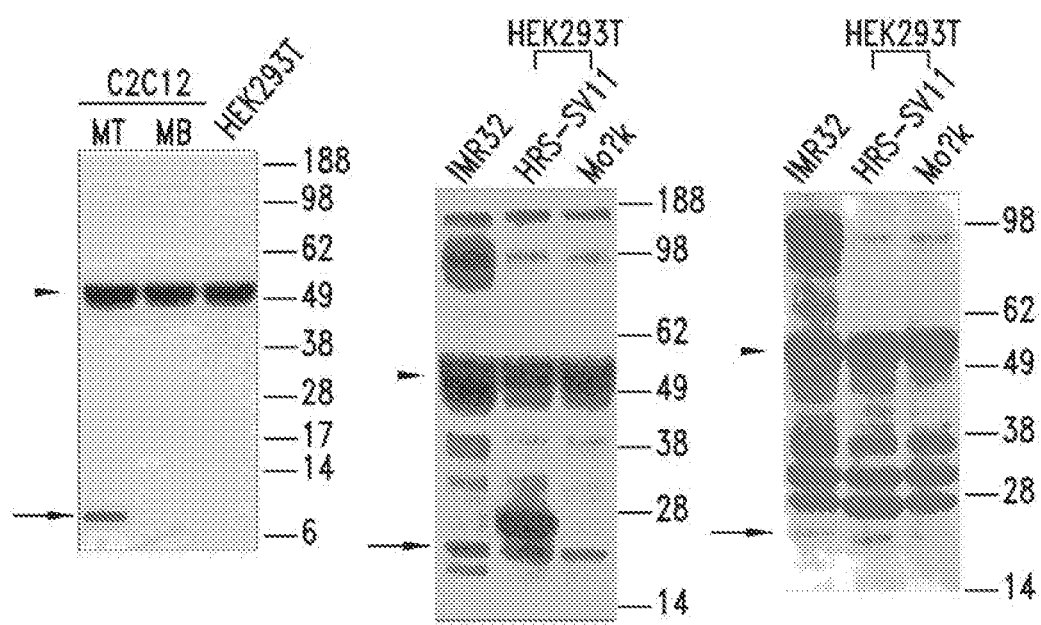
FIGS. 5A-C show results of immunoprecipitation experiments with an N-terminal HRS monoclonal antibody (raised against amino acids 1-97 of wild-type human HRS protein).

Total cell lysate of HEK293T cells that over-express myc-tagged HRS-SV11 was also used as a reference for endogenous HRS-SV11 protein, which should be slightly smaller than myc-tagged HRS-SV11. As shown in FIGS. 5B and 5C, a band running around 20 kDa but slightly smaller than myc-tagged HRS-SV11 was detected in IMR32 cells by both antibodies (lower arrows in B and C), suggesting the presence endogenous HRS-SV11.

Example 4

Secretion of Splice Variants HRS-SV9 and HRS-SV11 from HEK293T Cells when Overexpressed In this example, HRS-SV9 and HRS-SV11 were forcefully expressed in HEK293T cells and tested to determine whether they were secreted from the cells.

For plasmid construction, the wild type HRS, HRS-SV9 and HRS-SV11 coding sequences were cloned into pCI-neo-myc-myc-C vector (Promega, Madison, Wis.) through EcoRI/XhoI, respectively. For secretion assays, HEK293T cells were transfected when they reach 60-70% confluency. 1 μg DNA was mixed with 125 μl Opti-MEM. 4 μl lipofectamine 2000 was mixed with 125 μl Opti-MEM. After 5 minutes, DNA-Opti-MEM complex was added to lipofectamine 2000-Opti-MEM complex with gentle tapping several times. The mixture was incubated 20 minutes at room temperature and added drop-wise on top of cells. After gentle swirling, cells were returned to the incubator. Culture medium was refreshed after 6-7 hours. 24 hours after transfection, medium was changed to Dulbecco's Modified Eagle Medium (DMEM) without serum. Both medium and total cell extract were harvested after another 6 hours of incubation. Proteins in media were precipitated with 20% TCA (trichloroacetic acid). Both media and total cell extracts were resolved on NuPAGE Novex 4-12% Bis-Tris Gel (Invitrogen) and immunoblotted with the N-terminal HRS and tubulin antibodies (Invitrogen).

Figure 6A:
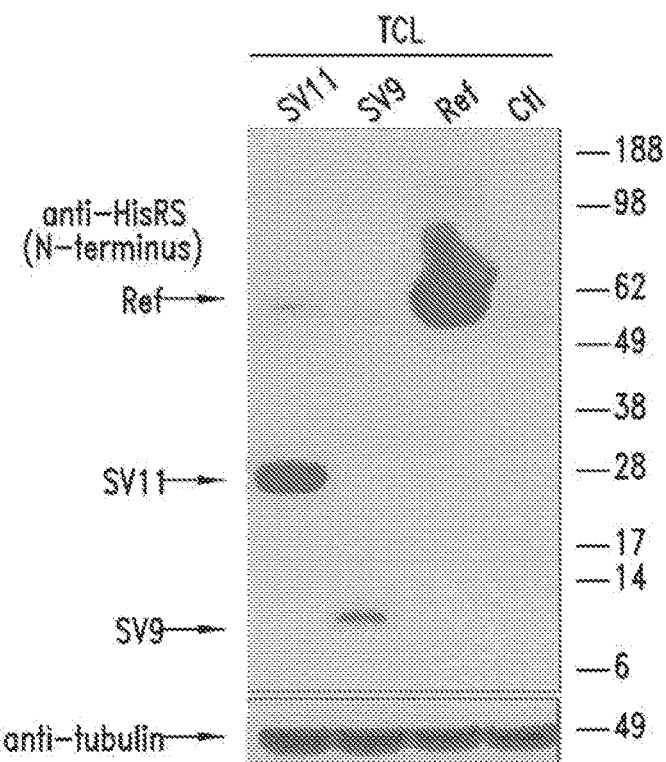
FIGS. 6A-C demonstrate the secretion of HRS, HRS-SV9 and HRS-SV11 following recombinant production in HEK293T cells. Wild type, full length HRS (HRS-Ref), HRS-SV9 and HRS-SV11 were forcefully expressed in HEK293T cells.
Figure 6C:
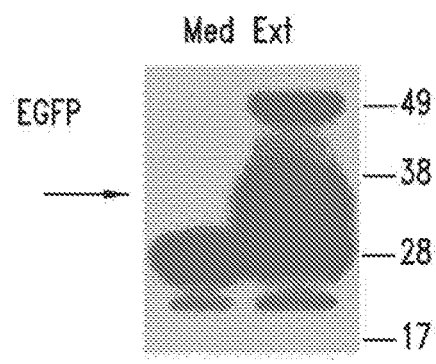
Figure 6B:
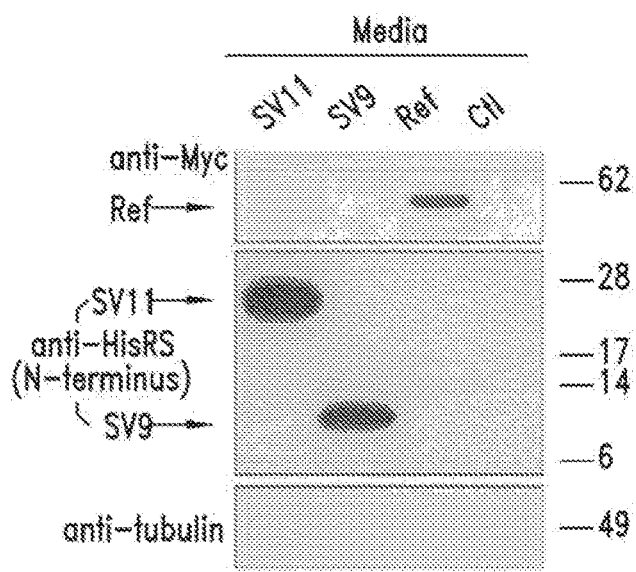

Using this approach, HRS-SV9 and HRS-SV11, as well as full-length HRS, were detected in media fractions, demonstrating they were secreted from the HEK293T cells (FIG. 6). In contrast, enhanced green fluorescent protein (EGFP) was not secreted (see FIG. 6C). As shown in FIGS. 6A-B, tubulin was used as leaky control; tubulin is present in the total cell lysate fraction, but is absent in medium fraction, demonstrating no leakiness in this experiment.

Example 5

Splice Variants HRS-SV9 and HRS-SV11 Increase IL-2 Secretion in Activated T-Cells When antigen is presented by antigen presenting cells (APC), the earliest detectable response of T cell activation is the secretion of cytokines, such as IL-2. Through autocrine secretion, IL-2 triggers T cells proliferation, thereby generating cells required to eliminate antigen. Thus, regulators of IL-2 secretion serve as immunomodulators for T lymphocyte-mediated immune responses.

Figure 7:
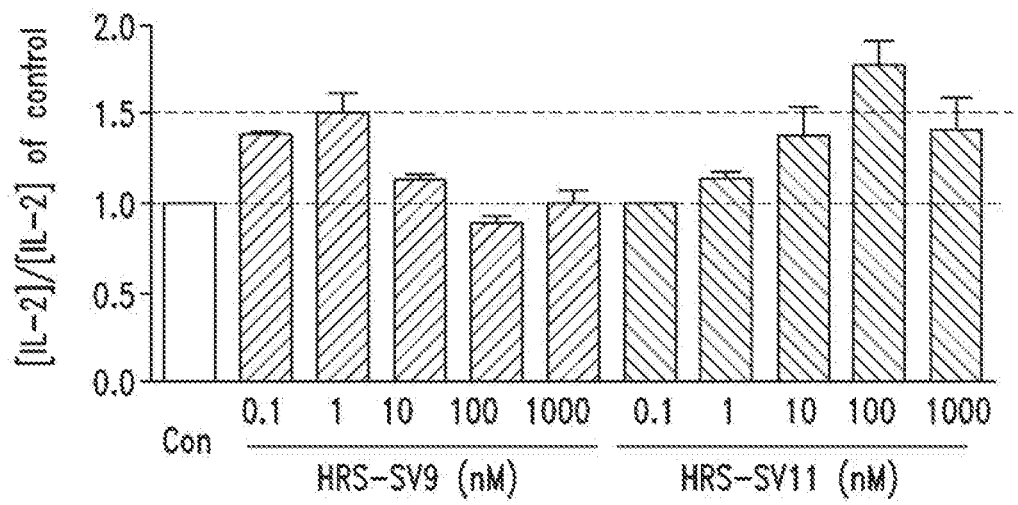
FIG. 7 shows that recombinant HRS-SV9 and HRS-SV11 splice variant polypeptides enhance IL-2 secretion in activated Jurkat T cells. Cells were treated with PMA (25 ng/ml) plus ionomycin (250 ng/ml) with or without HRS-SV9 or HRS-SV11, and media was analyzed 48 hours later by ELISA.

Leukemia Jurkat T cells (ATCC No: TIB-152) are widely used for T cell activation research, using IL-2 expression and release as an indication of activation. For T cell activation, Jurkat T cells were stimulated by phorbol esters (PMA) and ionomycin (IOM). IL-2 secretion into media was evaluated by ELISA. As expected, PMA and ionomycin stimulated Jurkat T cells to release IL-2 in a dose dependent manner. As shown in FIG. 7, HRS-SV9 and HRS-SV11, when co-applied with PMA and IOM significantly increased IL-2 secretion. Thus, both HRS-SV9 and HRS-SV11 exhibited unexpected immunomodulatory activity.

Example 6

Splice Variant HRS-SV9 Stimulates TNF-α Secretion in PBMCs

Peripheral blood mononuclear cells (PBMCs) were isolated from human blood. The cells were resuspended in RPMI media with 10% FBS to $1 \times 10^6$ cells/mL. One million cells were treated for 24 hours with HRS-SV9 at 6.25, 12.5, 25, 50, 100, and 250 nM. PBMCs were also treated with Lipopolysaccharide (LPS) at 1 EU/mL, PBS, or 100 nM Negative Control Protein 1 or 2. After 24 hours, cell supernatant was collected by centrifugation at 2000×g for 10 min and evaluated in a TNF-α ELISA assay (R&D Systems; Cat. DTA00C).

Figure 8:
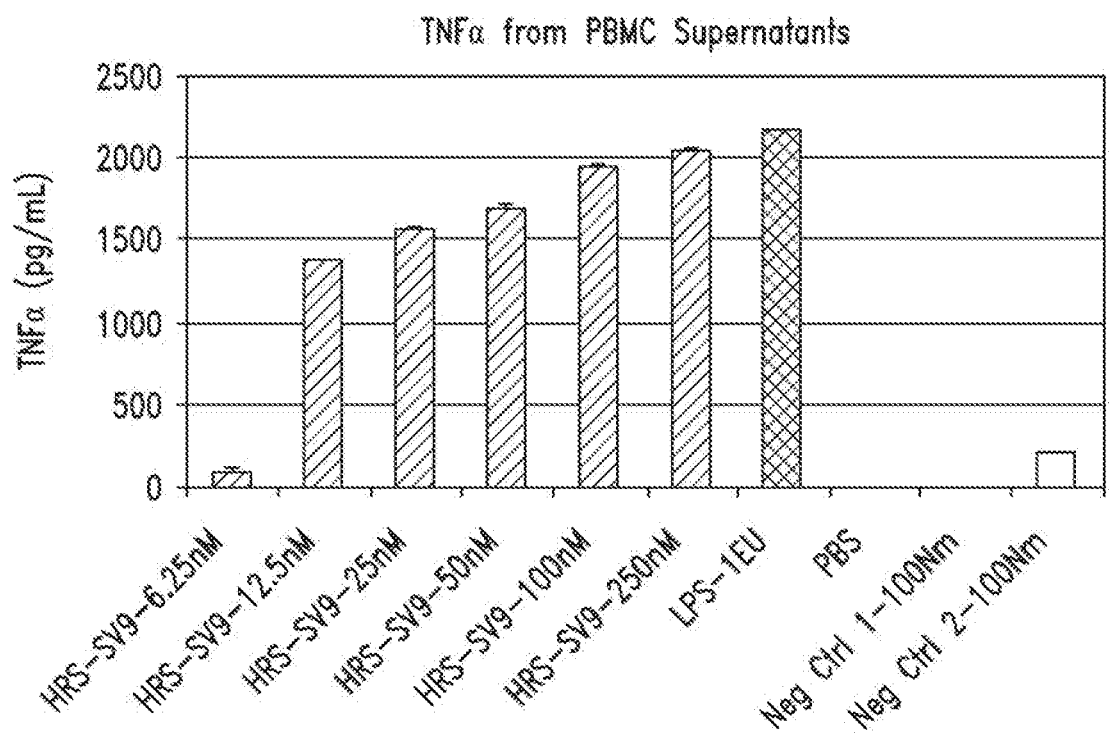
FIG. 8 shows that HRS-SV9 stimulated PBMCs to release TNFα into the culture supernatant. LPS was used as a positive control.
Figure 10B:
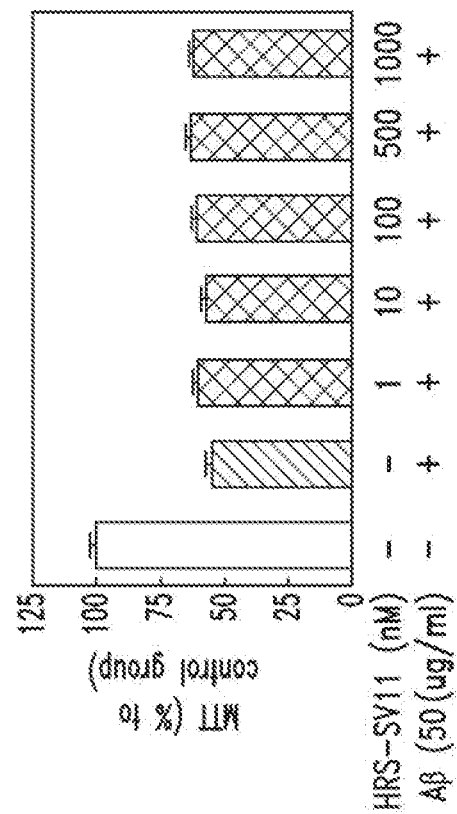
FIGS. 10A-F show that HRS-SV11 did not protect neurons from amyloid beta, monosodium glutamate (MSG), and MPP+-induced toxicity.
Figure 10A:
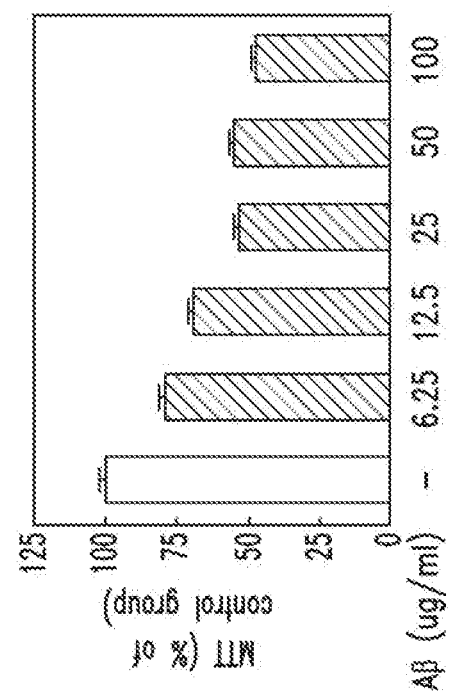
Figure 10D:
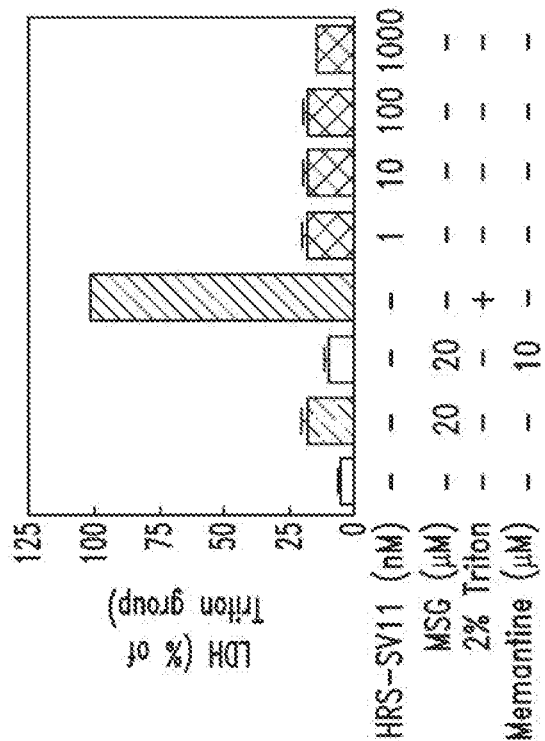
Figure 10C:
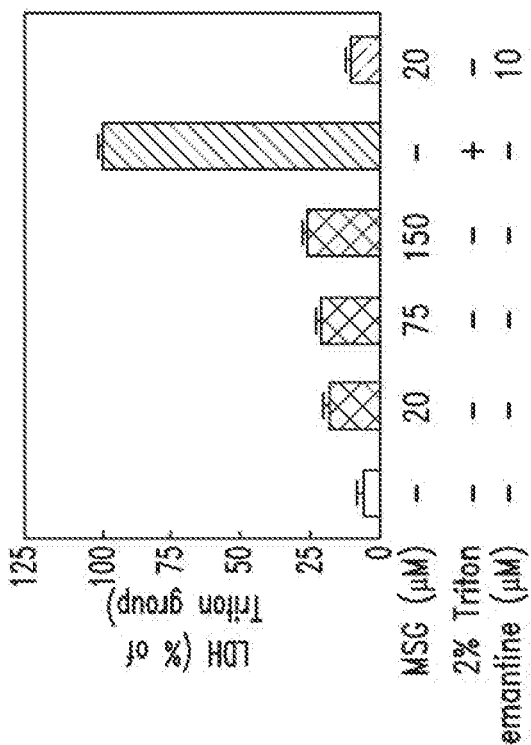
Figure 10F:
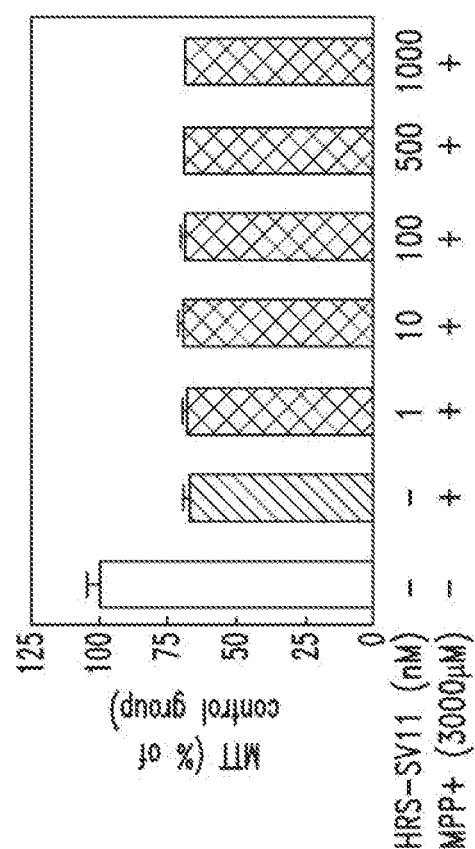
Figure 10E:
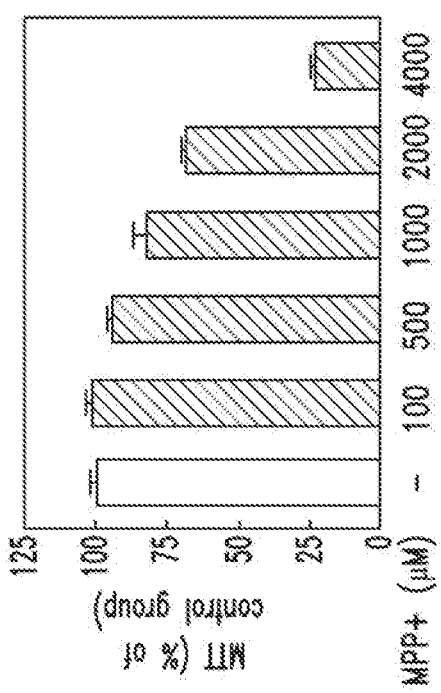

As shown in FIG. 8, HRS-SV9 stimulated PBMCs to secrete TNF-α in a dose dependent manner. In contrast, cells treated with PBS or negative control proteins secreted minimal or no TNF-α (PBS, Neg. Ctrl. 1 and Neg. Ctrl. 2). LPS, a known inducer of TNF-α secretion, gave rise to a positive signal at 1 EU/ml. Although a minimal amount of LPS was present in the HRS-SV9 protein (~0.11 EU/mL at 250 nM), the TNF-α signal observed for HRS-SV9 is above that which may be attributed to LPS. The results of this example demonstrate that HRS-SV9 acts as a modulator of TNF-α secretion.

Example 7

HRS-SV11 Protects Rat Cortical Neurons and PC12 Cells from 6-OHDA-Induced Neuron Cell Death Since HRS-SV11 transcript was identified from a neuronal cell line, this protein was tested in neuroprotection assays by using cultured primary rat cortical neurons and PC12 cells. The assays used were: (1) 6-hydroxydopamine (6-OHDA)-induced neuron death, a neurotoxin that is thought to be involved in pathogenesis of Parkinson's disease (PD); (2) Beta-amyloid (Aß)-induced neuron death (using the $Aß_{1-42}$ form), which reproduces Alzheimer's disease; (3) L-glutamic acid-induced neuron death, which is observed in many neurological diseases such as stroke; and (4) MPP+-induced PC12 cell death. These experimental models have been extensively studied and are considered to be physiologically relevant to human neurological diseases.

Preparation of recombinant protein. HRS-SV11 was cloned into pET20b vector (Novagen) at EcoRV/NotI sites without the stop codon. A polyhistidine tag (6×His) from the pET2ob vector was added to the C-terminus of HRS-SV11 protein, allowing purification with nickel-NTA beads. *E. coli* Rosetta strain (Novagen) was transformed with the pET20b-HRS-SV11 plasmid and grew at 37° C. with vigorous shaking until $OD_{600}$ reached 0.6-0.8. 200 μM IPTG was added to induce protein expression. Bacteria was grown at 16° C. overnight.

The bacteria were then pelleted, resuspended in 50 ml 1×Ni-NTA buffer (50 mM Tris, 300 mM NaCl, and 25 mM imidazole, pH8.0) with 1 tablet of Complete EDTA-free protease inhibitor (Roche) and 300 mg lysozyme (Sigma), and placed on rotating wheel at 4° C. for 30 min. The lysate was sonicated with 6×10" pulses with 5" brakes (increase amplitude from 25% to 50% to 75% for 3 cycles). Then lysate was spin down at 14,000 rpm for 45 min at 4° C. Supernatant was collected and incubate with 1 ml Ni-NTA resin slurry for 10-15 min in a 50 ml column. After incubation, the protein-beads mixture was washed extensively with 1×Ni-NTA buffer (50 mM Tris, 300 mM NaCl, 25 mM Imidazole, pH8.0) supplemented with 0.1% Triton X-114 to remove endotoxin from bacteria. Upon finishing wash, proteins were eluted in 10 ml (1×) NI-NTA elution buffer (50 mM Tris, 300 mM NaCl, 300 mM Imidazole, pH8.0). Protein was dialyzed in 10 kDa cutoff slide-a-lyzer (Pierce) against 2×PBS for three times, then concentrated with a 10 kDa cutoff Amicon centricon (Fisher). Concentrated protein was stored in 50% glycerol and 2 mM DTT at −20° C. HRS-SV14 and wild type HRS were cloned into pET21a vector and purified in the same way as HRS-SV11.

Cell Culture and Treatment.

PC12 cells were maintained in Dulbecco's Modified Eagle's Medium (DMEM) (Invitrogen) supplemented with 8% horse serum, 8% fetal bovine serum, 30 IU/ml penicillin and 30 μg/ml streptomycin at 37° C., 5% $CO_2$. For neuroprotection assays, PC12 cells were seeded into 24-well plates at $1.25*10^5$ cells/well and used one day after seeding.

Primary rat cortical neurons were isolated from rat embryos at embryonic day 18 (E18) and cultured as described previously (Brewer et al., 1995) with some modifications. Briefly, the cortex was dissected out in Hank's Balanced Salt Solution (HBSS) supplemented with 1 mM sodium pyruvate and 10 mM HEPES (pH 7.4) without $Ca^{2+}$ and $Mg^{2+}$ (Gibco). After being trypsinized for 15 min at 37° C., treated cortex were washed with plating medium (DMEM with 10% horse serum, supplemented with 0.5 mM GlutaMAX, 100 U/ml penicillin and 100 μg/ml streptomycin), and triturated for several times. The cells were allowed to settle down for 3 min, and then pelleted by centrifugation at 1,200 rpm for 5 minutes. The cell pellet was suspended in 1 ml plating medium and counted. $1.5×10^5$ cells were seeded in poly-L-lysine (0.1 mg/ml)-coated 24-well culture plates and maintained at 37° C., 5% $CO_2$. After 4 hrs, plating medium was replaced by culture medium (Neurobasal medium, supplemented with 0.5 mM GlutaMAX and (1×) B27 supplement). Half medium was refreshed once a week. Experiments were performed at 9 day in vitro (DIV 9) unless mentioned otherwise. One day before experiments, half medium was refreshed.

In drug treatment studies, drugs were diluted in culture medium (but 6-OHDA was diluted in $H_2O$), and then applied to cells. For monosodium glutamate (MSG)-induced neurotoxicity, neurons were exposed to MSG for 20 min, and washed once with culture medium and kept in fresh culture medium. Memantine was added at the same time with MSG. For beta-amyloid-induced toxicity, $Aß_{1-42}$ was incubated at 37° C. for a day to form aggregates, then was added to cells. For hydrogen peroxide-induced toxicity, a tablet of $H_2O_2$ was dissolved in 12.5 ml $H_2O$ to make a stock, and then added to cells.

The $EC_{50}$ of each neurotoxin was determined and used in the following experiments. Neuron viability was measured by MTT and LDH assays. The MTT assay is based on utilization of mitochondrial dehydrogenases of viable cells, which cleave the tetrazolium ring of the MTT and yield purple MTT formazan crystals, while the LDH assay measures the released LDH in medium due to disruption of membrane integrity. For the MTT assay, MTT was added into the medium at a final concentration of 0.5 mg/ml and incubated with cells for 2 hrs at 37° C., 5% $CO_2$. The mitochondrial dehydrogenase cleaves the MTT tetrazolium ring and yields purple formazan crystals. After incubation, medium was aspirated and 500 μl dimethylsulphoxide (DMSO) was added to solubilize the formazan crystals. The microplate was gently shaken and incubated at 37° C. for 5 min. Then, 100 μl solution was taken and filled in a 96-well microplate, and the absorbance was read at 570 nm (630 nm as reference) by spectrophotometer (BMG Labtech, Offenburg, Germany). The relative absorbance (OD570-OD630) was used as an indicator of cell viability.

For the LDH assay, released LDH in the medium was measured by LDH assay kit (Roche) following the product's instruction. Medium was collected and spun down. The supernatant was saved and 100 μl was filled in a well of a 96-well microplate (MP). 100 μl of freshly prepared reaction mixture was added to each well, and incubated with medium for 15 min at room temperature. The microplate was kept from light after adding the reaction mixture. The absorbance of the samples at 492 nm was measured after 15 min by spectrophotometer (BMG Labtech, Offenburg, Germany). 200 μl of the assay medium was used as a background control. 2% Triton X-100 was used as a positive control since it permeabilizes all cell membrane and releases the maximal amount of LDH.

Among the three neuroprotection assays, it was found that HRS-SV11 protected cortical neurons from 6-OHDA-induced neuron death in a dose-dependent manner when these neurons were pre-treated with HRS-SV11 for 24 hr (FIG. 9A), but had little to no effect on Aß-, L-glutamic acid-, and MPP+-induced neuron death (FIG. 10).

HRS-SV11 was also tested in a 6-OHDA-induced PC12 cell death model, since this model is also relevant to PD and has been well characterized. Similar protection was observed against 6-OHDA after pre-treating PC12 cells with HRS-SV11 for 24 hr (FIGS. 9B-C). In addition to 24 hr pre-treatment, HRS-SV11 also exerted neuroprotection with even 30 min pre-treatment (FIG. 5D), suggesting new protein synthesis may not be necessary for HRS-SV11's neuroprotection.

Example 8

HRS-SV11 Protect Neurons Through a Non-Extracellular Mechanism

The exact mechanism of neurotoxicity of 6-OHDA is not clearly understood, but there's more evidence favor an extracellular mechanism, rather than an intracellular one (see Blum et al., 2000; Izumi et al., 2005; Hanrott et al., 2006). 6-OHDA, in the extracellular space, is auto-oxidized into p-quinone and reactive oxygen species, such as hydrogen peroxide ($H_2O_2$). To examine whether HRS-SV11, like other antioxidants, protects PC12 cells through reducing $H_2O_2$ and p-quinone in the extracellular space, a cell-free system was used to measure accumulation of p-quinone in the presence or absence of HRS-SV11 by taking advantage of a property of p-quinone that p-quinone has a unique absorbance at 490 nm.

Figure 11A:
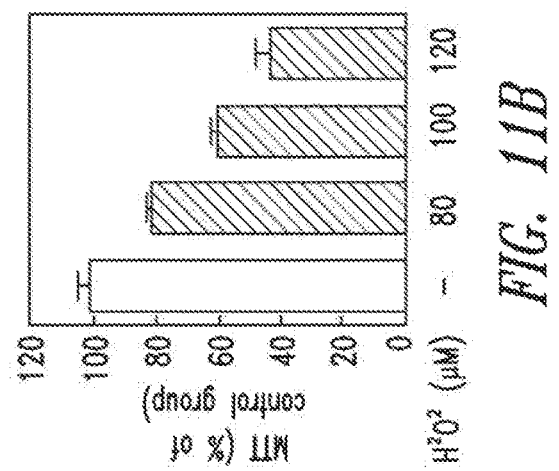
FIGS. 11A-E show that HRS-SV11 does not utilize and extracellular mechanism to protect neurons from 6-OHDA.

As shown in FIG. 11A, 6-OHDA was auto-oxidized in test tube with time and gave an accumulation of p-quinone. Addition of HRS-SV11 did not reduce the amount of p-quinone generated, while vitamin C, a known anti-oxidant, effectively blocked p-quinone's production. This result indicates that HRS-SV11 does not prevent 6-OHDA's neurotoxicity by directly blocking generation of p-quinone in the extracellular space, but instead utilizes another mechanism.

Figure 11B:
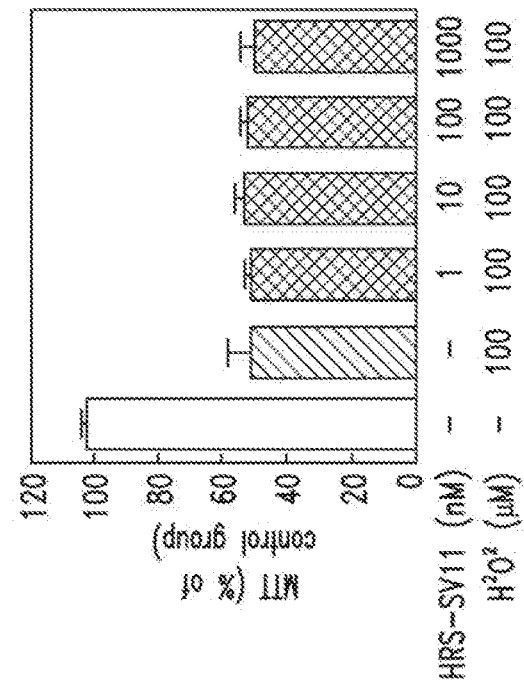
Figure 11C:
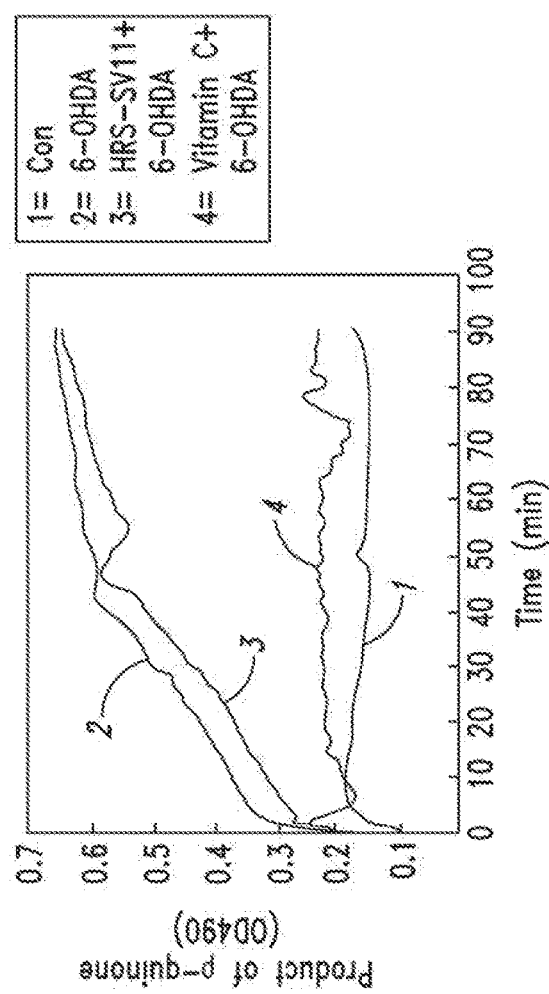

It was also tested whether HRS-SV11 blocks $H_2O_2$-induced neuron death. $H_2O_2$ is another major oxidization product of 6-OHDA, and it has been shown that 6-OHDA-induced PC12 cell death is blocked by catalase, mostly likely by hydrolyzing $H_2O_2$ (see Hanrott et al., 2006). As shown in FIG. 11B, $H_2O_2$ induced cortical neuron death dose-dependently, with an $EC_{50}$ around 120 mM. However, pre-treating cortical neurons with HRS-SV11 (from 1 nM up to 1 μM) did not promote neuronal survival as compared to $H_2O_2$ (120 mM) alone (FIG. 11C). This result suggests that HRS-SV11 either did not prevent or reduce the generation of $H_2O_2$ in the extracellular space, or it did not interfere with the intracellular death pathway initiated by $H_2O_2$.

Figures 11D, 11E:
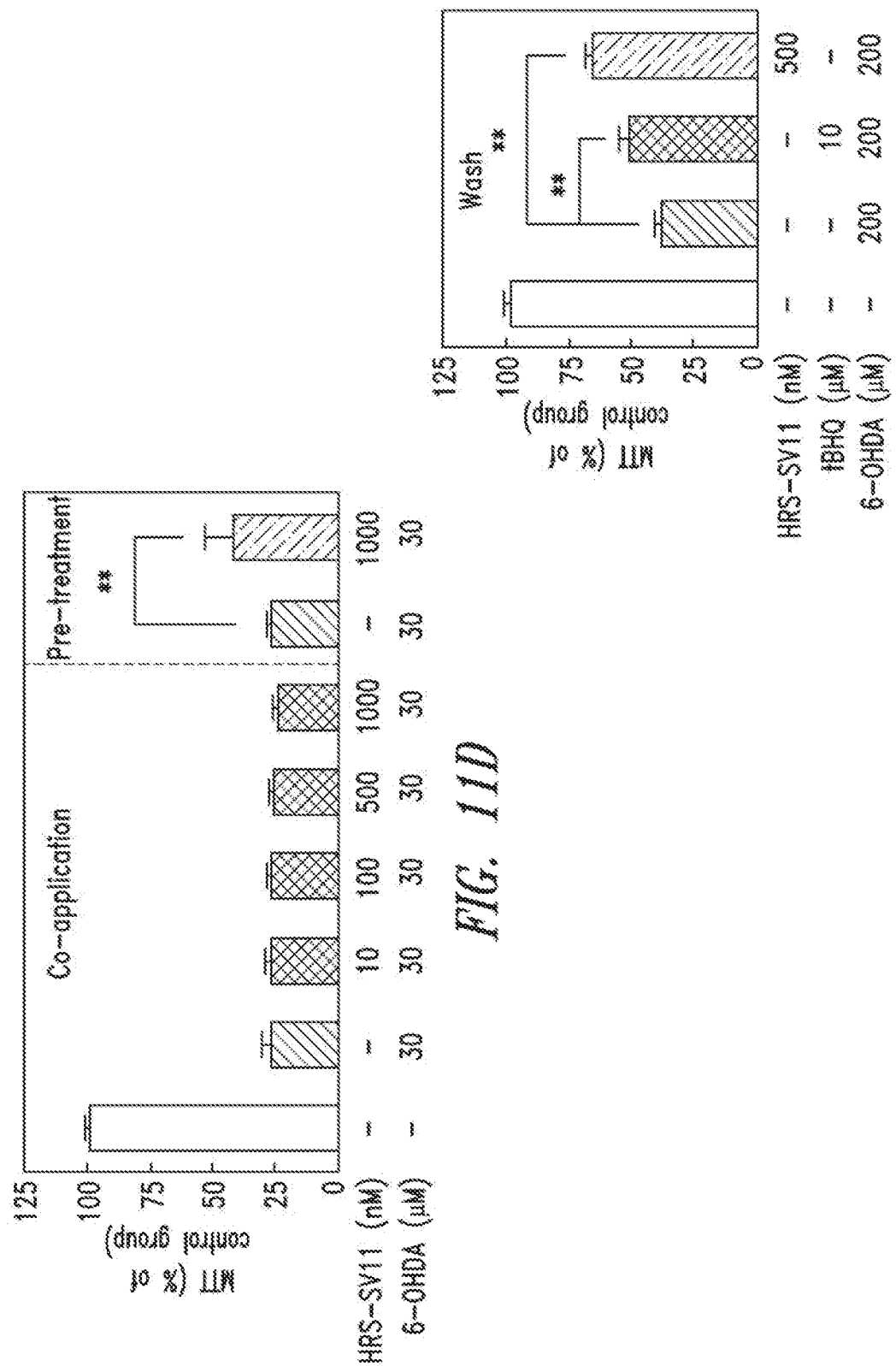
Figure 14A:
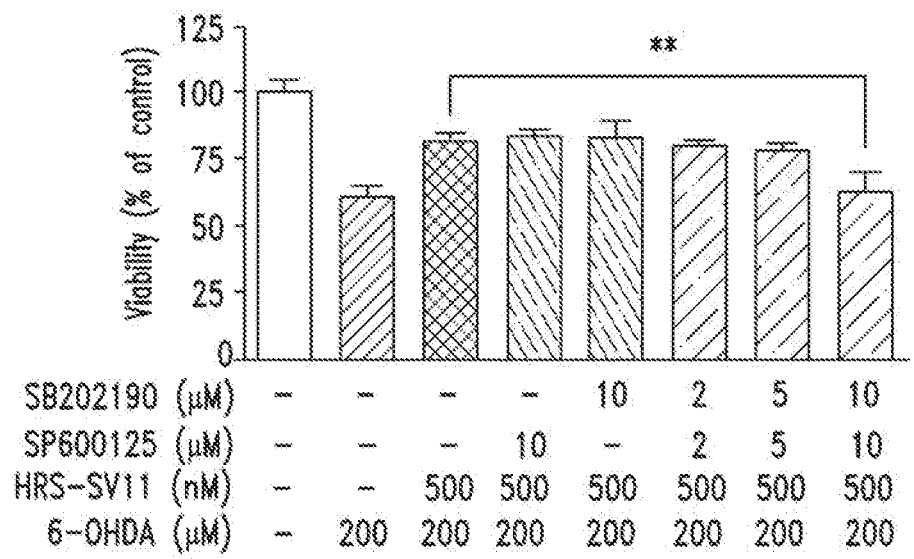
FIGS. 14A-D show that the inhibition of JAK2, JNK and p38 suppressed the neuroprotective effect of HRS-SV11.
Figure 14B:
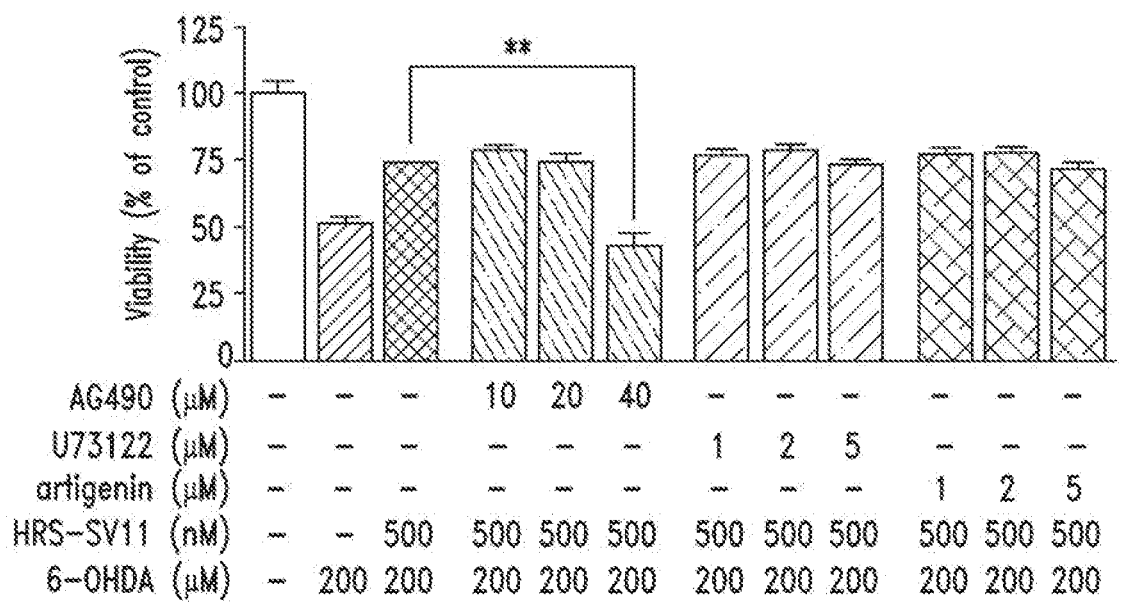
Figure 14C:
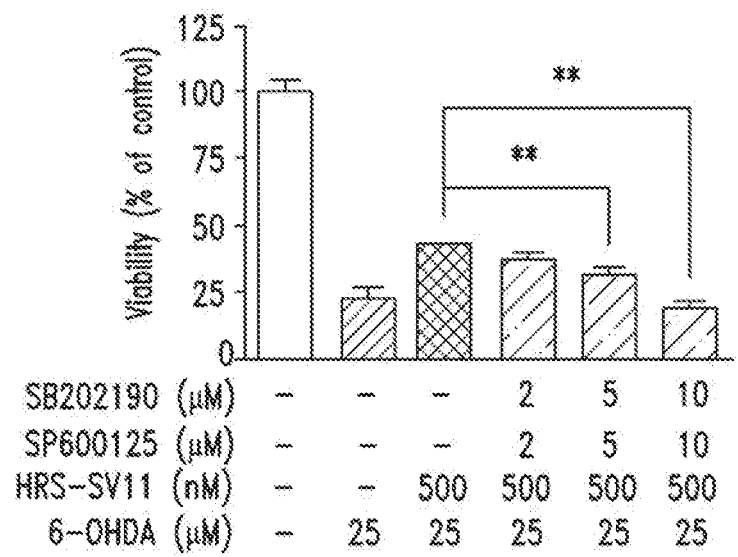
Figure 14D:
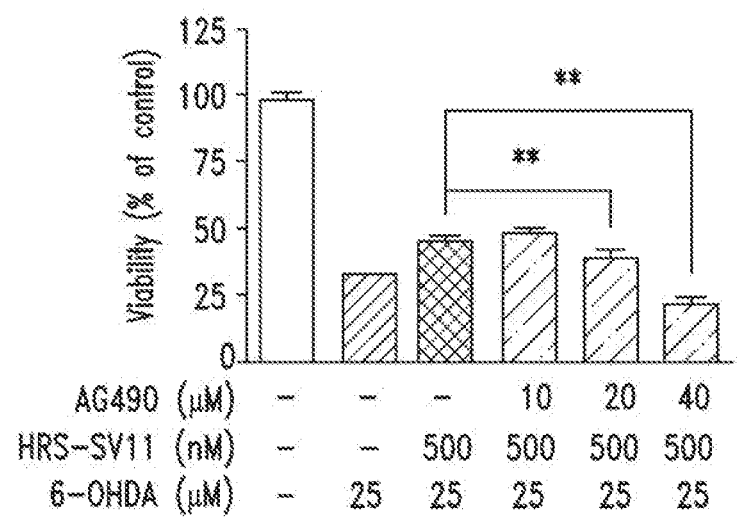

Most anti-oxidants are effective when co-applied with an oxidant. For example, glutathione abolishes p-quinone's toxicity and catalase blocks $H_2O_2$'s toxicity. To confirm previous results in view of this phenomenon, HRS-SV11 was applied simultaneously with 6-OHDA. As shown in FIG. 11D, co-application of HRS-SV11 with 6-OHDA showed no rescue effect in both cortical neurons and PC12 cells.

A wash-out experiment was also performed; prior to the application of 6-OHDA, neurons were washed with PBS and refreshed with culture medium to remove any HRS-SV11 left after pre-incubation with HRS-SV11. This regime reduces the chance of any direct interference with 6-OHDA. As shown in FIG. 11E, the washout did not affect HRS-SV11's protective function. Taken together, these data strongly argued that HRS-SV11 exerts neuronal protection through an alternate signaling mechanism, rather than by reducing 6-OHDA or its oxidized products extracellularly.

Example 9

HRS-SV11 Suppresses 6-OH Da-Induced Apoptosis of Pc12 Cells

Apoptosis has been suggested as a main cause of 6-OHDA's toxicity (see Choi et al., 1999; Blum et al., 2001). Nuclear fragmentation and condensation is a hallmark of late apoptosis. Hoechst 33342 was used to stain and identify apoptotic cells after exposure to 6-OHDA in the presence or absence of HRS-SV11. As shown in FIG. 12, around 20% PC12 cells underwent apoptosis after 8 hrs exposure to 200 μM 6-OHDA, as discriminated by Hoechst staining. Pre-treatment with HRS-SV11 (at 1000 nM) greatly reduced the portion of apoptotic cells (see FIG. 12D for apoptotic cell counts). This result suggests that HRS-SV11 protected PC12 cells through suppression of apoptosis induced by 6-OHDA.

Example 10

Cysteine Residues Contribute to the Neuroprotective Effects of HRS-SV11

Figure 13A:
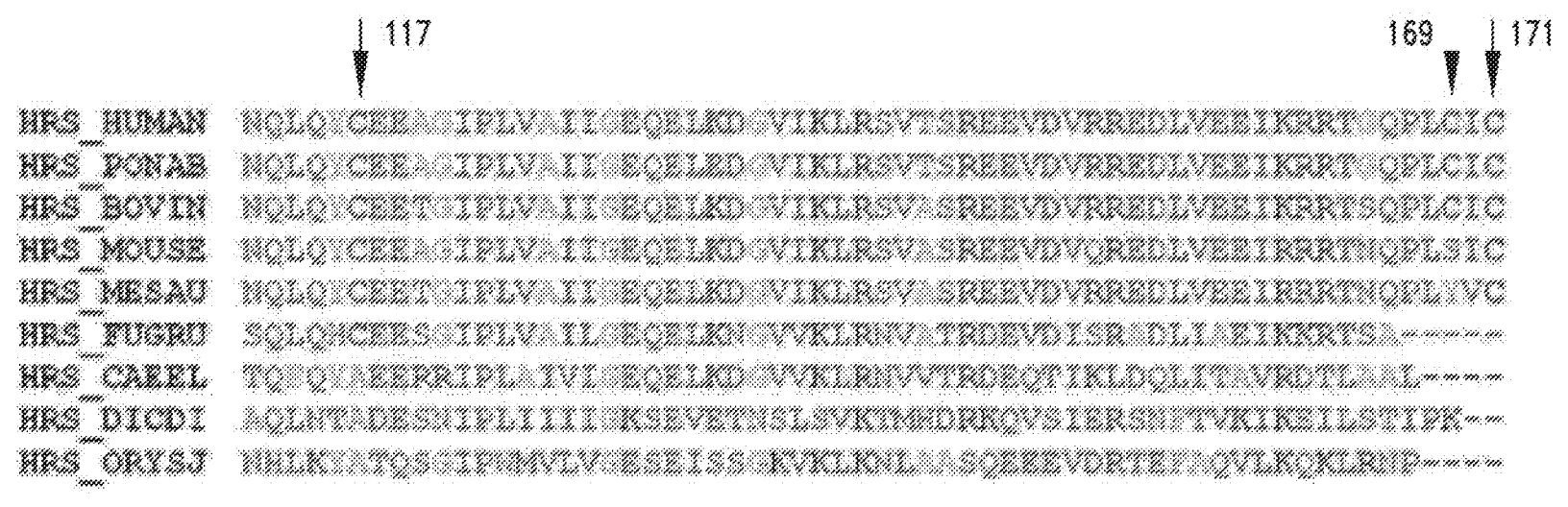

HRS-SV11 contains three cysteines (Cys): Cys117, 169 and 171. Cys169 is the last third amino acid and Cys171 is the last amino acid (see FIG. 13A). Cys169 and Cys 171 were modified to achieve a homogenous monomer population of HRS-SV11 for structural studies. Two mutants were made, (1) HRS-SV11_delC and (2) HRS-SV11_C2S.

The HRS-SV11_delC variant (referred to as delC) has the last three amino acids (including Cys169 and Cys171) in HRS-SV11 deleted. The HRS-SV11_C2S variant (referred to as C2S) has Cys169 and Cys171 mutated to serine residues (Ser).

Analytical gel filtration chromatography was carried out on the proteins using an AKTA FPLC system (GE Healthcare). Protein samples were loaded onto a Superose 12 10/300 GL column (GE Healthcare) equilibrated with a buffer containing 50 mM Tris-HCl pH 7.5, 100 mM NaCl, and 1 mM DTT. As analyzed by analytical gel filtration (see FIG. 13B), HRS-SV11_C2S had one peak, corresponding to the monomer form, and HRS-SV11_delC had two peaks, a large one corresponding to monomer and a small one corresponding to dimer. Cys 177 was also modified to Ser (the C117S variant), and FIG. 13 shows that this mutation fixed HRS-SV11 in dimer form. Wild type HRS-SV11 was in a form between dimer and monomer, suggesting HRS-SV11 protein dynamically switched between dimer and monomer.

The HRS-SV11 mutants were also tested in the 6-OHDA-induced PC12 cell death model. As shown in FIG. 13C, the C2S and delC mutants lost the protective function observed with the wild type HRS-SV11 protein, indicating the importance of these two cysteines for HRS-SV11's neuroprotection.

Example 11

HRS-SV11 Exerts Neuroprotection Through JAK2, JNK and p38

To explore the neuroprotective signaling pathway of HRS-SV11, a number of specific chemical inhibitors were used to interfere with specific signaling molecules. The results are shown in FIG. 14. From a panel of inhibitors, it was found that inhibition of JAK2 (by AG490 at 40 µM), JNK and p38 together (by SB202190 at 10 µM and SP600125 at 10 µM), suppressed HRS-SV11's protective effect, while inhibiting phospholipase C (PLC) by U73122, or MKK by arctigenin, or JNK or p38 alone, had no effect in PC12 cells. These results suggest involvement of JAK2, JNK and p38 in HRS-SV11's signaling.

Example 12

HRS-SV11 Binds to CCR5

To further understand HRS-SV11's neuroprotection, potential cognate receptors on cell surface were identified. An artificial fragment containing amino acid 1-48 of HRS (1-48 a.a.), as well as wild type HRS protein, induced CCR5-expressing HEK293T cells migration, but a deletion mutant without a.a. 1-48 did not (Howard et al., 2002). Since HRS-SV11 contains the a.a.1-48 of wild-type HRS, CCR5 was tested as a candidate receptor for HRS-SV11.

Human CCR5 was amplified and cloned into to pEGFP-N1 vector. Human CCR1 receptor, also a CC chemokine receptor, was included as a control. HEK293T cells were transfected with CCR5-EGFP or CCR1-EGFP plasmids and 1 d after transfection, cells were washed with PBS and detached from culture dish by trypsin. 1×10^6 cells were put into FACS tube in 100 µl complete media and kept on ice (cells were kept cold for remainder of the assay). Cells were treated with recombinant HRS-SV11 protein for 45'. Then cells were washed once with 1 ml staining buffer (1×PBS+ 3% FBS) and spin down at 4° C., 400×g for 10'. After wash, cells were incubated with 0.3 µl primary anti-V5-FITC antibody (3 µg/ml) in 100 µl staining buffer for 30' in dark (kept in dark for remainder of the assay). Cells were then washed twice with 1 ml staining buffer, 4° C., 400×g for 10' and spun down. After the final wash, cell pellets were resuspended in 800 µl staining buffer and analyzed immediately by FACS.

Figure 15B:
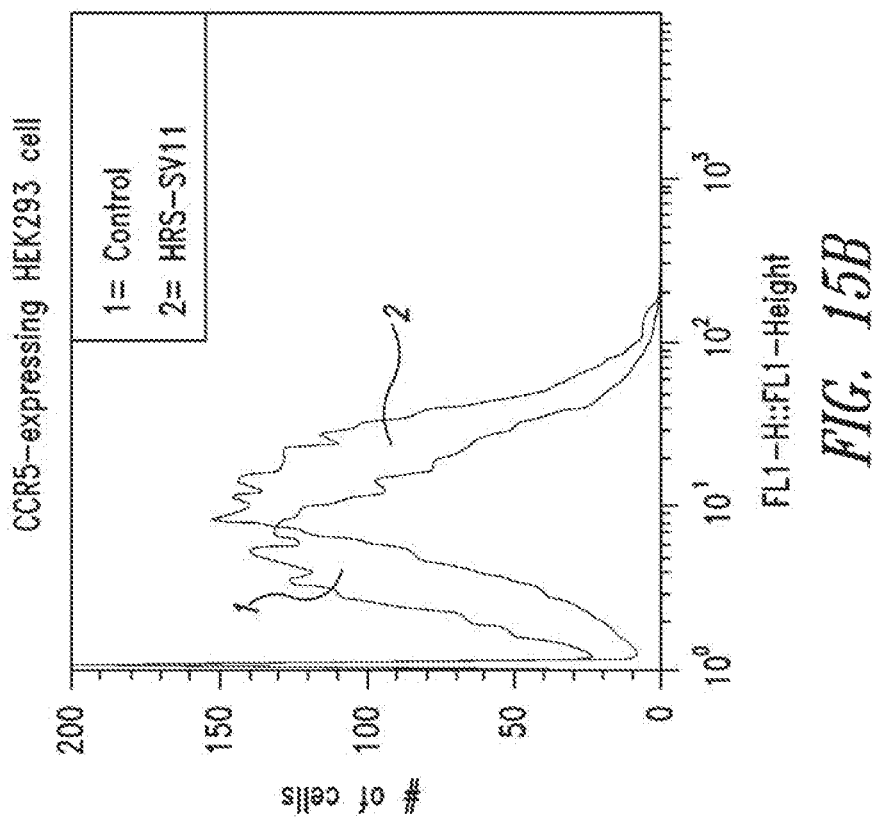
FIGS. 15A-D show that HRS-SV11 bound to CCR5-expressing HEK293T cells, but not to CCR1-expressing or non-transfected cells. As in FIGS. 15A-B, HRS-SV11 did not bind to HEK293T cells (FIG. 15A), but bound to CCR5-expressing HEK293T cells (FIG. 15B).
Figure 15A:
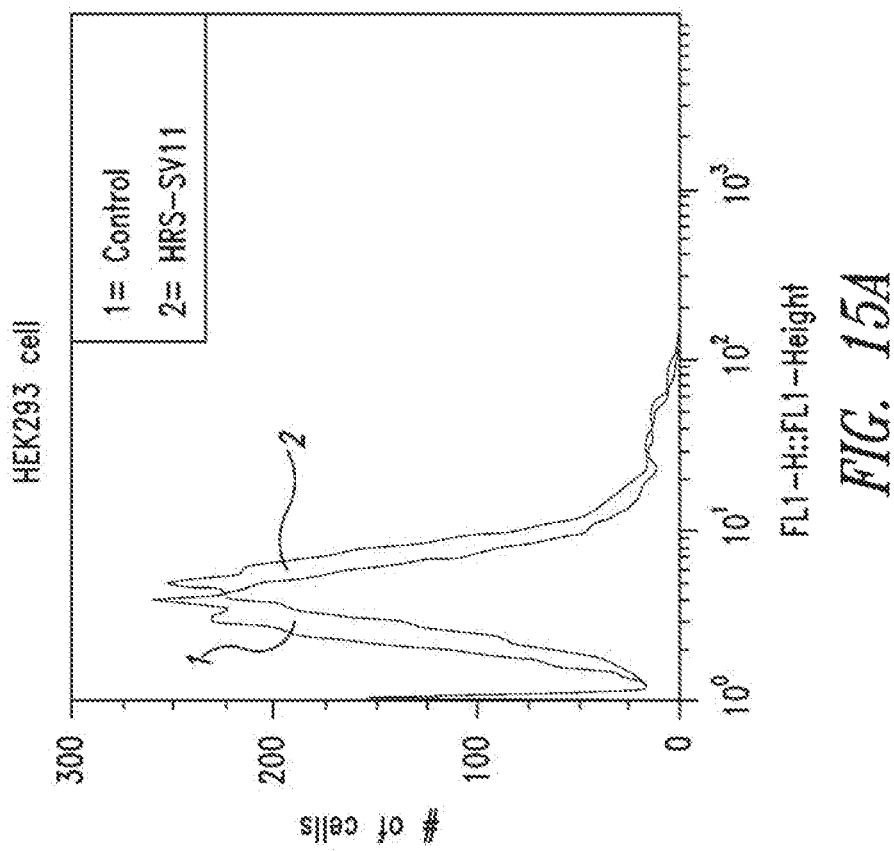
Figure 15D:
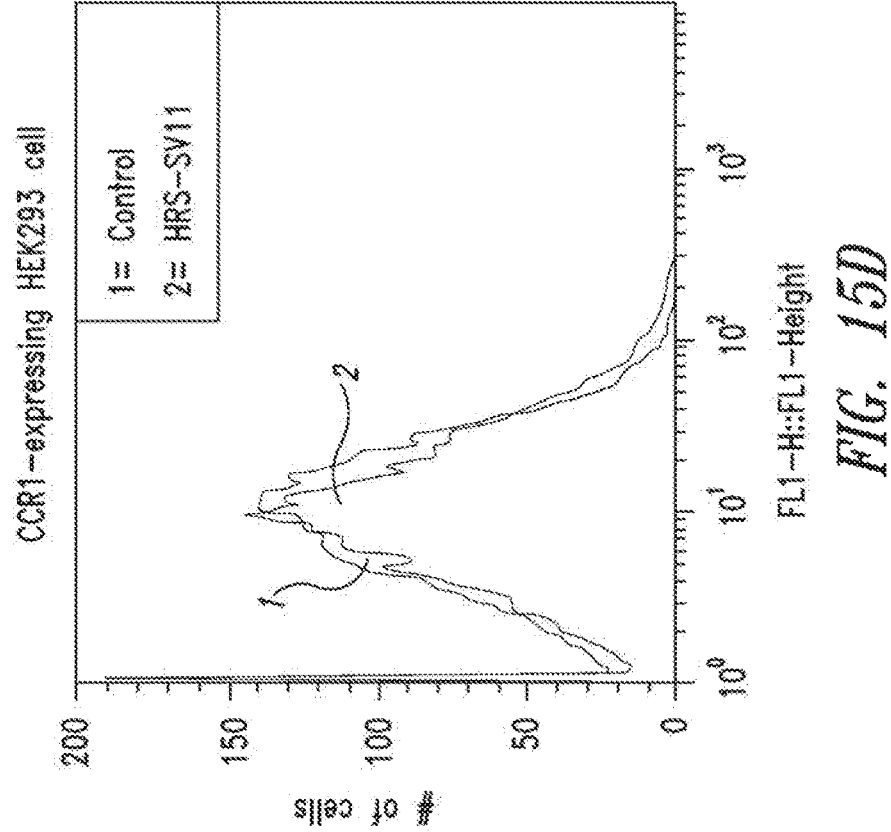
Figure 15C:
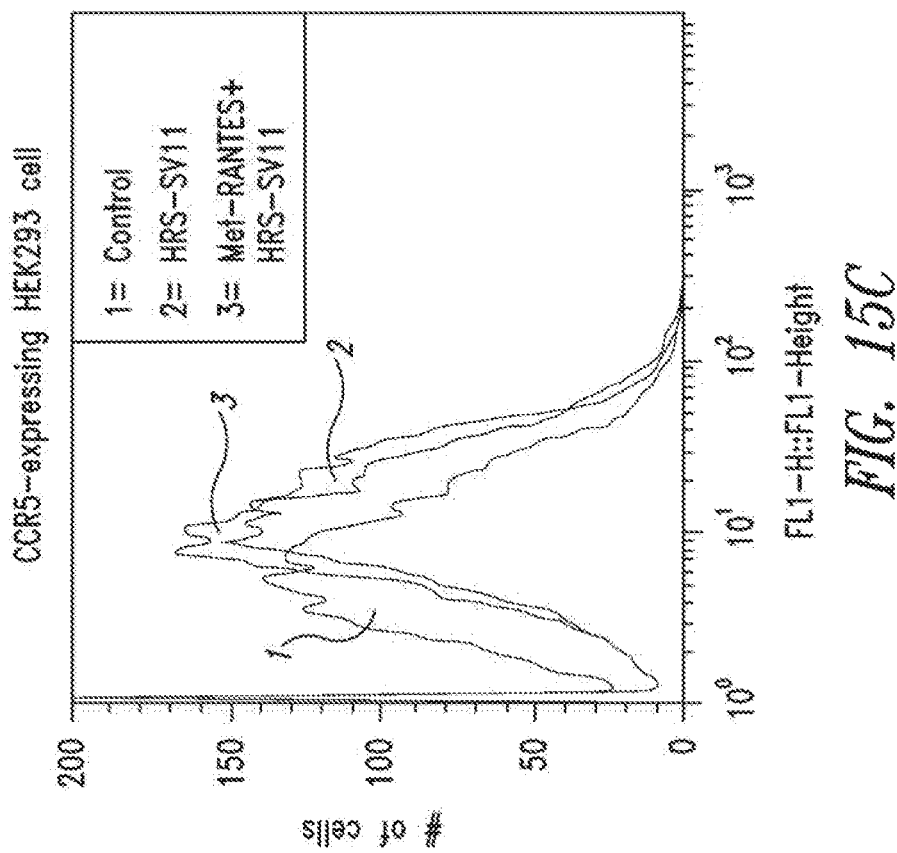

Both CCR5-EGFP and CCR1-EGFP protein localized properly to cell membrane when transfected into HEK293T cells as expected (data not shown). By Fluorescence-activated cell sorting (FACS), it was found that application of recombinant HRS-SV11 protein to CCR5-expressing HEK293T cells increased surface binding of His tag antibody as reflected by a right shift of the curve (FIG. 15B), but had no shift in CCR1-expressing cells (FIG. 15D), suggesting that CCR5 is a potential receptor for HRS-SV11. As shown in FIG. 15C, this shift was not affected by pre-treating CCR5-expressing HEK293T cells with Met-RANTES, a CCR5 agonist. Since Met-RANTES binds to the N-terminus of CCR5 receptor, this data suggests that the N-terminus of CCR5 is not involved in HRS-SV11 binding to CCR5.

Example 13

Figure 16A:
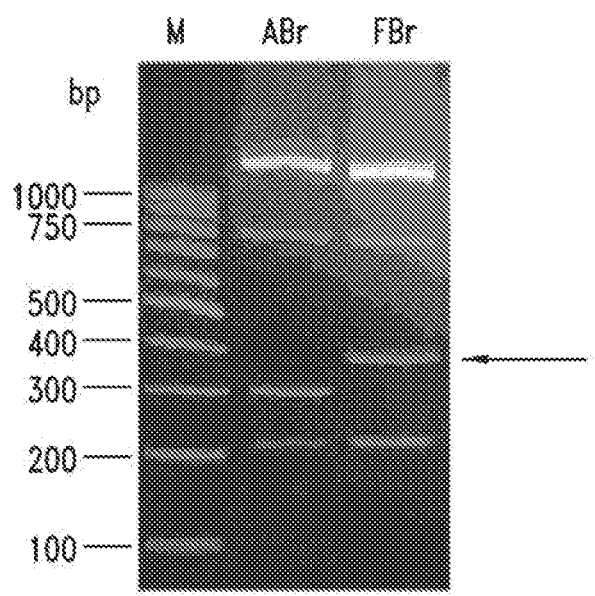
FIGS. 16A-D show identification of the HRS-SV14 splice variant and neuroprotection of HRS-SV14.

Identification of a Neuroprotective Alternative Splice Variant, HRS-SV14, of the Human Histidyl-tRNA Synthetase (HRS) Gene In this experiment, another splicing variant of HRS gene, named HRS-SV14, was identified from human fetus brain by nested PCR (see FIG. 16A, arrow). To set-up the first PCR reaction, a 10-ul reaction mixture was generated containing 1 µl of first strand cDNA, 1× of Advantage 2 PCR buffer (Clontech), 200 µM of each dNTP (Ambion), 250 µM of each forwards and reverse primers (IDT oligo), and 1.25× of Advantage 2 Polymerase Mix (Clontech). Primers for first PCR were hsH1-E2F1 (5'-TGA AAC TGA AGG CAC AGC TG-3') (SEQ ID NO:12) and hsH1-E13R1 (5'-TCT TCT CTT CGG ACA TCC AC-3') (SEQ ID NO:13). Thermo cycling conditions for first PCR were 1 minute at 95° C. followed by 20 cycles of 20 seconds at 95° C., 30 seconds at 58° C. and 1 minute at 72° C., a final extension of 5 minutes at 72° C. PCR set-up and thermo cycling conditions for nested PCR were as the same as that for first PCR, except that, in nested PCR, template is 1000-fold diluted first PCR product, and primers are rnH1-E02F1 (5'-AAC AGA AGT TCG TCC TCA AAA C-3') (SEQ ID NO:14) and rnH1-E12J13R2(5'-TCC ACC TCT TCT CTG CTC GTC A-3') (SEQ ID NO:15). Nested PCR products were resolved by electrophoresis. Distinct PCR products were isolated and purified by NucleoSpin Extract II kit (Macherey-Nagel). Isolated PCR products were cloned by using TOPO TA Cloning Kit for Sequencing (Invitrogen). Plasmids with PCR products successfully inserted were obtained and sequenced. To identify alternative splicing events, sequences of PCR products were aligned to human HARS mRNA sequence in NCBI database (Accession number: NM_002109).

Figure 16D:
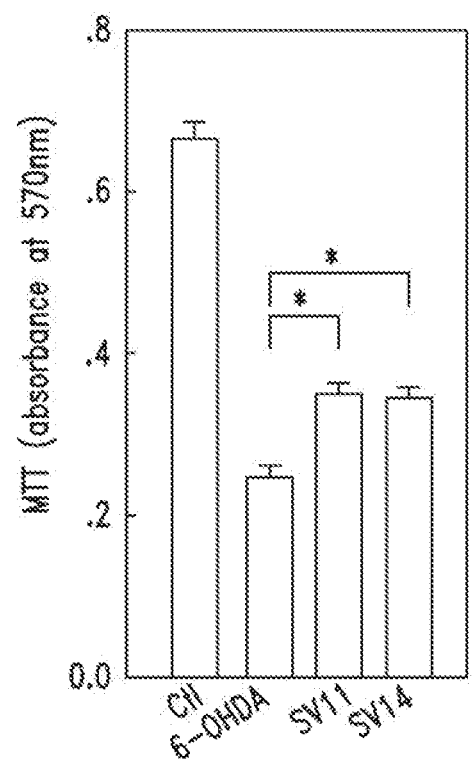
Figure 16B:
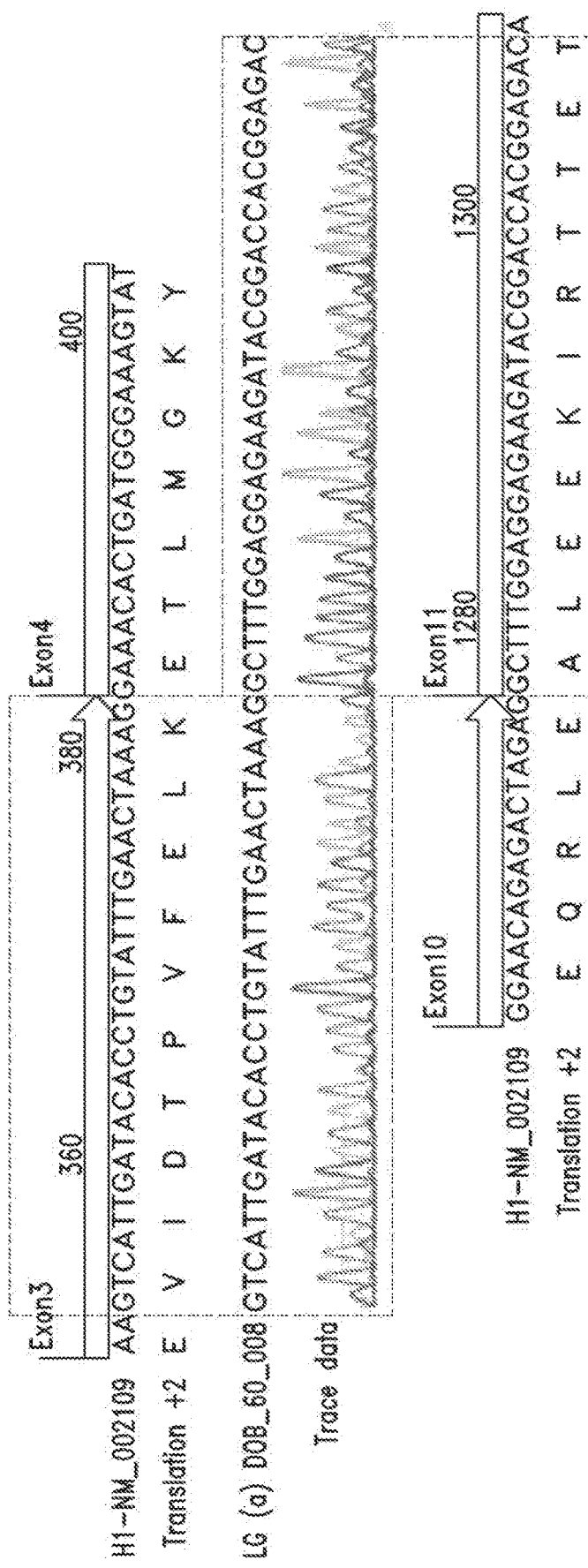
Figure 16C:
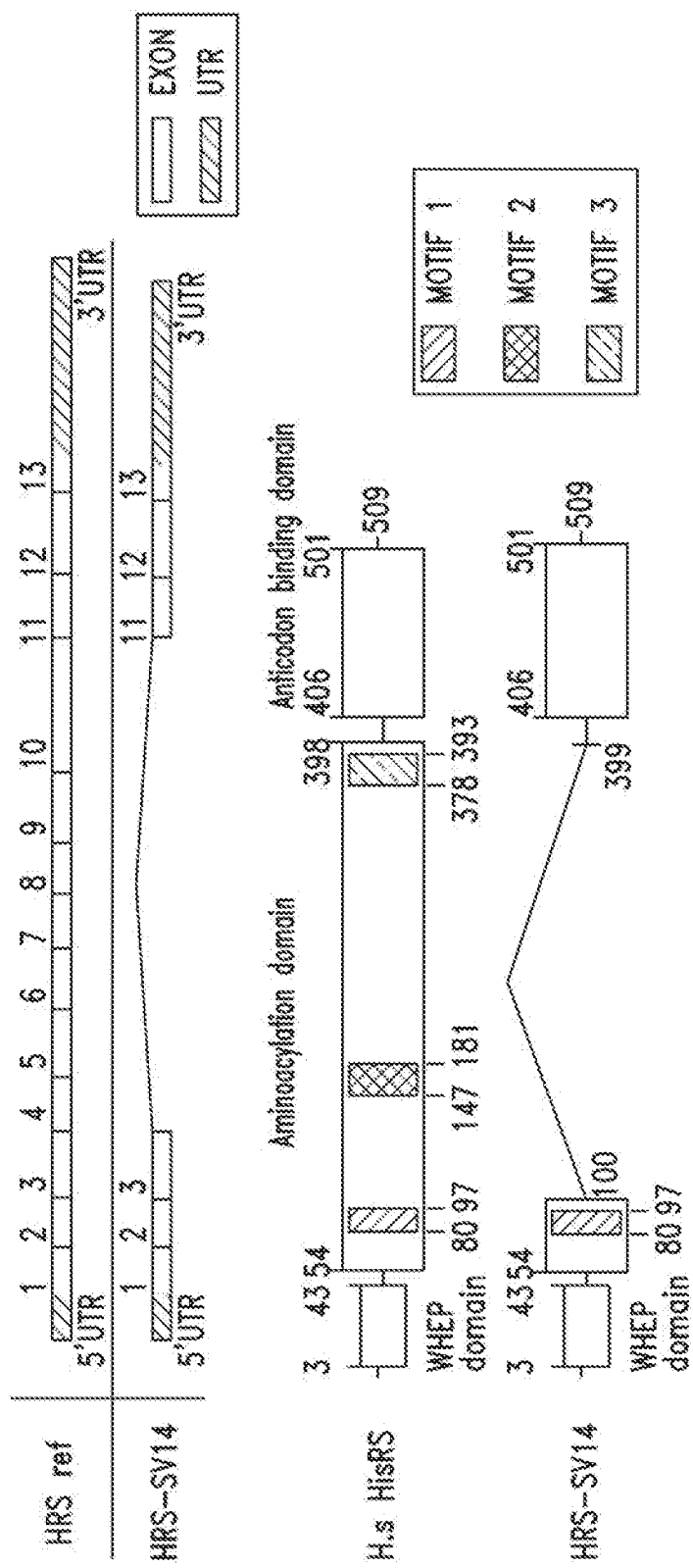
Figure 17:
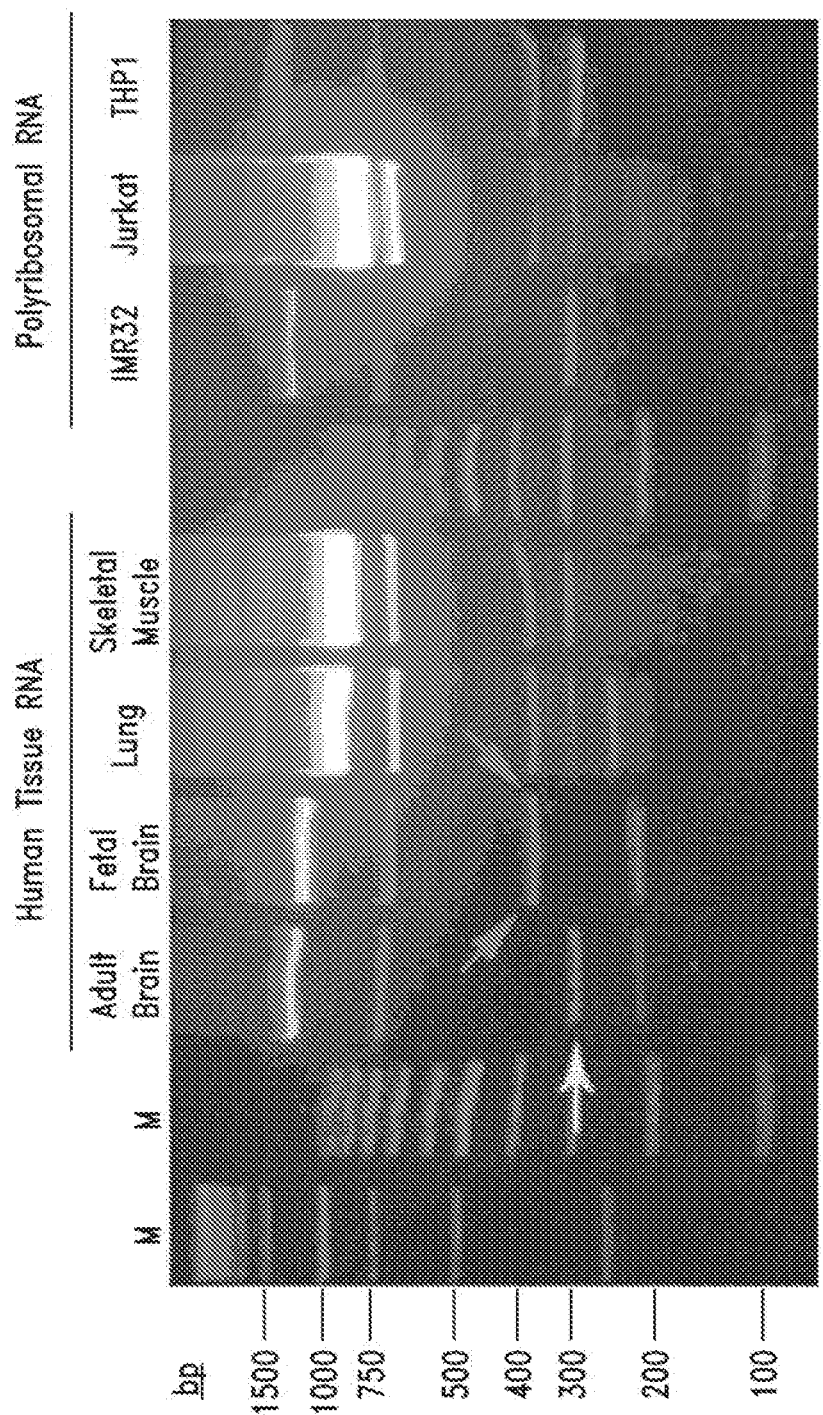
FIG. 17 shows the detection of HRS-SV11 and SV14 transcripts in different tissues and cell lines. This figure shows the electrophoresis of PCR products flanking Exon 2 and Exon 12 of HARS from cDNA of human adult brain, fetus brain, lung, skeletal muscle tissues and IMR32, Jurkat and THP-1 cells. HRS-SV11, as indicated by the horizontal arrow, was present in all the samples, except fetus brain. HRS-SV14, as indicated by angled arrows, was detected in human fetus brain, lung, skeletal muscle, Jurkat and THP-1 cells.
Figure 18B:
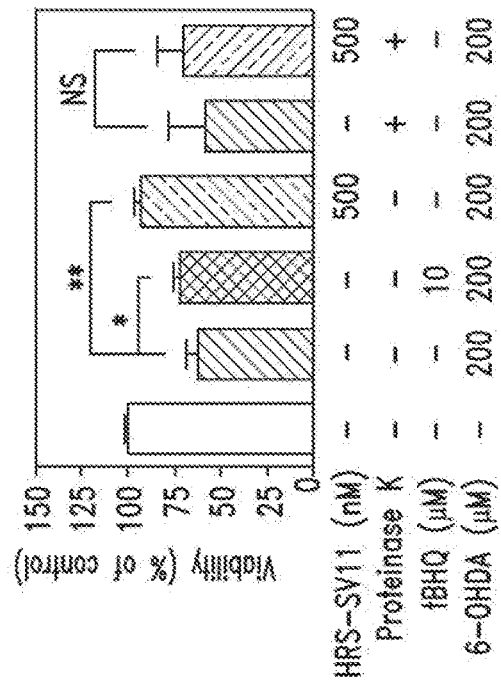
FIGS. 18A-C show that the protective effect of HRS-SV11 recombinant protein was not from non-protein contaminants.
Figure 18C:
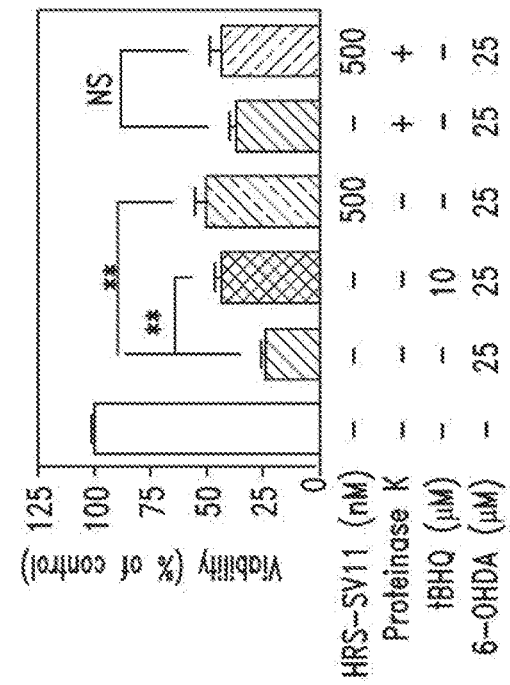
Figure 18A:
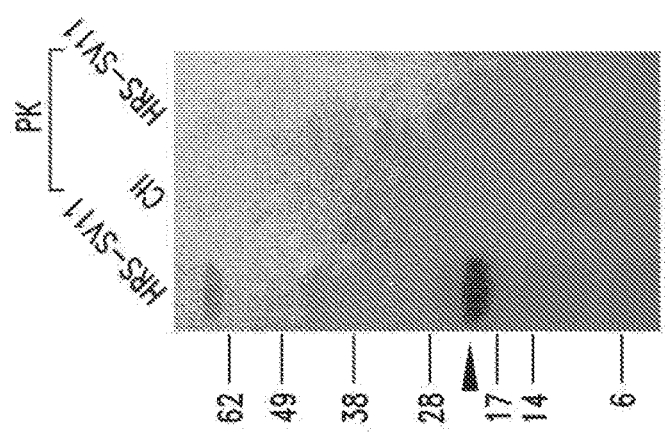

Sequence alignment showed that HRS-SV14 transcript has a deletion of 894 bp, from Exon 4 to Exon 10 of human HRS gene (FIG. 16B), which makes HRS-SV14 protein lack of amino acid 101-398 a.a. of the wild type HRS protein, as shown in FIG. 16C. HRS-SV14 is similar to HRS-SV11, except that it retains Exon 3, which translates into 40 a.a. of the aminoacylation domain.

Recombinant HRS-SV14 protein was then produced and tested for neuroprotective effects in the 6-OHDA-induced PC12 cell death model. As shown in FIG. 16D, pre-treating PC12 cells with 500 nM HRS-SV14 for 24 hrs significantly reduced PC12 cell death upon exposure to 6-OHDA, and the level of neuroprotection was comparable to that of HRS-SV11.

Example 14

Histidyl-tRNA Synthetase Splice Variant SV9 Inhibits THP-1 Migration

To characterize the properties of SV9, a splice variant of the histidyl-tRNA synthetase (amino acids 1-60), a migration assay was set up based on a prior publication suggesting chemoattractant properties for both the full length histidyl-tRNA synthetase and a fragment thereof (amino acids 1-48) [Howard et al. (2002), *J. Exp. Med.*, 196:781-791].

THP-1 cells (ATCC, Catalog #TIB-202) were cultured in RPMI-1640 medium (ATCC, Catalog #30-2001) supplemented with 10% heat-inactivated FBS (Invitrogen, Catalog #10082147) and 0.05 mM 2-β-mercaptoethanol. Cell density was kept at 2-4×10$^5$ cells/ml. Before the migration assay, THP-1 cells were collected by centrifugation, adjusted to a density of 6×10$^6$ cells/ml and starved for 45 minutes in migration buffer (RPMI-1640 medium with 0.1% BSA) containing 6 µg/ml Calcein AM (Invitrogen, Catalog No. C3099). At the same time, SV9 (or PBS as control) was added to the cells at different final concentrations. 100 µl cells (containing 6×10$^5$ cells) pre-treated with SV9 were added to the upper chamber of the migration apparatus. 600

μl migration buffer containing CCL-5 or PBS buffer were added to the lower chamber and cells were allowed to migrate for 2 hours. Cells that migrated to the lower chamber were collected and resuspended in 100 μl PBS, transferred into 384-well opaque Greiner plate and fluorescence was read in a plate reader.

Figure 19:
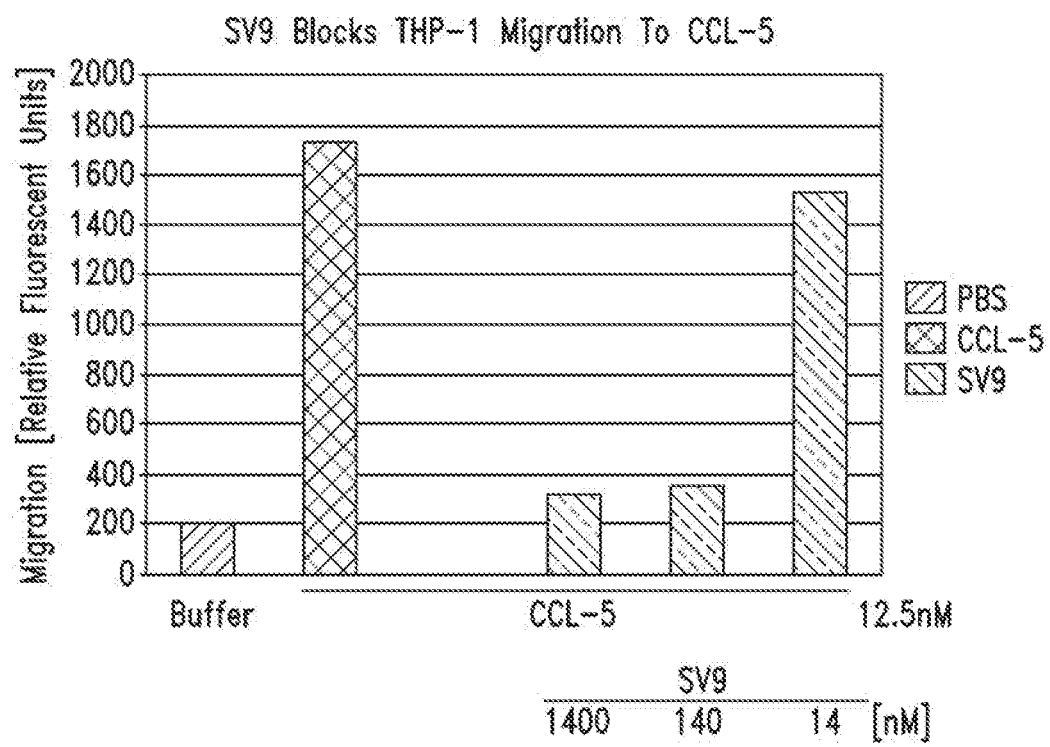
FIG. 19 shows that SV9 inhibits the migration of monocytes (THP-1 cells) towards CCL5.

As shown in FIG. 19, SV9 unexpectedly inhibited migration of THP-1 cells to other ligands such as CCL-5.

Example 15

Histidyl-tRNA Synthetase Splice Variant SV9 Inhibits CCR-1 Mediated THP-1 Migration To further characterize the properties of SV9, the migration assay was used to determine which receptor SV9 engages to inhibit migration of THP-1 cells, since CCL-5 can potentially engage three receptors, CCR1, CCR3 and CCR5.

THP-1 cells (ATCC, Catalog #TIB-202) were cultured in RPMI-1640 medium (ATCC, Catalog #30-2001) supplemented with 10% heat-inactivated FBS (Invitrogen, Catalog #10082147) and 0.05 mM 2-β-mercaptoethanol. Cell density was kept at $2$-$4 \times 10^5$ cells/ml. Before the migration assay, THP-1 cells were collected by centrifugation, adjusted to a density of $6 \times 10^6$ cells/ml and starved for 45 minutes in migration buffer (RPMI-1640 medium with 0.1% BSA) containing 6 μg/ml Calcein AM (Invitrogen, Catalog No. C3099). At the same time, SV9 (or PBS as control) was added to the cells at different final concentrations. 100 μl cells (containing $6 \times 10^5$ cells) pre-treated with SV9 were added to the upper chamber of the migration apparatus. 600 μl migration buffer containing CCL-23, a ligand whose only know reactivity is toward CCR-1, or PBS buffer were added to the lower chamber and cells were allowed to migrate for 2 hours. Cells that migrated to the lower chamber were collected and resuspended in 100 μl PBS, transferred into 384-well opaque Greiner plate and fluorescence was read in a plate reader.

Figure 20:
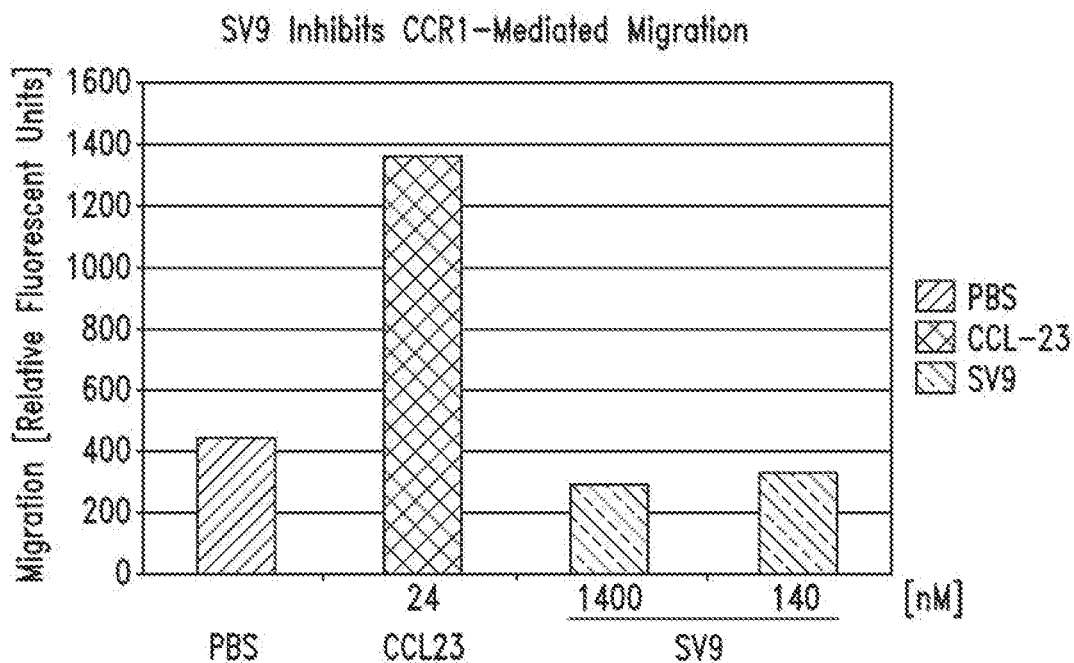
FIG. 20 shows that SV9 inhibits CCR1-mediated migration of THP-1 cells towards CCL-23.

FIG. 20 shows that SV9 inhibits migration of THP-1 cells to CCL-23, and therefore likely inactivates the CCR1 receptor pathway.

Example 16

Histidyl-tRNA Synthetase Splice Variant SV9 Activates Toll-Like Receptors

Previous findings [Parker et al. (2004), *J. Immunol.*, 172:4977-4986] suggested that Toll-like receptor activation can downregulate CCR1. We used a cell-based reporter assay to determine whether SV9 can also activate Toll-like receptors.

RAW-Blue™ cells (InvivoGen, raw-sp) expressing various Toll-like receptors were maintained in DMEM medium (Invitrogen) supplemented with 10% FBS with 1×HEK-Blue™ Selection (InvivoGen, hb-sel). On the day of the assay, the medium was removed and the cells rinsed twice with PBS. The cells were trypsinized or scraped and resuspended in fresh growth medium to prepare a cell suspension at approximately 550,000 cells/ml. 20 μl of SV9, or controls, at various concentrations were added to the wells of a flat-bottom, 96-well plate including a negative control, such as endotoxin-free water. 180 μl of cell suspension (approximately 100,000 cells) were added per well and the plate was incubated at 37° C. in a 5% $CO_2$ incubator for 18-24 hours. The next day, a QUANTI-Blue™ solution was prepared according to the manufacturer's instructions. 160 μl of resuspended QUANTI-Blue™ were transferred to the wells of a 96-well plate, followed by the addition of 40 μl of induced RAW-Blue™ cell supernatant. The plate was then incubated at 37° C. for 30 minutes up to 6 hours. The levels of secreted alkaline phosphatase (SEAP) were determined using a spectrophotometer at 620-655 nm.

Figure 21:
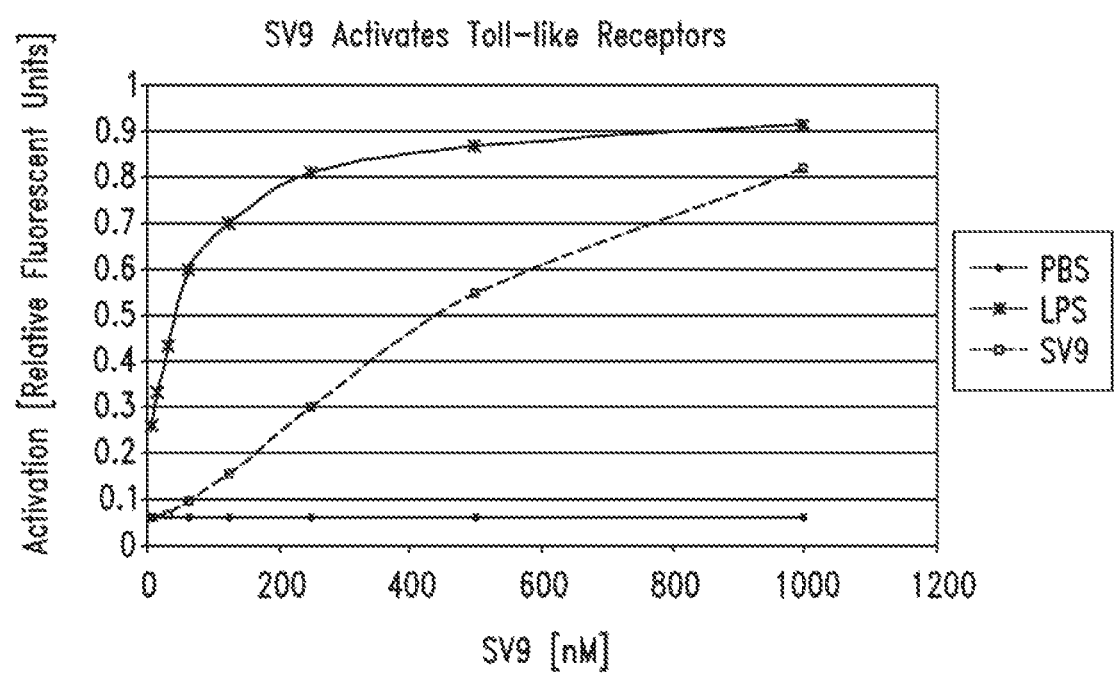
FIG. 21 shows activation of macrophage TLRs by SV9. LPS is a positive control

FIG. 21 shows that SV9 protein activates Toll-like receptors present at the surface of the RAW-Blue™ cells, and stimulates production of the SEAP reporter.

Example 17

Histidyl-tRNA Synthetase Splice Variant SV9 Preferentially Activates Toll-Like Receptor 4

To further characterize which Toll-like receptor SV9 engages, cells expressing only TLR-2 or TLR-4 were used in a similar reporter assay.

TLR-2 or TLR-4 expressing 293 cells (InvivoGen, Catalog #hb2-cells) were maintained in DMEM medium (Invitrogen) supplemented with 10% FBS and 1×HEK-Blue™ Selection (InvivoGen, Catalog #hb-sel). On the day of the assay, 20 μl of SV9 at different concentrations, or controls, were added to the wells of a flat-bottom 96-well plate. A cell suspension of HEK-Blue™-hTLR2 or TLR4 cells was prepared at $5 \times 10^5$ cells per ml in Test Medium (DMEM, 10% heat-inactivated FBS). 90 μl of cell suspension (approximately 50,000 cells) were added per well and the plate was incubated at 37° C. in a $CO_2$ incubator for 20-24 hours. The next day, a QUANTI-Blue™ solution was prepared according to the manufacturer's instructions. 180 μl of resuspended QUANTI-Blue™ (InvivoGen: Catalog #rep-qb1) were transferred to the wells of a 96-well plate, followed by the addition of 20 μl of induced HEK-Blue™-hTLR2 or TLR4 cell supernatant. The plate was then incubated at 37° C. for 1-3 hours. The levels of secreted alkaline phosphatase (SEAP) were determined using a spectrophotometer at 650 nm.

Figures 22A, 22B:
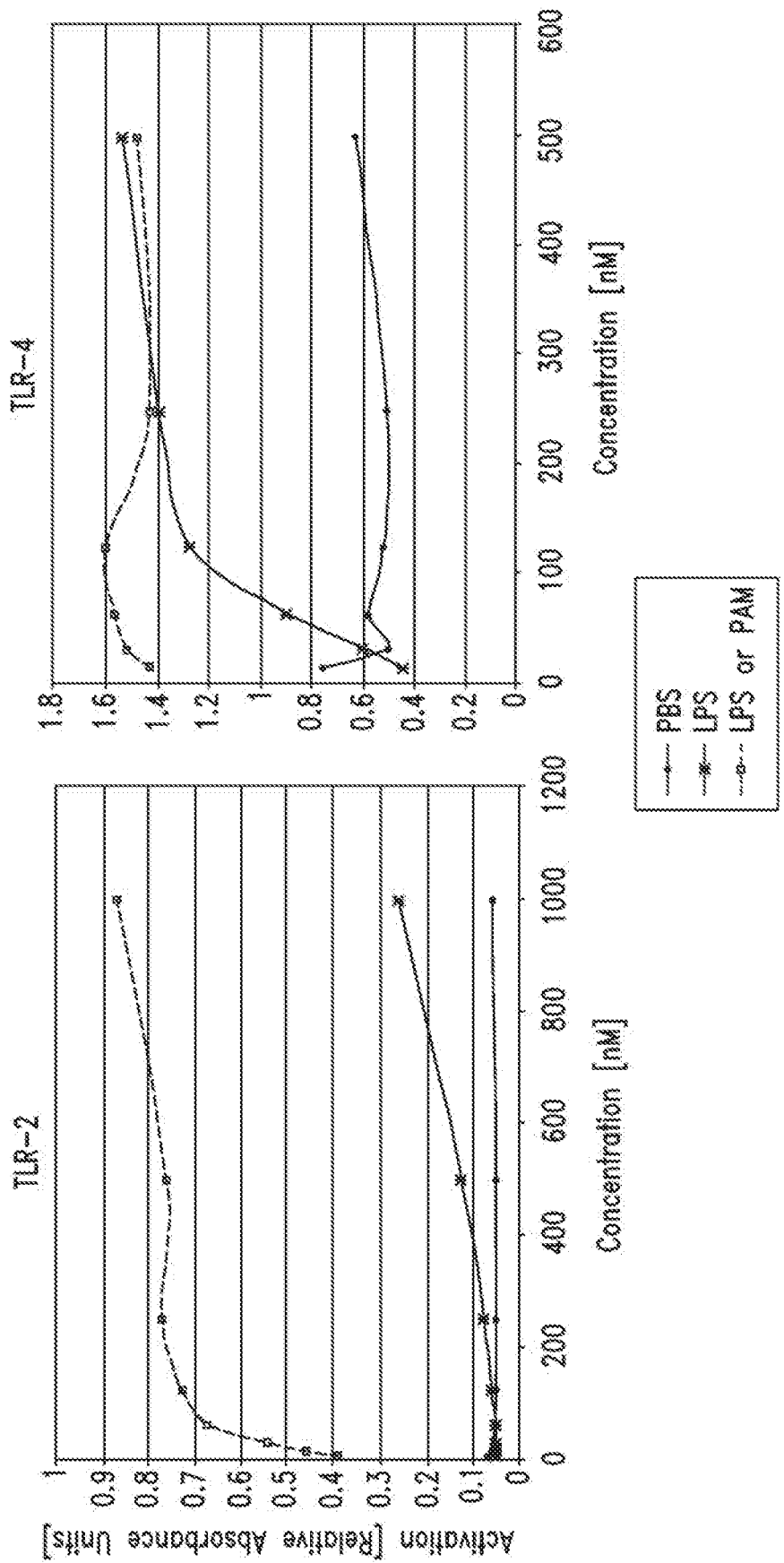
FIGS. 22A and 22B show that SV9 activates both TLR2 (22A) and TLR4 (22B), but preferentially activates TLR4.

FIG. 22 shows that SV9 protein activates both TLR2 (22A) and TLR4 (22B) but is significantly more potent on TLR4.

Example 18

Histidyl-tRNA Synthetase Splice Variant SV9 Stimulates MIP-1-Alpha Secretion

Toll-like receptor activation has been shown to result in MIP-1a secretion which, in turn, could trigger CCR1 down regulation [Parker et al. (2004), *J. Immunol.*, 172:4977-4986]. We used an ELISA assay to determine whether SV9 engagement of the TLR-2 and/or TLR-4 results in MIP-1a secretion.

THP-1 cells (ATCC, Catalog #TIB-202) were cultured in RPMI-1640 medium (ATCC, Catalog #30-2001) supplemented with 10% heat-inactivated FBS (Invitrogen, Catalog #10082147) and 0.05 mM 2-β-mercaptoethanol.

Cells were seeded at a density of $1 \times 10^6$/ml in a 24 well plate and SV9 or LPS at different concentrations was added to each wells. After 24 hour incubation, the supernatant was collected from each well by centrifugation at 250 g and removal of the supernatant. The expression levels of MIP-1a from each sample were determined by using a human CCL3/MIP-1a Immunoassay Quantikine kit (R&D, Catalog #DMA00) according the manufacturer's instructions.

Figure 23:
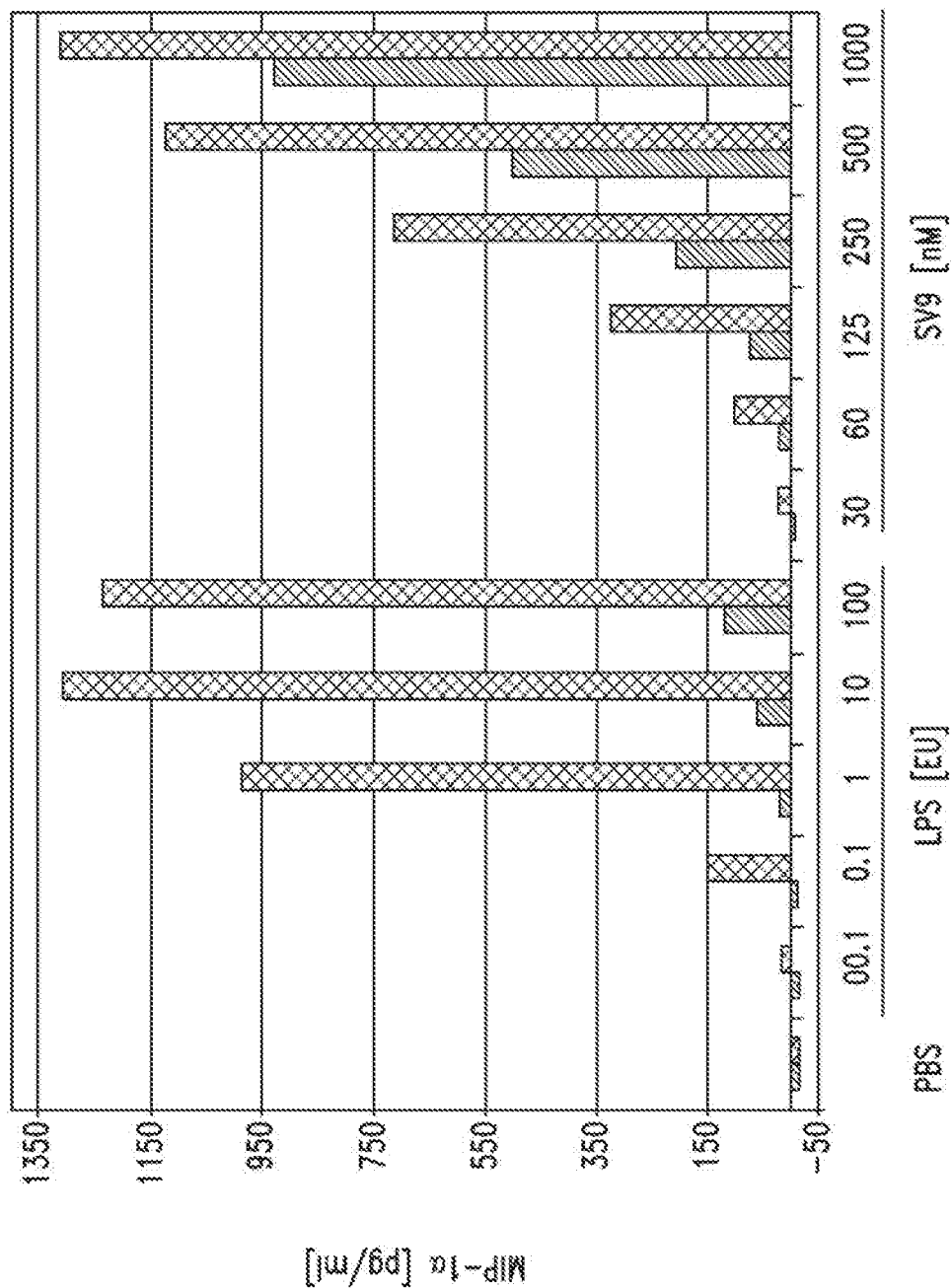
FIG. 23 shows that SV9 stimulates MIP-1a secretion in monocytes (THP-1).

FIG. 23 shows that SV9 stimulates the secretion of MIP-1a with kinetics distinct from LPS.

The disclosure above is descriptive, illustrative and exemplary and is not to be taken as limiting the scope defined by the appended claims which follow.

The invention claimed is:

1. An intranasal spray, or an inhalation or aerosol delivery vehicle, comprising a physiologically acceptable carrier and a fusion polypeptide, wherein the fusion polypeptide comprises a histidyl-tRNA synthetase (HRS) polypeptide fused to an Fc fragment, wherein the HRS polypeptide consists of a sequence that has at least 95% identity along its length to SEQ ID NO: 6, comprises a WHEP domain, and lacks a functional aminoacylation domain.

2. The intranasal spray, or an inhalation or aerosol delivery vehicle, of claim 1, wherein the HRS polypeptide consists of a sequence that has at least 98% identity along its length to SEQ ID NO: 6.

3. The intranasal spray, or an inhalation or aerosol delivery vehicle, of claim 1, wherein the N-terminal region of the HRS reference polypeptide is truncated by 1, 2, or 3 amino acids.

4. A method of delivering a fusion polypeptide composition directly to lungs, comprising administering to a subject the intranasal spray, or inhalation or aerosol delivery vehicle, of any one of claims 1-3.

* * * * *